US008460912B2

(12) United States Patent
Wakita et al.

(10) Patent No.: US 8,460,912 B2
(45) **Date of Patent: *Jun. 11, 2013**

(54) NUCLEIC ACID CONSTRUCT CONTAINING FULL LENGTH GENOME OF HUMAN HEPATITIS C VIRUS, RECOMBINANT FULL LENGTH VIRUS GENOME-REPLICATING CELLS HAVING THE NUCLEIC ACID CONSTRUCT TRANSFERRED THEREINTO AND METHOD OF PRODUCING HEPATITIS C VIRUS PARTICLE

(75) Inventors: Takaji Wakita, Tokyo (JP); Takanobu Kato, Nagoya (JP); Tomoko Date, Kawasaki (JP); Michiko Miyamoto, Fuchu (JP); Jun-ichi Tanabe, Kamakura (JP); Saburo Sone, Yokohama (JP)

(73) Assignees: Tokyo Metropolitan Institute of Medical Science, Tokyo (JP); Toray Industries, Inc., Tokyo (JP)

( * ) Notice: Subject to any disclaimer, the term of this patent is extended or adjusted under 35 U.S.C. 154(b) by 324 days.

This patent is subject to a terminal disclaimer.

(21) Appl. No.: 12/583,465

(22) Filed: Aug. 21, 2009

(65) Prior Publication Data

US 2010/0047896 A1 Feb. 25, 2010

Related U.S. Application Data

(62) Division of application No. 10/589,902, filed as application No. PCT/JP2005/003232 on Feb. 21, 2005, now Pat. No. 7,659,103.

(30) Foreign Application Priority Data

Feb. 20, 2004 (JP) ................................ 2004-045489

(51) Int. Cl.

| | |
|---|---|
| ***C12P 21/00*** | (2006.01) |
| ***C12N 7/00*** | (2006.01) |
| ***C12N 7/01*** | (2006.01) |
| ***C12N 7/02*** | (2006.01) |
| ***A61K 39/29*** | (2006.01) |
| ***C07H 21/00*** | (2006.01) |
| ***A01N 63/00*** | (2006.01) |

(52) U.S. Cl.

USPC .... 435/235.1; 435/69.1; 435/239; 435/320.1; 536/23.72; 424/228.1; 424/93.1; 424/93.2; 424/93.6

(58) Field of Classification Search

None

See application file for complete search history.

(56) References Cited

U.S. PATENT DOCUMENTS

| | | | | |
|---|---|---|---|---|
| 5,428,145 A | 6/1995 | Okamoto et al. | | |
| 6,630,343 B1 | 10/2003 | Bartenschlager | | |
| 7,659,103 B2 * | 2/2010 | Wakita et al. | .............. | 435/235.1 |
| 2003/0009775 A1 | 1/2003 | Glenn | | |
| 2008/0032323 A1 * | 2/2008 | Wakita et al. | .................. | 435/29 |

FOREIGN PATENT DOCUMENTS

| | | | |
|---|---|---|---|
| JP | 6-121689 A | | 5/1994 |
| JP | 2002-171978 A | | 6/2002 |
| WO | WO-00/75337 A1 | | 12/2000 |
| WO | WO-00/75338 A2 | | 12/2000 |
| WO | WO-2004/044182 A2 | | 5/2004 |
| WO | WO 2004/104198 | * | 12/2004 |

OTHER PUBLICATIONS

GenBank BD160781 "Gene of fulminant hepatitis C virus strain," Jan. 2003.*
Ikeda et al., Journal of Virology, vol. 76, No. 6, pp. 2997-3006, (Mar. 2002).
Lim et al., Virology, vol. 303, pp. 79-99, (2002).
Lechmann et al., Hepatology, pp. 417-423, (Aug. 2001).
Scholle et al., Journal of Virology, vol. 78 No. 3, pp. 1513-1524, (Feb. 2004). XP-002417178.
Lohmann et al., Science, vol. 285 pp. 110-113, (Jul. 1999). XP-000960693.
Kato et al., Gastroenterology, vol. 125, No. 6, pp. 1808-1817, (Dec. 2003). XP-002394801.
Friebe et al. Journal of Virology, vol. 75, No. 24, pp. 12047-12057, (Dec. 2001). XP-002977108.
Kimura et al., "Antibody-Free Virion Titer Greatly Differs Between Hepatitis C Virus Genotypes," Journal of Medical Virology, vol. 61, pp. 37-43, (2000).
Date et al., The Journal of Biological Chemistry, vol. 279, No. 21, pp. 22371-22376, 2004.
EMBL Accession No. AB047639, Feb. 25, 2001.
Genbank [online]; National Center for Bio technology Information, Bethesda MD, USA, [retrieved on Dec. 15, 2004], Retrieved from the Internet: URL:http://www.ncbi.nlm.nih.gov:80/entrez/viewer.fcgi?list_uids=13122273>, Accession No. AB047645.
Takanobu Kato, Japan Health Sciences Foundation, pp. 14 to 19, Figs.1 p. 18.
Database EMBL [online]; Feb. 25, 2001, Accession No. EM_VI: AB047644, XP002394805.
Database EMBL [online]; Jan. 17, 2001, Accession No. EM_VI: AF169002, XP002394806.
Kurihara C. et al., J. Med. Virol., vol. 64, pp. 466-475, (2001).
Database EMBL [online]; Jan. 17, 2001, Accession No. EM_PAT: AX057317, XP002394807.

(Continued)

*Primary Examiner* — Michelle S Horning

(74) *Attorney, Agent, or Firm* — Birch, Stewart, Kolasch & Birch, LLP

(57) ABSTRACT

The present invention provides a method for replicating efficiently an RNA containing fulllength HCV genomic sequence and a method for producing HCV virus particles containing fulllength HCV replicon RNA or fulllength HCV genomic RNA by using a cell culture system. Further, the present invention relates to a method for producing hepatitis C virus particles which comprises culturing a cell, into which a replicon RNA comprising a nucleotide sequence comprising a fulllength genomic RNA sequence of hepatitis C virus of the genotype 2a, at least one selectable marker gene and/or at least one reporter gene and at least one IRES sequence or the fulllength genomic RNA of hepatitis C virus of the genotype 2a is introduced, and generating virus particles in the culture medium. Still further the present invention relates also to a hepatitis C vaccine and an antibody against hepatitis C virus particles.

5 Claims, 12 Drawing Sheets
(5 of 12 Drawing Sheet(s) Filed in Color)

OTHER PUBLICATIONS

Simmonds, P. et al., Hepatology, vol. 19, No. 5, pp. 1321-1324 (May 1994).

Choo, Q. L. et al., Science, vol. 244, pp. 359-362, (Apr. 21, 1989).

Okamoto, H. et al., J. of Gen. Virol., vol. 73, pp. 673-679, (1992).

Yoshioka, K. et al., Hepatology, vol. 16, No. 2, pp. 293-299, (1992).

Mori, S. et al., Biochemical and Biophysical Research Communications, vol. 183, No. 1, pp. 334-342, (Feb. 28, 1992).

Blight, K. et al., Science, vol. 290, pp. 1972-1975, (Dec. 8, 2000).

Blanchard, et al., J Virology, (2002), vol. 76(8), pp. 4073-4079.

GenBank AB114136 "Hepatitis C virus replicon . . . " (first available Jan. 2004).

Ciccarone, et al., Focus, (1993), vol. 15, pp. 103-105.

Date, et al., Hepatology Research, (2007), vol. 37(6), pp. 433-443.

Meunier, et al., PNAS USA, (2005), vol. 102(12), pp. 4560-4565.

Pietschmann, et al., J Virology, (2002), vol. 76(8), pp. 4008-4021.

Gottwein, et al., Gastroenterology, (2007), vol. 133(5), pp. 1614-1626.

Mateu, et al., Virology, (2008), vol. 376(2), pp. 397-407.

Sequence alignment, SEQ ID No. 12 and SEQ ID No. 2 from copending U.S. Appl. No. 11/898,468, Nov. 18, 2008.

Hadlosck, et al., J Virology, (2000), vol. 74(22), pp. 10407-10416.

Kato, et al., J Med Virology, (2001), vol. 64(3), pp. 334-339.

Gen Bank No. AF169005, Hepatitis C virus subtype 2a isolate NDM59, complete genome, 2001.

* cited by examiner

SEQUENCE LISTING

<160> NUMBER OF SEQ ID NOS: 26

<210> SEQ ID NO 1
<211> LENGTH: 340
<212> TYPE: RNA
<213> ORGANISM: Hepatitis C virus
<220> FEATURE:
<221> NAME/KEY: misc_feature
<222> LOCATION: (1)..(340)
<223> OTHER INFORMATION: 5' non-translated region of hepatitis C virus genomic RNA derived from JFH-1 clone

<400> SEQUENCE: 1 accugcccu aauaggggcg acacuccgcc augaaucacu ccccugugag gaacuacugu 60
cuucacgcag aaagcgccua gccauggcgu uaguaugagu gucguacagc cuccaggccc 120
cccccucccg ggagagccau aguggucugc ggaaccggug aguacaccgg aauugccggg 180
aagacugggu ccuuucuugg auaaacccac ucuaugcccg gccauuuggg cgugcccccg 240
caagacugcu agccgaguag cguuggguug cgaaaggccu ugugguacug ccugauaggg 300
cgcuugcgag ugccccggga ggucucguag accgugcacc 340

<210> SEQ ID NO 2
<211> LENGTH: 573
<212> TYPE: RNA
<213> ORGANISM: Hepatitis C virus
<220> FEATURE:
<221> NAME/KEY: misc_feature
<222> LOCATION: (1)..(573)
<223> OTHER INFORMATION: core protein-coding sequence of hepatitis C virus genomic RNA derived from JFH-1 clone

<400> SEQUENCE: 2
augagcacaa auccuaaacc ucaaagaaaa accaaaagaa acaccaaccg ucgcccagaa 60
gacguuaagu ucccgggcgg cggccagauc guuggcggag uauacuuguu gccgcgcagg 120
ggccccaggu ugggugugcg cacgacaagg aaaacuucgg agcgguccca gccacguggg 180
agacgccagc ccauccccaa agaucggcgc uccacuggca aggccugggg aaaaccaggu 240
cgccccuggc cccuauaugg gaaugaggga cucggcuggg caggauggcu ccuguccccc 300
cgaggcucuc gccccuccug ggcccccacu gacccccggc auaggucgcg caacgugggu 360
aaagucaucg acacccuaac guguggcuuu gccgaccuca uggggguacau ccccgucgua 420 ggcgccccgc uuaguggcgc cgccagagcu gucgcgcacg gcgugagagu ccuggaggac 480
gggguuaauu augcaacagg gaaccuaccc gguuuccccu uuucuaucuu cuugcuggcc 540
cuguuguccu gcaucaccgu uccggucucu gcu 573

<210> SEQ ID NO 3
<211> LENGTH: 576
<212> TYPE: RNA
<213> ORGANISM: Hepatitis C virus
<220> FEATURE:
<221> NAME/KEY: misc_feature
<222> LOCATION: (1)..(576)
<223> OTHER INFORMATION: E1 protein-coding sequence of hepatitis C virus genomic RNA derived from JFH-1 clone

<400> SEQUENCE: 3
gcccagguga agaauaccag uagcagcuac auggugacca augacugcuc caaugacagc 60
aucacuuggc agcucgaggc ugcgguucuc cacgucccg ggugcguccc gugcgagaga 120
guggggaaua cgucacggug uugggugcca gucucgccaa acauggcugu gcggcagccc 180

-continued

```
ggugcccuca cgcagggucu gcggacgcac aucgauaugg uugugauguc cgccaccuuc    240

ugcucugcuc ucuacguggg ggaccucugu ggcgggguga ugcucgcggc ccagguguuc    300

aucgucucgc cgcaguacca cugguuugug caagaaugca auugcuccau cuacccuggc    360

accaucacug gacaccgcau ggcaugggac augaugauga acuggucgcc cacggccacc    420

augauccugg cguacgugau gcgcgucccc gaggucauca uagacaucgu uagcggggcu    480

cacuggggcg ucauguucgg cuuggccuac uucucuaugc agggagcgug ggcgaagguc    540

auugucaucc uucugcuggc cgcugggug gacgcg                               576


<210> SEQ ID NO 4
<211> LENGTH: 1290
<212> TYPE: RNA
<213> ORGANISM: Hepatitis C virus
<220> FEATURE:
<221> NAME/KEY: misc_feature
<222> LOCATION: (1)..(1290)
<223> OTHER INFORMATION: E2 protein-coding sequence of hepatitis C
      virus genomic RNA derived from JFH-1 clone

<400> SEQUENCE: 4

ggcaccacca ccguuggagg cgcuguugca cguuccacca acgugauugc cggcguguuc     60

agccauggcc cucagcagaa cauucagcuc auuaacacca acggcaguug gcacaucaac    120

cguacugccu ugaauugcaa ugacuccuug aacaccggcu uucucgcggc cuuguucuac    180

accaaccgcu uuaacucguc agggugucca gggcgccugu ccgccugccg caacaucgag    240

gcuuuccgga uagggugggg cacccuacag uacgaggaua augucaccaa uccagaggau    300

augaggccgu acugcuggca cuaccccccca aagccgugug gcguaguccc cgcgaggucu    360

gugugugcc caguguacug uuucaccccc agcccgguag uagugggcac gaccgacaga    420

cguggagugc ccaccuacac augggagag aaugagacag augucuuccu acugaacagc    480

acccgaccgc cgcagggcuc augguucggc ugcacgugga ugaacuccac ugguuucacc    540

aagacuugug gcgcgccacc uugccgcacc agagcugacu ucaacgccag cacggacuug    600

uugugcccua cggauuguuu uaggaagcau ccugaugcca cuuauauuaa guguggguucu   660

gggcccuggc ucacaccaaa gugccugguc cacuacccuu acagacucug gcauuacccc    720

ugcacaguca auuuuaccau cuucaagaua agaauguaug uagggggggu ugagcacagg    780

cucacggccg caugcaacuu cacucguggg gaucgcugcg acuuggagga cagggacagg    840

agucagcugu cuccucuguu gcacucuacc acggaauggg ccauccugcc cugcaccuac    900

ucagacuuac ccgcuuuguc aacuggucuu cuccaccuuc accagaacau cguggacgua    960

caauacaugu auggccucuc accugcuauc acaaaauacg ucguucgaug ggagugggug   1020

guacucuuau uccugcucuu agcggacgcc agagucugcg ccugcuugug gaugcucauc   1080

uuguugggcc aggccgaagc agcauuggag aaguuggucg ucuugcacgc ugcgagugcg   1140

gcuaacugcc auggccuccu auauuuugcc aucuucuucg uggcagcuug gcacaucagg   1200

ggucgggugg uccccuugac caccuauugc cucacuggcc uauggcccuu cugccuacug   1260

cucauggcac ugccccggca ggcuuaugcc                                    1290


<210> SEQ ID NO 5
<211> LENGTH: 651
<212> TYPE: RNA
<213> ORGANISM: Hepatitis C virus
<220> FEATURE:
<221> NAME/KEY: misc_feature
<222> LOCATION: (1)..(651)
```

-continued

<223> OTHER INFORMATION: NS2 protein-coding sequence of hepatitis C virus genomic RNA derived from JFH-1 clone

<400> SEQUENCE: 5
uaugacgcac cugugcacgg acagauaggc guggguuugu ugauauugau cacccucuuc 60
acacucaccc cggggguauaa gacccuccuc ggccagugcuc ugugguggguu gugcuaucuc 120 cugacccugg gggaagccau gauucaggag uggguaccac ccaugcaggu gcgcggcggc 180
cgcgauggca ucgcgugggc cgucacuaua uucugcccgg guguggguguu ugacauuacc 240 aaauggcuuu uggcguugcu ugggccugcu uaccucuuaa gggccgcuuu gacacaugug 300
ccguacuucg ucagagcuca cgcucugaua aggguaugcg cuuuggugaa gcagcucgcg 360 gggggguaggu auguucaggu ggcgcuauug gcccuuggca gguggacugg caccuacauc 420
uaugaccacc ucacaccuau gucggacugg gccgcuagcg gccugcgcga cuuagcgguc 480
gccguggaac ccaucaucuu caguccgaug gagaagaagg ucaucgucug gggagcggag 540
acggcugcau gugggggacau ucuacaugga cuucccgugu ccgcccgacu cggccaggag 600
auccuccucg gcccagcuga uggcuacacc uccaaggggu ggaagcuccu u 651

<210> SEQ ID NO 6
<211> LENGTH: 1893
<212> TYPE: RNA
<213> ORGANISM: Hepatitis C virus
<220> FEATURE:
<221> NAME/KEY: misc_feature
<222> LOCATION: (1)..(1893)
<223> OTHER INFORMATION: NS3 protein-coding sequence of hepatitis C virus genomic RNA derived from JFH-1 clone

<400> SEQUENCE: 6
gcucccauca cugcuuaugc ccagcaaaca cgaggccucc ugggcgccau aguggugagu 60
augacggggc gugacaggac agaacaggcc ggggaagucc aaauccuguc cacagucucu 120
caguccuucc ucggaacaac caucucgggg guuuugugga cuguuuacca cggagcuggc 180
aacaagacuc uagccggcuu acggggguccg gucacgcaga uguacucgag ugcugagggg 240
gacuugguag gcuggcccag ccccccuggg accaagucuu uggagccgug caagugugga 300
gccgucgacc uauaucuggu cacgcggaac gcugauguca ucccggcucg gagacgcggg 360
gacaagcggg gagcauugcu cuccccgaga cccauuucga ccuugaaggg guccucgggg 420
gggccggugc ucugcccuag gggccacguc guugggcucu uccgagcagc ugugugcucu 480
cggggcgugg ccaaauccau cgauuucauc cccguugaga cacucgacgu uguuacaagg 540
ucucccacuu ucagugacaa cagcacgcca ccggcugugc cccagaccua ucaggucggg 600
uacuugcaug cuccaacugg caguggaaag agcaccaagg ucccugucgc guaugccgcc 660
cagggguaca aaguacuagu gcuuaacccc ucgguagcug ccacccuggg guuuggggcg 720
uaccuaucca aggcacaugg caucaauccc aacauuagga cuggagucag gaccgugaug 780
accggggagg ccaucacgua cuccacauau ggcaaauuuc ucgccgaugg gggcugcgcu 840
agcggcgccu augacaucau cauaugcgau gaaugccacg cuguggaugc uaccuccauu 900
cucggcaucg gaacgguccu ugaucaagca gagacagccg ggucagacu aacugugcug 960 gcuacggcca cacccccccgg gucagugaca acccccccauc ccgauauaga agagguaggc 1020
cucgggcggg agggugagau ccccuucuau gggagggcga uuccccuauc cugcaucaag 1080
ggagggagac accugauuuu cugccacuca aagaaaaagu gugacgagcu cgcggcggcc 1140
cuucggggca ugggcuugaa ugccguggca uacuauagag gguuggacgu cuccauaaua 1200

```
ccagcucagg gagauguggu ggucgucgcc accgacgccc ucaugacggg guacacugga   1260

gacuuugacu ccgugaucga cugcaaugua gcggucaccc aagcugucga cuucagccug   1320

gaccccaccu ucacuauaac cacacagacu gucccacaag acgcugucuc acgcagucag   1380

cgccgcgggc gcacagguag aggaagacag ggcacuuaua gguauguuuc cacuggugaa   1440

cgagccucag gaauguuuga caguguagug cuuugugagu gcuacgacgc aggggcugcg   1500

ugguacgauc ucacaccagc ggagaccacc gucaggcuua gagcguauuu caacacgccc   1560

ggccuacccg ugugucaaga ccaucuugaa uuuugggagg caguuuucac cggccucaca   1620

cacauagacg cccacuuccu cucccaaaca aagcaagcgg gggagaacuu cgcguaccua   1680

guagccuacc aagcuacggu gugcgccaga gccaaggccc cucccccguc cugggacgcc   1740

auguggaagu gccuggcccg acucaagccu acgcuugcgg gccccacacc ucuccuguac   1800

cguuugggcc cuauuaccaa ugaggucacc cucacacacc cugggacgaa guacaucgcc   1860

acaugcaugc aagcugaccu ugaggucaug acc                                1893
```

<210> SEQ ID NO 7
<211> LENGTH: 162
<212> TYPE: RNA
<213> ORGANISM: Hepatitis C virus
<220> FEATURE:
<221> NAME/KEY: misc_feature
<222> LOCATION: (1)..(162)
<223> OTHER INFORMATION: NS4A protein-coding sequence of hepatitis C virus genomic RNA derived from JFH-1 clone

<400> SEQUENCE: 7

```
agcacguggg uccuagcugg aggaguccug gcagccgucg ccgcauauug ccuggcgacu     60

ggaugcguuu ccaucaucgg ccgcuugcac gucaaccagc gagucgucgu ugcgccggau    120

aaggaggucc uguaugaggc uuuugaugag auggaggaau gc                       162
```

<210> SEQ ID NO 8
<211> LENGTH: 783
<212> TYPE: RNA
<213> ORGANISM: Hepatitis C virus
<220> FEATURE:
<221> NAME/KEY: misc_feature
<222> LOCATION: (1)..(783)
<223> OTHER INFORMATION: NS4B protein-coding sequence of hepatitis C virus genomic RNA derived from JFH-1 clone

<400> SEQUENCE: 8

```
gccucuaggg cggcucucau cgaagagggg cagcggauag ccgagauguu gaaguccaag     60

auccaaggcu ugcugcagca ggccucuaag caggcccagg acauacaacc cgcuaugcag    120

gcuucauggc ccaaagugga acaauuuugg gccagacaca uguggaacuu cauuagcggc    180

auccaauacc ucgcaggauu gucaacacug ccagggaacc ccgcgguggc uuccaugaug    240

gcauucagug ccgcccucac caguccguug ucgaccagua ccaccauccu ucucaacauc    300

augggaggcu gguuagcguc ccagaucgca ccacccgcgg gggccaccgg cuuugucguc    360

aguggccugg ugggggcugc cgugggcagc auaggccugg guaaggugcu gguggacauc    420

cuggcaggau augguggcggg cauuucgggg gcccucgucg cauucaagau caugucuggc    480

gagaagcccu cuauggaaga ugucaucaau cuacugccug ggauccuguc uccgggagcc    540

cugguggugg gggucaucug cgcggccauu cugcgccgcc acgugggacc gggggagggc    600

gcgguccaau ggaugaacag gcuuauugcc uuugcuucca gaggaaacca cgucgccccu    660

acucacuacg ugacggaguc ggaugcgucg cagcguguga cccaacuacu uggcucucuu    720
```

-continued

```
acuauaacca gccuacucag aagacuccac aauuggauaa cugaggacug ccccauccca    780

ugc                                                                  783


<210> SEQ ID NO 9
<211> LENGTH: 1398
<212> TYPE: RNA
<213> ORGANISM: Hepatitis C virus
<220> FEATURE:
<221> NAME/KEY: misc_feature
<222> LOCATION: (1)..(1398)
<223> OTHER INFORMATION: NS5A protein-coding sequence of hepatitis C
      virus genomic RNA derived from JFH-1 clone

<400> SEQUENCE: 9

uccggauccu ggcuccgcga cgugugggac uggguuugca ccaucuugac agacuucaaa     60

aauuggcuga ccucuaaauu guuccccaag cugcccggcc uccccuucau cucuugucaa    120

aaggggguaca agggugugug ggccggcacu ggcaucauga ccacgcgcug cccuugcggc    180

gccaacaucu cuggcaaugu ccgccugggc ucuaugagga ucacagggcc uaaaaccugc    240

augaacaccu ggcaggggac cuuuccuauc aauugcuaca cggagggcca gugcgcgccg    300

aaaccccccca cgaacuacaa gaccgccauc uggagggugg cggccucgga guacgcggag    360

gugacgcagc augggucgua cuccuaugua acaggacuga ccacugacaa ucugaaaauu    420

ccuugccaac uaccuucucc agaguuuuuc uccugggugg acggugugca gauccauagg    480

uuugcaccca caccaaagcc guuuuuccgg gaugaggucu cguucugcgu ugggcuuaau    540

uccuaugcug ucgggucccca gcuucccugu gaaccugagc ccgacgcaga cguauugagg    600

uccaugcuaa cagauccgcc ccacaucacg gcggagacug cggcgcggcg cuuggcacgg    660

ggaucaccuc caucugaggc gagcuccuca gugagccagc uaucagcacc gucgcugcgg    720

gccaccugca ccacccacag caacaccuau gacguggaca uggucgaugc caaccugcuc    780

auggagggcg guguggcuca gacagagccu gaguccaggg ugcccguucu ggacuuucuc    840

gagccaaugg ccgaggaaga gagcgaccuu gagcccucaa uaccaucgga gugcaugcuc    900

cccaggagcg gguuuccacg ggccuuaccg gcuugggcac ggccugacua caacccgccg    960

cucguggaau cguggaggag gccagauuac caaccgccca ccguugcugg uugugcucuc   1020

ccccccccca agaaggcccc gacgccuccc ccaaggagac gccggacagu gggucugagc   1080

gagagcacca uaucagaagc ccuccagcaa cuggccauca agaccuuugg ccagccccccc   1140

ucgagcggug augcaggcuc guccacgggg gcgggcgccg ccgaauccgg cgguccgacg   1200

uccccuggug agccggcccc cucagagaca gguuccgccu ccucuaugcc cccccucgag   1260

ggggagccug gagauccgga ccuggagucu gaucagguag agcuucaacc uccccccccag   1320

gggggggggg uagcucccgg uucgggcucg gggucuuggu cuacuugcuc cgaggaggac   1380

gauaccaccg ugugcugc                                                 1398


<210> SEQ ID NO 10
<211> LENGTH: 1773
<212> TYPE: RNA
<213> ORGANISM: Hepatitis C virus
<220> FEATURE:
<221> NAME/KEY: misc_feature
<222> LOCATION: (1)..(1773)
<223> OTHER INFORMATION: NS5B protein-coding sequence of hepatitis C
      virus genomic RNA derived from JFH-1 clone

<400> SEQUENCE: 10

uccaugucau acuccuggac cggggcucua auaacucccu guagccccga agaggaaaag     60
```

-continued

```
uugccaauca acccuuugag uaacucgcug uugcgauacc auaacaaggu guacuguaca    120

acaucaaaga gcgccucaca gagggcuaaa aagguaacuu uugacaggac gcaagugcuc    180

gacgcccauu augacucagu cuuaaaggac aucaagcuag cggcuuccaa ggucagcgca    240

aggcuccuca ccuuggagga ggcgugccag uugacuccac cccauucugc aagauccaag    300

uauggauucg gggccaagga gguccgcagc uuguccggga gggccguuaa ccacaucaag    360

uccgugugga aggaccuccu ggaagaccca caaacaccaa uucccacaac caucauggcc    420

aaaaaugagg uguucugcgu ggaccccgcc aagggggggua agaaaccagc ucgccucauc    480

guuuacccug accucggcgu ccgggucugc gagaaaaugg cccucuauga cauuacacaa    540

aagcuuccuc aggcgguaau gggagcuucc uauggcuucc aguacucccc ugcccaacgg    600

guggaguauc ucuugaaagc augggcggaa aagaaggacc ccaugggguu uucguaugau    660

acccgaugcu ucgacucaac cgucacugag agagacauca ggaccgagga guccauauac    720

caggccugcu cccugcccga ggaggcccgc acugccauac acucgcugac ugagagacuu    780

uacguaggag ggcccauguu caacagcaag ggucaaaccu gcgguuacag acguugccgc    840

gccagcgggg ugcuaaccac uagcaugggu aacaccauca caugcuaugu gaaagcccua    900

gcggccugca aggcugcggg gauaguugcg cccacaaugc ugguaugcgg cgaugaccua    960

guagucaucu cagaaagcca ggggacugag gaggacgagc ggaaccugag agccuucacg   1020

gaggccauga ccagguacuc ugccccuccu ggugaucccc ccagaccgga auaugaccug   1080

gagcuaauaa cauccuguuc cucaaaugug ucuguggcgu ugggcccgcg gggccgccgc   1140

agauacuacc ugaccagaga cccaaccacu ccacucgccc gggcugccug ggaaacaguu   1200

agacacuccc cuaucaauuc auggcuggga aacaucaucc aguaugcucc aaccauaugg   1260

guucgcaugg uccuaaugac acacuucuuc uccauucuca ugguccaaga cacccuggac   1320

cagaaccuca acuuugagau guauggauca guauacuccg ugaauccuuu ggaccuucca   1380

gccauaauug agagguuaca cgggcuugac gccuuuucua ugcacacaua cucucaccac   1440

gaacugacgc ggguggcuuc agcccucaga aaacuugggg cgccaccccu cagggugugg   1500

aagagucggg cucgcgcagu cagggcgucc cucaucuccc guggagggaa agcggccguu   1560

ugcggccgau aucucuucaa uugggcggug aagaccaagc ucaaacucac uccauugccg   1620

gaggcgcgcc uacuggacuu auccaguugg uucaccgucg gcgccggcgg gggcgacauu   1680

uuucacagcg ugucgcgcgc ccgaccccgc ucauuacucu ucggccuacu ccuacuuuuc   1740

guagggguag gccucuuccu acuccccgcu cgg                                1773
```

<210> SEQ ID NO 11
<211> LENGTH: 239
<212> TYPE: RNA
<213> ORGANISM: Hepatitis C virus
<220> FEATURE:
<221> NAME/KEY: misc_feature
<222> LOCATION: (1)..(239)
<223> OTHER INFORMATION: 3' non-translated region of hepatitis C virus genomic RNA derived from JFH-1 clone

<400> SEQUENCE: 11

```
uagagcggca cacacuaggu acacuccaua gcuaacuguu ccuuuuuuuu uuuuuuuuuu     60

uuuuuuuuuu uuuuuuuuuu uuuuucuuuu uuuuuuuuuu cccucuuucu ucccuucuca    120

ucuuauucua cuuucuuucu ugguggcucc aucuuagccc uagucacggc uagcugugaa    180

agguccguga gccgcaugac ugcagagagu gccguaacug gucucucugc agaucaugu     239
```

-continued

<210> SEQ ID NO 12
<211> LENGTH: 9678
<212> TYPE: RNA
<213> ORGANISM: Hepatitis C virus
<220> FEATURE:
<221> NAME/KEY: misc_feature
<222> LOCATION: (1)..(9678)
<223> OTHER INFORMATION: full-length Hepatitis C virus genomic RNA derived from JFH-1 clone

<400> SEQUENCE: 12 accugcccu aauaggggcg acacuccgcc augaaucacu ccccugugag gaacuacugu 60
cuucacgcag aaagcgccua gccauggcgu uaguaugagu gucguacagc cuccaggccc 120
cccccucccg ggagagccau aguggucugc ggaaccggug aguacaccgg aauugccggg 180
aagacugggu ccuuucuugg auaaacccac ucuaugcccg gccauuuggg cgugcccccg 240
caagacugcu agccgaguag cguuggguug cgaaaggccu ugugguacug ccugauaggg 300
cgcuugcgag ugccccggga ggucucguag accgugcacc augagcacaa auccuaaacc 360
ucaaagaaaa accaaaagaa acaccaaccg ucgcccagaa gacguuaagu ucccgggcgg 420
cggccagauc guuggcggag uauacuuguu gccgcgcagg ggccccaggu ugggugugcg 480
cacgacaagg aaaacuucgg agcgguccca gccacguggg agacgccagc ccaucccaa 540 agaucggcgc uccacuggca aggccugggg aaaaccaggu cgccccuggc cccuauaugg 600
gaaugaggga cucggcuggg caggauggcu ccuguccccc cgaggcucuc gccccuccug 660
gggccccacu gacccccggc auaggucgcg caacgugggu aaagucaucg acacccuaac 720
guguggcuuu gccgaccuca uggggguacau ccccgucgua ggcgccccgc uuaguggcgc 780
cgccagagcu gucgcgcacg gcgugagagu ccuggaggac gggguuaauu augcaacagg 840
gaaccuaccc gguuuccccu uuucuaucuu cuugcuggcc cuguuguccu gcaucaccgu 900
uccggucucu gcugcccagg ugaagaauac caguagcagc uacaugguga ccaaugacug 960
cuccaaugac agcaucacuu ggcagcucga ggcugcgguu cuccacgucc ccgggugcgu 1020
cccgugcgag agaguggggga auacgucacg guguugggug ccagucucgc caaacauggc 1080
ugugcggcag cccggugccc ucacgcaggg ucugcggacg cacaucgaua ugguugugau 1140
guccgccacc uucugcucug cucucuacgu gggggaccuc uguggcgggg ugaugcucgc 1200
ggcccaggug uucaucgucu cgccgcagua ccacugguuu gugcaagaau gcaauugcuc 1260
caucuacccu ggcaccauca cuggacaccg cauggcaugg gacaugauga ugaacugguc 1320
gcccacggcc accaugaucc uggcguacgu gaugcgcguc cccgagguca ucauagacau 1380
cguuagcggg gcucacuggg gcgucauguu cggcuuggcc uacuucucua ugcagggagc 1440
gugggcgaag gucauuguca uccuucugcu ggccgcuggg guggacgcgg gcaccaccac 1500
cguuggaggc gcuguugcac guuccaccaa cgugauugcc ggcguguuca gccauggccc 1560
ucagcagaac auucagcuca uuaacaccaa cggcaguugg cacaucaacc guacugccuu 1620
gaauugcaau gacuccuuga acaccggcuu ucucgcggcc uuguucuaca ccaaccgcuu 1680
uaacucguca gggguguccag ggcgccuguc cgccugccgc aacaucgagg cuuuccggau 1740 agggugggggc acccuacagu acgaggauaa ugucaccaau ccagaggaua ugaggccgua 1800
cugcuggcac uaccccccaa agccgugugg cguagucccc gcgaggucug ugugugggccc 1860 aguguacugu uucaccccca gcccgguagu aguggggcacg accgacagac guggagugcc 1920
caccuacaca uggggagaga augagacaga ugucuuccua cugaacagca cccgaccgcc 1980
gcagggcuca ugguucggcu gcacguggau gaacuccacu gguuucacca agacuugugg 2040

-continued

```
cgcgccaccu ugccgcacca gagcugacuu caacgccagc acggacuugu ugugcccuac   2100
ggauuguuuu aggaagcauc cugaugccac uuauauuaag ugugguucug ggcccuggcu   2160
cacaccaaag ugccuggucc acuacccuua cagacucugg cauuaccccu gcacagucaa   2220
uuuuaccauc uucaagauaa gaauguaugu aggggggguu gagcacaggc ucacggccgc   2280
augcaacuuc acucgugggg aucgcugcga cuuggaggac agggacagga gucagcuguc   2340
uccucuguug cacucuacca cggaaugggc cauccugccc ugcaccuacu cagacuuacc   2400
cgcuuuguca acuggucuuc uccaccuuca ccagaacauc guggacguac aauacaugua   2460
uggccucuca ccugcuauca caaaauacgu cguucgaugg gagugggugg uacucuuauu   2520
ccugcucuua gcggacgcca gagucugcgc cugcuugugg augcucaucu uguugggcca   2580
ggccgaagca gcauuggaga aguuggucgu cuugcacgcu gcgagugcgg cuaacugcca   2640
uggccuccua uauuuugcca ucuucuucgu ggcagcuugg cacaucaggg gucgggugga   2700
ccccuugacc accuauugcc ucacuggccu auggcccuuc ugccuacugc ucauggcacu   2760
gccccggcag gcuuaugccu augacgcacc ugugcacgga cagauaggcg uggguuuguu   2820
gauauugauc acccucuuca cacucacccc gggguauaag acccuccucg gccagugucu   2880
gugguggug ugcuaucucc ugacccuggg ggaagccaug auucaggagu ggguaccacc   2940
caugcaggug cgcggcggcc gcgauggcau cgcgugggcc gucacuauau ucugcccggg   3000
ugugguguuu gacauuacca aauggcuuuu ggcguugcuu gggccugcuu accucuuaag   3060
ggccgcuuug acacaugugc cguacuucgu cagagcucac gcucugauaa ggguaugcgc   3120
uuuggugaag cagcucgcgg gggguaggua uguucaggug gcgcuauugg cccuuggcag   3180
guggacuggc accuacaucu augaccaccu cacaccuaug ucggacuggg ccgcuagcgg   3240
ccugcgcgac uuagcggucg ccguggaacc caucaucuuc aguccgaugg agaagaaggu   3300
caucgucugg ggagcggaga cggcugcaug uggggacauu cuacauggac uucccguguc   3360
cgccccgacuc ggccaggaga uccuccucgg cccagcugau ggcuacaccu ccaaggggug   3420
gaagcuccuu gcucccauca cugcuuaugc ccagcaaaca cgaggccucc ugggcgccau   3480
agugguggagu augacggggc gugacaggac agaacaggcc ggggaagucc aaauccuguc   3540
cacagucucu caguccuucc ucggaacaac caucucgggg guuuugugga cuguuuacca   3600
cggagcuggc aacaagacuc uagccggcuu acggggucccg gucacgcaga uguacucgag   3660
ugcugagggg gacuugguag gcuggcccag ccccccuggg accaagucuu uggagccgug   3720
caagugugga gccgucgacc uauaucuggu cacgcggaac gcugauguca ucccggcucg   3780
gagacgcggg gacaagcggg gagcauugcu cuccccgaga cccauuucga ccuugaaggg   3840
guccucgggg gggccggugc ucugcccuag gggccacguc guugggcucu uccgagcagc   3900
ugugugcucu cggggcgugg ccaaauccau cgauuucauc cccguugaga cacucgacgu   3960
uguuacaagg ucucccacuu ucagugacaa cagcacgcca ccggcugugc cccagaccua   4020
ucaggucggg uacuugcaug cuccaacugg caguggaaag agcaccaagg ucccugucgc   4080
guaugccgcc cagggguaca aaguacuagu gcuuaacccc ucgguagcug ccacccuggg   4140
guuuggggcg uaccuaucca aggcacaugg caucaauccc aacauuagga cuggagucag   4200
gaccgugaug accggggagg ccaucacgua cuccacauau ggcaaauuuc ucgccgaugg   4260
gggcugcgcu agcggcgccu augacaucau cauaugcgau gaaugccacg cuguggaugc   4320
uaccuccauu cucggcaucg gaacggcccu ugaucaagca gagacagccg gggucagacu   4380
aacugugcug gcuacggcca caccccccgg gucagugaca accccccauc ccgauauaga   4440
```

-continued

```
agagguaggc cucgggcggg agggugagau ccccuucuau gggagggcga uuccccuauc   4500
cugcaucaag ggagggagac accugauuuu cugccacuca aagaaaaagu gugacgagcu   4560
cgcggcggcc cuucggggca ugggcuugaa ugccguggca uacuauagag gguuggacgu   4620
cuccauaaua ccagcucagg gagauguggu ggucgucgcc accgacgccc ucaugacggg   4680
guacacugga gacuuugacu ccgugaucga cugcaaugua gcggucaccc aagcugucga   4740
cuucagccug gaccccaccu ucacuauaac cacacagacu gucccacaag acgcugucuc   4800
acgcagucag cgccgcgggc gcacagguag aggaagacag ggcacuuaua gguauguuuc   4860
cacuggugaa cgagccucag gaauguuuga caguguagug cuuugugagu gcuacgacgc   4920
aggggcugcg ugguacgauc ucacaccagc ggagaccacc gucaggcuua gagcguauuu   4980
caacacgccc ggccuacccg ugugucaaga ccaucuugaa uuuugggagg caguuuucac   5040
cggccucaca cacauagacg cccacuuccu cucccaaaca aagcaagcgg gggagaacuu   5100
cgcguaccua guagccuacc aagcuacggu gugcgccaga gccaaggccc cucccccguc   5160
cugggacgcc auguggaagu gccuggcccg acucaagccu acgcuugcgg gccccacacc   5220
ucuccuguac cguuugggcc cuauuaccaa ugaggucacc cucacacacc cugggacgaa   5280
guacaucgcc acaugcaugc aagcugaccu ugaggucaug accagcacgu ggguccuagc   5340
uggaggaguc cuggcagccg ucgccgcaua uugccuggcg acuggaugcg uuuccaucau   5400
cggccgcuug cacgucaacc agcgagucgu cguugcgccg gauaaggagg uccuguauga   5460
ggcuuuugau gagauggagg aaugcgccuc uagggcggcu cucaucgaag aggggcagcg   5520
gauagccgag auguugaagu ccaagaucca aggcuugcug cagcaggccu cuaagcaggc   5580
ccaggacaua caacccgcua ugcaggcuuc auggcccaaa guggaacaau uuugggccag   5640
acacaugugg aacuucauua gcggcaucca auaccucgca ggauugucaa cacugccagg   5700
gaaccccgcg guggcuucca ugauggcauu cagugccgcc cucaccaguc cguugucgac   5760
caguaccacc auccuucuca acaucauggg aggcugguua gcgucccaga ucgcaccacc   5820
cgcgggggcc accggcuuug ucgucagugg ccuggugggg gcugccgugg gcagcauagg   5880
ccuggguaag gugcuggugg acauccuggc aggauauggu gcgggcauuu cgggggcccu   5940
cgucgcauuc aagaucaugu cuggcgagaa gcccucuaug gaagauguca ucaaucuacu   6000
gccugggauc cugucuccgg gagcccuggu ggugggggucaucugcgcgg ccauucugcg   6060
ccgccacgug ggaccggggg agggcgcggu ccaauggaug aacaggcuua uugccuuugc   6120
uuccagagga aaccacgucg ccccuacuca cuacgugacg gagucggaug cgucgcagcg   6180
ugugacccaa cuacuuggcu cucuuacuau aaccagccua cucagaagac uccacaauug   6240
gauaacugag gacugcccca ucccaugcuc cggauccugg cuccgcgacg ugugggacug   6300
gguuugcacc aucuugacag acuucaaaaa uuggcugacc ucuaaauugu uccccaagcu   6360
gcccggccuc cccuucaucu cuugucaaaa gggguacaag ggugugugggccggcacugg   6420
caucaugacc acgcgcugcc cuugcggcgc caacaucucu ggcaaugucc gccugggcuc   6480
uaugaggauc acagggccua aaaccugcau gaacaccugg caggggaccu uuccuaucaa   6540
uugcuacacg gagggccagu gcgcgccgaa accccccacg aacuacaaga ccgccaucug   6600
gagggguggcg gccucggagu acgcggaggu gacgcagcau gggucguacu ccuauguaac   6660
aggacugacc acugacaauc ugaaaauucc uugccaacua ccuucuccag aguuuuucuc   6720
cuggguggac ggugugcaga uccauagguu ugcacccaca ccaaagccgu uuuuccggga   6780
ugaggucucg uucugcguug ggcuuaauuc cuaugcuguc ggguccccagc uucccuguga   6840
```

-continued

```
accugagccc gacgcagacg uauugagguc caugcuaaca gauccgcccc acaucacggc    6900
ggagacugcg gcgcggcgcu uggcacgggg aucaccucca ucugaggcga gcuccucagu    6960
gagccagcua ucagcaccgu cgcugcgggc caccugcacc acccacagca acaccuauga    7020
cguggacaug gucgaugcca accugcucau ggagggcggu guggcucaga cagagccuga    7080
guccagggug cccguucugg acuuucucga gccaauggcc gaggaagaga gcgaccuuga    7140
gcccucaaua ccaucggagu gcaugcuccc caggagcggg uuuccacggg ccuuaccggc    7200
uugggcacgg ccugacuaca acccgccgcu cguggaaucg uggaggaggc cagauuacca    7260
accgcccacc guugcugguu gugcucuccc cccccccaag aaggccccga cgccuccccc    7320
aaggagacgc cggacagugg gucugagcga gagcaccaua ucagaagccc uccagcaacu    7380
ggccaucaag accuuuggcc agccccccuc gagcggugau gcaggcucgu ccacgggggc    7440
gggcgccgcc gaauccggcg guccgacguc cccuggugag ccggccccu cagagacagg    7500
uuccgccucc ucuaugcccc cccucgaggg ggagccugga gauccggacc uggagucuga    7560
ucagguagag cuucaaccuc ccccccaggg gggggggua gcucccgguu cgggcucggg    7620
gucuuggucu acuugcuccg aggaggacga uaccaccgug ugcugcucca ugucauacuc    7680
cuggaccggg gcucuaauaa cucccuguag ccccgaagag gaaaaguugc caaucaaccc    7740
uuugaguaac ucgcuguugc gauaccauaa caaggugua c uguacaacau caaagagcgc    7800
cucacagagg gcuaaaaagg uaacuuuuga caggacgcaa gugcucgacg cccauuauga    7860
cucagucuua aaggacauca agcuagcggc uuccaagguc agcgcaaggc uccucaccuu    7920
ggaggaggcg ugccaguuga cuccacccca uucugcaaga uccaaguaug gauucggggc    7980
caaggagguc cgcagcuugu ccgggagggc cguuaaccac aucaaguccg uguggaagga    8040
ccuccuggaa gacccacaaa caccaauucc cacaaccauc auggccaaaa augaggugu u    8100
cugcguggac cccgccaagg gggguaagaa accagcucgc cucaucguuu acccugaccu    8160
cggcguccgg gucugcgaga aaauggcccu cuaugacauu acacaaaagc uuccucaggc    8220
gguaauggga gcuuccuaug gcuuccagua cuccccugcc caacgggugg aguaucucuu    8280
gaaagcaugg gcggaaaaga aggaccccau ggguuuuucg uaugauaccc gaugcuucga    8340
cucaaccguc acugagagag acaucaggac cgaggagucc auauaccagg ccugcucccu    8400
gcccgaggag gcccgcacug ccauacacuc gcugacugag agacuuuacg uaggagggcc    8460
cauguucaac agcaaggguc aaaccugcgg uuacagacgu ugccgcgcca gcggggugcu    8520
aaccacuagc augggguaaca ccaucacaug cuaugugaaa gcccuagcgg ccugcaaggc    8580
ugcggggaua guugcgccca caaugcuggu augcggcgau gaccuaguag ucaucucaga    8640
aagccagggg acugaggagg acgagcggaa ccugagagcc uucacggagg ccaugaccag    8700
guacucugcc ccuccuggug aucccccag accggaauau gaccuggagc uaauaacauc    8760
cuguuccuca aaugugucug uggcguuggg cccgcggggc cgccgcagau acuaccugac    8820
cagagaccca accacuccac ucgcccgggc ugccugggaa acaguuagac acuccccuau    8880
caauucaugg cugggaaaca ucauccagua ugcuccaacc auaugggguuc gcauggucu    8940
aaugacacac uucuucucca uucucauggu ccaagacacc cuggaccaga accucaacuu    9000
ugagauguau ggaucaguau acuccgugaa uccuuuggac cuuccagcca uaauugagag    9060
guuacacggg cuugacgccu uuucuaugca cacauacucu caccacgaac ugacgcgggu    9120
ggcuucagcc cucagaaaac uuggggcgcc accccucagg guguggaaga gucgggcucg    9180
cgcagucagg gcgucccuca ucucccgugg agggaaagcg gccguuugcg gccgauaucu    9240
```

-continued cuucaauugg gcggugaaga ccaagcucaa acucacucca uugccggagg cgcgccuacu 9300
ggacuuaucc aguugguuca ccgucggcgc cggcgggggc gacauuuuuc acagcguguc 9360
gcgcgcccga ccccgcucau uacucuucgg ccuacuccua cuuuucguag ggguaggccu 9420
cuuccuacuc cccgcucggu agagcggcac acacuaggua cacuccauag cuaacuguuc 9480
cuuuuuuuuu uuuuuuuuuu uuuuuuuuuu uuuuuuuuuu uuuucuuuuu uuuuuuuuuc 9540
ccucuuucuu cccuucucau cuuauucuac uuucuuucuu gguggcucca ucuuagcccu 9600
agucacggcu agcugugaaa gguccgugag ccgcaugacu gcagagagug ccguaacugg 9660
ucucucugca gaucaugu 9678

<210> SEQ ID NO 13
<211> LENGTH: 11111
<212> TYPE: RNA
<213> ORGANISM: Artificial Sequence
<220> FEATURE:
<223> OTHER INFORMATION: replicon RNA comprising full-length Hepatitis C virus genomic RNA derived from JFH-1 clone

<400> SEQUENCE: 13
accugccccu aauaggggcg acacuccgcc augaaucacu ccccugugag gaacuacugu 60
cuucacgcag aaagcgccua gccauggcgu uaguaugagu gucguacagc cuccaggccc 120
cccccucccg ggagagccau aguggucugc ggaaccggug aguacaccgg aauugccggg 180
aagacugggu ccuuucuugg auaaacccac ucuaugcccg gccauuuggg cgugcccccg 240
caagacugcu agccgaguag cguuggguug cgaaaggccu ugugguacug ccugauaggg 300
cgcuugcgag ugccccggga ggucucguag accgugcacc augagcacaa auccuaaacc 360
ucaaagaaaa accaaaagaa acaccaaccg ucgcccaaug auugaacaag auggauugca 420
cgcagguucu ccggccgcuu ggguggagag gcuauucggc uaugacuggg cacaacagac 480
aaucggcugc ucugaugccg ccguguuccg gcugucagcg caggggcgcc cgguucuuuu 540
ugucaagacc gaccuguccg gugcccugaa ugaacugcag gacgaggcag cgcggcuauc 600
guggcuggcc acgacgggcg uuccuugcgc agcugugcuc gacguuguca cugaagcggg 660
aagggacugg cugcuauugg gcgaagugcc ggggcaggau cuccugucau cucaccuugc 720
uccugccgag aaaguaucca ucauggcuga ugcaaugcgg cggcugcaua cgcuugaucc 780
ggcuaccugc ccauucgacc accaagcgaa acaucgcauc gagcgagcac guacucggau 840
ggaagccggu cuugucgauc aggaugaucu ggacgaagag caucaggggc ucgcgccagc 900
cgaacuguuc gccaggcuca aggcgcgcau gcccgacggc gaggaucucg ucgugaccca 960
uggcgaugcc ugcuugccga auaucauggu ggaaaauggc cgcuuuucug gauucaucga 1020
cuguggccgg cugggugugg cggaccgcua ucaggacaua gcguuggcua cccgugauau 1080
ugcugaagag cuuggcggcg aaugggcuga ccgcuuccuc gugcuuuacg guaucgccgc 1140
ucccgauucg cagcgcaucg ccuucuaucg ccuucuugac gaguucuucu gaguuuaaac 1200
ccucucccuc cccccccccu aacguuacug gccgaagccg cuuggaauaa ggccggugug 1260
cguuugucua uauguuauuu uccaccauau ugccgucuuu uggcaaugug agggcccgga 1320
aaccuggccc ugucuucuug acgagcauuc cuaggggucu uuccccucuc gccaaaggaa 1380
ugcaaggucu guugaauguc gugaaggaag caguuccucu ggaagcuucu ugaagacaaa 1440
caacgucugu agcgacccuu ugcaggcagc ggaacccccc accuggcgac aggugccucu 1500
gcggccaaaa gccacgugua uaagauacac cugcaaaggc ggcacaaccc cagugccacg 1560
uugugaguug gauaguugug gaaagaguca aauggcucuc cucaagcgua uucaacaagg 1620

-continued

```
ggcugaagga ugcccagaag guaccccauu guaugggauc ugaucugggg ccucggugca   1680
caugcuuuac auguguuuag ucgagguuaa aaaaacgucu aggccccccg aaccacgggg   1740
acgugguuuu ccuuugaaaa acacgaugau accaugagca caaauccuaa accucaaaga   1800
aaaaccaaaa gaaacaccaa ccgucgccca gaagacguua aguucccggg cggcggccag   1860
aucguuggcg gaguauacuu guugccgcgc aggggcccca gguugggugu gcgcacgaca   1920
aggaaaacuu cggagcgguc ccagccacgu gggagacgcc agcccauccc caaagaucgg   1980
cgcuccacug gcaaggccug ggaaaaacca ggucgccccu ggccccuaua ugggaaugag   2040
ggacucggcu gggcaggaug gcuccugucc ccccgaggcu cucgccccuc cuggggcccc   2100
acugaccccc ggcauagguc gcgcaacgug gguaaaguca ucgacacccu aacguguggc   2160
uuugccgacc ucauggggua caucccguc guaggcgccc cgcuuagugg cgccgccaga   2220
gcugucgcgc acggcgugag aguccuggag gacgggguua auuaugcaac agggaaccua   2280
cccgguuucc ccuuuucuau cuucuugcug gcccuguugu ccugcaucac cguuccgguc   2340
ucugcugccc aggugaagaa uaccaguagc agcuacaugg ugaccaauga cugcuccaau   2400
gacagcauca cuuggcagcu cgaggcugcg guucuccacg uccccgggug cgucccgugc   2460
gagagagugg ggaauacguc acggguguugg gugccagucu cgccaaacau ggcugugcgg   2520
cagcccggug cccucacgca gggucugcgg acgcacaucg auaugguugu gauguccgcc   2580
accuucugcu cugcucucua cgugggggac cucuguggcg gggugaugcu cgcggcccag   2640
guguucaucg ucucgccgca guaccacugg uuugugcaag aaugcaauug cuccaucuac   2700
ccuggcacca ucacuggaca ccgcauggca ugggacauga ugaugaacug gucgcccacg   2760
gccaccauga uccuggcgua cgugaugcgc guccccgagg ucaucauaga caucguuagc   2820
ggggcucacu ggggcgucau guucggcuug gccuacuucu cuaugcaggg agcgugggcg   2880
aaggucauug ucauccuucu gcuggccgcu ggggguggacg cgggcaccac caccguugga   2940
ggcgcuguug cacguuccac caacgugauu gccggcgugu ucagccaugg cccucagcag   3000
aacauucagc ucauuaacac caacggcagu uggcacauca accguacugc cuugaauugc   3060
aaugacuccu ugaacaccgg cuuucucgcg gccuuguucu acaccaaccg cuuuaacucg   3120
ucagggguguc cagggcgccu guccgccugc cgcaacaucg aggcuuuccg gauagggugg   3180
ggcacccuac aguacgagga uaaugucacc aauccagagg auaugaggcc guacugcugg   3240
cacuaccccc caaagccgug uggcguaguc cccgcgaggu cugugugugg cccaguguac   3300
uguuucaccc ccagcccggu aguagugggc acgaccgaca gacguggagu gcccaccuac   3360
acauggggag agaaugagac agaugucuuc cuacugaaca gcacccgacc gccgcagggc   3420
ucaugguucg gcugcacgug gaugaacucc acugguuuca ccaagacuug uggcgcgcca   3480
ccuugccgca ccagagcuga cuucaacgcc agcacggacu uguugugccc uacggauugu   3540
uuuaggaagc auccugaugc cacuuauauu aagugugguu cugggcccug gcucacacca   3600
aagugccugg uccacuaccc uuacagacuc uggcauuacc ccugcacagu caauuuuacc   3660
aucuucaaga uaagaaugua uguagggggg guugagcaca ggcucacggc cgcaugcaac   3720
uucacucgug gggaucgcug cgacuuggag gacagggaca ggagucagcu gucuccucug   3780
uugcacucua ccacggaaug ggccauccug cccugcaccu acucagacuu acccgcuuug   3840
ucaacugguc uucuccaccu ucaccagaac aucguggacg uacaauacau guauggccuc   3900
ucaccugcua ucacaaaaua cgucguucga ugggaguggg ugguacucuu auuccugcuc   3960
uuagcggacg ccagagucug cgccugcuug uggaugcuca ucuuguuggg ccaggccgaa   4020
```

-continued

```
gcagcauugg agaaguuggu cgucuugcac gcugcgagug cggcuaacug ccauggccuc   4080
cuauauuuug ccaucuucuu cguggcagcu uggcacauca ggggucgggu gguccccuug   4140
accaccuauu gccucacugg ccuauggccc uucugccuac ugcucauggc acugccccgg   4200
caggcuuaug ccuaugacgc accugugcac ggacagauag gcgugggguuu guugauauug   4260
aucacccucu ucacacucac cccgggguau aagacccucc ucggccagug ucuguggugg   4320
uugugcuauc uccugacccu gggggaagcc augauucagg aguggguacc acccaugcag   4380
gugcgcggcg gccgcgaugg caucgcgugg gccgucacua uauucugccc ggguguggug   4440
uuugacauua ccaaauggcu uuuggcguug cuugggccug cuuaccucuu aagggccgcu   4500
uugacacaug ugccguacuu cgucagagcu cacgcucuga uaaggguaug cgcuuuggug   4560
aagcagcucg cgggggguag guauguucag guggcgcuau uggcccuugg cagguggacu   4620
ggcaccuaca ucuaugacca ccucacaccu augucggacu gggccgcuag cggccugcgc   4680
gacuuagcgg ucgccgugga acccaucauc uucaguccga uggagaagaa ggucaucguc   4740
uggggagcgg agacggcugc auguggggac auucuacaug gacuucccgu guccgcccga   4800
cucggccagg agauccuccu cggcccagcu gauggcuaca ccuccaaggg guggaagcuc   4860
cuugcuccca ucacugcuua ugcccagcaa acacgaggcc uccugggcgc cauaguggug   4920
aguaugacgg ggcgugacag gacagaacag gccggggaag uccaaauccu guccacaguc   4980
ucucaguccu uccucggaac aaccaucucg gggguuuugu ggacuguuua ccacggagcu   5040
ggcaacaaga cucuagccgg cuuacggggu ccggucacgc agauguacuc gagugcugag   5100
ggggacuugg uaggcuggcc cagccccccu gggaccaagu cuuuggagcc gugcaagugu   5160
ggagccgucg accuauaucu ggucacgcgg aacgcugaug ucaucccggc ucggagacgc   5220
ggggacaagc ggggagcauu gcucuccccg agacccauuu cgaccuugaa gggguccucg   5280
ggggggccgg ugcucugccc uaggggccac gucguugggc ucuuccgagc agcugugugc   5340
ucucggggcg uggccaaauc caucgauuuc auccccguug agacacucga cguuguuaca   5400
aggucuccca cuuucaguga caacagcacg ccaccggcug ugccccagac cuaucagguc   5460
ggguacuugc augcuccaac uggcagugga aagagcacca agguccugu cgcguaugcc   5520
gcccaggggu acaaaguacu agugcuuaac cccucgguag cugccacccu gggguuuggg   5580
gcguaccuau ccaaggcaca uggcaucaau cccaacauua ggacuggagu caggaccgug   5640
augaccgggg aggccaucac guacuccaca uauggcaaau uucucgccga ugggggcugc   5700
gcuagcggcg ccuaugacau caucauaugc gaugaaugcc acgcugugga ugcuaccucc   5760
auucucggca ucggaacggu ccuugaucaa gcagagacag ccggggucag acuaacugug   5820
cuggcuacgg ccacaccccc cgggucagug acaacccccc aucccgauau agaagaggua   5880
ggccucgggc gggaggguga gauccccuuc uaugggaggg cgauuccccu auccugcauc   5940
aagggaggga gacaccugau uuucugccac ucaaagaaaa agugugacga gcucgcggcg   6000
gcccuucggg gcaugggcuu gaaugccgug gcauacuaua gaggguugga cgucuccaua   6060
auaccagcuc agggagaugu gguggucguc gccaccgacg cccucaugac gggguacacu   6120
ggagacuuug acuccgugau cgacugcaau guagcgguca cccaagcugu cgacuucagc   6180
cuggacccca ccuucacuau aaccacacag acugucccac aagacgcugu cucacgcagu   6240
cagcgccgcg ggcgcacagg uagaggaaga cagggcacuu auagguaugu uuccacuggu   6300
gaacgagccu caggaauguu ugacagugua gugcuuugug agugcuacga cgcaggggcu   6360
gcgugguacg aucucacacc agcggagacc accgucaggc uuagagcgua uuucaacacg   6420
```

-continued

```
cccggccuac ccguguguca agaccaucuu gaauuuuggg aggcaguuuu caccggccuc   6480
acacacauag acgcccacuu ccucucccaa acaaagcaag cgggggagaa cuucgcguac   6540
cuaguagccu accaagcuac ggugugcgcc agagccaagg ccccuccccc guccugggac   6600
gccaugugga agugccuggc ccgacucaag ccuacgcuug cgggccccac accucuccug   6660
uaccguuugg gcccuauuac caaugagguc acccucacac acccugggac gaaguacauc   6720
gccacaugca ugcaagcuga ccuugagguc augaccagca cgugggucuu agcuggagga   6780
guccuggcag ccgucgccgc auauugccug gcgacuggau gcguuuccau caucggccgc   6840
uugcacguca accagcgagu cgucguugcg ccggauaagg agguccugua ugaggcuuuu   6900
gaugagaugg aggaaugcgc cucuagggcg gcucucaucg aagaggggca gcggauagcc   6960
gagauguuga aguccaagau ccaaggcuug cugcagcagg ccucuaagca ggcccaggac   7020
auacaacccg cuaugcaggc uucauggccc aaaguggaac aauuuugggc cagacacaug   7080
uggaacuuca uuagcggcau ccaauaccuc gcaggauugu caacacugcc agggaacccc   7140
gcgguggcuu ccaugauggc auucagugcc gcccucacca guccguuguc gaccaguacc   7200
accauccuuc ucaacaucau gggaggcugg uuagcguccc agaucgcacc acccgcgggg   7260
gccaccggcu uugucgucag uggccuggug ggggcugccg ugggcagcau aggccugggu   7320
aaggugcugg uggacauccu ggcaggauau ggugcgggca uuucgggggc ccucgucgca   7380
uucaagauca ugucuggcga gaagcccucu auggaagaug ucaucaaucu acugccuggg   7440
auccugucuc cgggagcccu gguggugggg gucaucugcg cggccauucu gcgccgccac   7500
gugggaccgg gggagggcgc gguccaaugg augaacaggc uuauugccuu ugcuuccaga   7560
ggaaaccacg ucgccccuac ucacuacgug acggagucgg augcgucgca gcgugugacc   7620
caacuacuug gcucucuuac uauaaccagc cuacucagaa gacuccacaa uuggauaacu   7680
gaggacugcc ccaucccaug cuccggaucc uggcuccgcg acgugugga cuggguuugc   7740
accaucuuga cagacuucaa aaauuggcug accucuaaau uguuccccaa gcugcccggc   7800
cuccccuuca ucucuuguca aaaggggguac aagggugugu gggccggcac uggcaucaug   7860
accacgcgcu gcccuugcgg cgccaacauc ucuggcaaug uccgccuggg cucuaugagg   7920
aucacagggc cuaaaaccug caugaacacc uggcagggga ccuuuccuau caauugcuac   7980
acggagggcc agugcgcgcc gaaacccccc acgaacuaca agaccgccau cuggagggug   8040
gcggccucgg aguacgcgga ggugacgcag caugggucgu acuccuaugu aacaggacug   8100
accacugaca aucugaaaau uccuugccaa cuaccuucuc cagaguuuuu cuccugggug   8160
gacggugugc agauccauag guuugcaccc acaccaaagc cguuuuuccg ggaugagguc   8220
ucguucugcg uugggcuuaa uuccuaugcu gucggguccc agcuucccug ugaaccugag   8280
cccgacgcag acguauugag guccaugcua acagauccgc cccacaucac ggcggagacu   8340
gcggcgcggc gcuuggcacg ggaucaccu ccaucugagg cgagcuccuc agugagccag   8400
cuaucagcac cgucgcugcg ggccaccugc accacccaca gcaacaccua ugacguggac   8460
auggucgaug ccaaccugcu cauggagggc gguguggcuc agacagagcc ugaguccagg   8520
gugcccguuc uggacuuucu cgagccaaug gccgaggaag agagcgaccu ugagcccuca   8580
auaccaucgg agugcaugcu ccccaggagc ggguuuccac gggccuuacc ggcuugggca   8640
cggccugacu acaacccgcc gcucguggaa ucguggagga ggccagauua ccaaccgccc   8700
accguugcug guugugcucu cccccccccc aagaaggccc cgacgccucc cccaaggaga   8760
cgccggacag ugggucugag cgagagcacc auaucagaag cccuccagca acuggccauc   8820
```

-continued

```
aagaccuuug gccagccccc cucgagcggu gaugcaggcu cguccacggg ggcgggcgcc   8880
gccgaauccg gcgguccgac guccccuggu gagccggccc ccucagagac agguuccgcc   8940
uccucuaugc cccccucga gggggagccu ggagauccgg accuggaguc ugaucaggua   9000
gagcuucaac cucccccca gggggggggg guagcucccg guucgggcuc ggggucuugg   9060
ucuacuugcu ccgaggagga cgauaccacc gugugcugcu ccaugucaua cuccuggacc   9120
ggggcucuaa uaacucccug uagccccgaa gaggaaaagu ugccaaucaa cccuuugagu   9180
aacucgcugu ugcgauacca uaacaaggug uacuguacaa caucaaagag cgccucacag   9240
agggcuaaaa agguaacuuu ugacaggacg caagugcucg acgcccauua ugacucaguc   9300
uuaaaggaca ucaagcuagc ggcuuccaag gucagcgcaa ggcuccucac cuuggaggag   9360
gcgugccagu ugacuccacc ccauucugca agauccaagu auggauucgg ggccaaggag   9420
guccgcagcu uguccgggag ggccguuaac cacaucaagu ccguguggaa ggaccuccug   9480
gaagacccac aaacaccaau ucccacaacc aucauggcca aaaaugaggu guucugcgug   9540
gaccccgcca agggggguaa gaaaccagcu cgccucaucg uuuacccuga ccucggcguc   9600
cgggucugcg agaaaauggc ccucuaugac auuacacaaa agcuuccuca ggcgguaaug   9660
ggagcuuccu auggcuucca guacuccccu gcccaacggg uggaguaucu cuugaaagca   9720
ugggcggaaa agaaggaccc caugggguuu ucguaugaua cccgaugcuu cgacucaacc   9780
gucacugaga gagacaucag gaccgaggag uccauauacc aggccugcuc ccugcccgag   9840
gaggcccgca cugccauaca cucgcugacu gagagacuuu acguaggagg gcccauguuc   9900
aacagcaagg gucaaaccug cgguuacaga cguugccgcg ccagcggggu gcuaaccacu   9960
agcaugggua acaccaucac augcuaugug aaagcccuag cggccugcaa ggcugcgggg  10020
auaguugcgc ccacaaugcu gguaugcggc gaugaccuag uagucaucuc agaaagccag  10080
gggacugagg aggacgagcg gaaccugaga gccuucacgg aggccaugac cagguacucu  10140
gccccuccug gugauccccc cagaccggaa uaugaccugg agcuaauaac auccuguucc  10200
ucaaaugugu cuguggcguu gggcccgcgg ggccgccgca gauacuaccu gaccagagac  10260
ccaaccacuc cacucgcccg ggcugccugg gaaacaguua gacacucccc uaucaauuca  10320
uggcugggaa acaucaucca guaugcucca accauauggg uucgcauggu ccuaaugaca  10380
cacuucuucu ccauucucau gguccaagac acccuggacc agaaccucaa cuuugagaug  10440
uauggaucag uauacuccgu gaauccuuug gaccuuccag ccauaauuga gagguuacac  10500
gggcuugacg ccuuuucuau gcacacauac ucucaccacg aacugacgcg gguggcuuca  10560
gcccucagaa aacuuggggc gccacccuc agggugugga agagucgggc ucgcgcaguc  10620
agggcguccc ucaucucccg uggagggaaa gcggccguuu gcggccgaua ucucuucaau  10680
ugggcggugu agaccaagcu caaacucacu ccauugccgg aggcgcgccu acuggacuua  10740
uccaguuggu ucaccgucgg cgccggcggg ggcgacauuu uucacagcgu gucgcgcgcc  10800
cgaccccgcu cauuacucuu cggccuacuc cuacuuuucg uaggggguagg ccucuuccua  10860
cuccccgcuc gguagagcgg cacacacuag guacacucca uagcuaacug uuccuuuuuu  10920
uuuuuuuuuu uuuuuuuuuu uuuuuuuuuu uuuuuuucuu uuuuuuuuuu uucccucuuu  10980
cuucccuucu caucuuauuc uacuuucuuu cuugguggcu ccaucuuagc ccuagucacg  11040
gcuagcugug aaagguccgu gagccgcaug acugcagaga gugccguaac uggucucucu  11100
gcagaucaug u                                                       11111
```

<210> SEQ ID NO 14
<211> LENGTH: 11111
<212> TYPE: RNA
<213> ORGANISM: Artificial Sequence
<220> FEATURE:
<223> OTHER INFORMATION: full-length Hepatitis C virus genomic RNA derived from JFH-1 clone, wherein an amino acid motif GDD has been mutated into GND

<400> SEQUENCE: 14

```
accugccccu aauaggggcg acacuccgcc augaaucacu ccccugugag gaacuacugu     60

cuucacgcag aaagcgccua gccauggcgu uaguaugagu gucguacagc cuccaggccc    120

cccccucccg ggagagccau aguggucugc ggaaccggug aguacaccgg aauugccggg    180

aagacugggu ccuuucuugg auaaacccac ucuaugcccg gccauuuggg cgugcccccg    240

caagacugcu agccgaguag cguuggguug cgaaaggccu uguggguacug ccugauaggg    300

cgcuugcgag ugccccggga ggucucguag accgugcacc augagcacaa auccuaaacc    360

ucaaagaaaa accaaaagaa acaccaaccg ucgcccaaug auugaacaag auggauugca    420

cgcagguucu ccggccgcuu ggguggagag gcuauucggc uaugacuggg cacaacagac    480

aaucggcugc ucugaugccg ccguguuccg gcugucagcg caggggcgcc cgguucuuuu    540

ugucaagacc gaccuguccg gugcccugaa ugaacugcag gacgaggcag cgcggcuauc    600

guggcuggcc acgacgggcg uuccuugcgc agcugugcuc gacguuguca cugaagcggg    660

aagggacugg cugcuauugg gcgaagugcc ggggcaggau cuccugucau cucaccuugc    720

uccugccgag aaaguaucca ucauggcuga ugcaaugcgg cggcugcaua cgcuugaucc    780

ggcuaccugc ccauucgacc accaagcgaa acaucgcauc gagcgagcac guacucggau    840

ggaagccggu cuugucgauc aggaugaucu ggacgaagag caucaggggc ucgcgccagc    900

cgaacuguuc gccaggcuca aggcgcgcau gcccgacggc gaggaucucg ucgugaccca    960

uggcgaugcc ugcuugccga auaucauggu ggaaaauggc cgcuuuucug gauucaucga   1020

cuguggccgg cugggugugg cggaccgcua ucaggacaua gcguuggcua cccgugauau   1080

ugcugaagag cuuggcggcg aaugggcuga ccgcuuccuc gugcuuuacg guaucgccgc   1140

ucccgauucg cagcgcaucg ccuucuaucg ccuucuugac gaguucuucu gaguuuaaac   1200

ccucucccuc cccccccccu aacguuacug gccgaagccg cuuggaauaa ggccggugug   1260

cguuugucua uauguuauuu uccaccauau ugccgucuuu uggcaaugug agggcccgga   1320

aaccuggccc ugucuucuug acgagcauuc cuaggggucu uuccccucuc gccaaaggaa   1380

ugcaaggucu guugaauguc gugaaggaag caguuccucu ggaagcuucu ugaagacaaa   1440

caacgucugu agcgacccuu ugcaggcagc ggaacccccc accuggcgac aggugccucu   1500

gcggccaaaa gccacgugua uaagauacac cugcaaaggc ggcacaaccc cagugccacg   1560

uugugaguug gauaguugug gaaagaguca aauggcucuc cucaagcgua uucaacaagg   1620

ggcugaagga ugcccagaag guaccccauu guaugggauc ugaucugggg ccucggugca   1680

caugcuuuac auguguuuag ucgagguuaa aaaaacgucu aggccccccg aaccacgggg   1740

acgugguuuu ccuuugaaaa acacgaugau accaugagca caaauccuaa accucaaaga   1800

aaaaccaaaa gaaacaccaa ccgucgccca gaagacguua aguucccggg cggcggccag   1860

aucguuggcg gaguauacuu guugccgcgc aggggcccca gguugggugu gcgcacgaca   1920

aggaaaacuu cggagcgguc ccagccacgu gggagacgcc agcccauccc caaagaucgg   1980

cgcuccacug gcaaggccug ggaaaacca ggucgccccu ggccccuaua ugggaaugag    2040

ggacucggcu gggcaggaug gcuccugucc ccccgaggcu cucgccccuc cuggggcccc   2100
```

-continued

```
acugaccccc ggcauagguc gcgcaacgug gguaaaguca ucgacacccu aacguguggc   2160
uuugccgacc ucaugggua  cauccccguc guaggcgccc cgcuuagugg cgccgccaga   2220
gcugucgcgc acggcgugag aguccuggag gacgggguua auuaugcaac agggaaccua   2280
cccgguuucc ccuuuucuau cuucuugcug gcccuguugu ccugcaucac cguuccgguc   2340
ucugcugccc aggugaagaa uaccaguagc agcuacaugg ugaccaauga cugcuccaau   2400
gacagcauca cuuggcagcu cgaggcugcg guucuccacg uccccgggug cgucccgugc   2460
gagagagugg ggaauacguc acgguguugg gugccagucu cgccaaacau ggcugugcgg   2520
cagcccggug cccucacgca gggucugcgg acgcacaucg auaugguugu gauguccgcc   2580
accuucugcu cugcucucua cgugggggac cucuguggcg gggugaugcu cgcggcccag   2640
guguucaucg ucucgccgca guaccacugg uuugugcaag aaugcaauug cuccaucuac   2700
ccuggcacca ucacuggaca ccgcauggca ugggacauga ugaugaacug gucgcccacg   2760
gccaccauga uccuggcgua cgugaugcgc guccccgagg ucaucauaga caucguuagc   2820
ggggcucacu ggggcgucau guucggcuug gccuacuucu cuaugcaggg agcgugggcg   2880
aaggucauug ucauccuucu gcuggccgcu ggggguggacg cgggcaccac caccguugga   2940
ggcgcuguug cacguuccac caacgugauu gccggcgugu ucagccaugg cccucagcag   3000
aacauucagc ucauuaacac caacggcagu uggcacauca accguacugc cuugaauugc   3060
aaugacuccu ugaacaccgg cuuucucgcg gccuuguucu acaccaaccg cuuuaacucg   3120
ucagggguguc cagggcgccu guccgccugc cgcaacaucg aggcuuuccg gauagggugg   3180
ggcacccuac aguacgagga uaaugucacc aauccagagg auaugaggcc guacugcugg   3240
cacuaccccc caaagccgug uggcguaguc cccgcgaggu cugugugugg cccaguguac   3300
uguuucaccc ccagcccggu aguagugggc acgaccgaca gacguggagu gcccaccuac   3360
acauggggag agaaugagac agaugucuuc cuacugaaca gcacccgacc gccgcagggc   3420
ucaugguucg gcugcacgug gaugaacucc acugguuuca ccaagacuug uggcgcgcca   3480
ccuugccgca ccagagcuga cuucaacgcc agcacggacu uguugugccc uacggauugu   3540
uuuaggaagc auccugaugc cacuuauauu aaguguggguu cugggcccug gcucacacca   3600
aagugccugg uccacuaccc uuacagacuc uggcauuacc ccugcacagu caauuuuacc   3660
aucuucaaga uaagaaugua uguagggggg guugagcaca ggcucacggc cgcaugcaac   3720
uucacucgug gggaucgcug cgacuuggag gacagggaca ggagucagcu gucuccucug   3780
uugcacucua ccacggaaug ggccauccug cccugcaccu acucagacuu acccgcuuug   3840
ucaacugguc uucuccaccu ucaccagaac aucguggacg uacaauacau guauggccuc   3900
ucaccugcua ucacaaaaua cgucguucga ugggagugggg ugguacucuu auuccugcuc   3960
uuagcggacg ccagagucug cgccugcuug uggaugcuca ucuuguuggg ccaggccgaa   4020
gcagcauugg agaaguuggu cgucuugcac gcugcgagug cggcuaacug ccauggccuc   4080
cuauauuuug ccaucuucuu cguggcagcu uggcacauca ggggucgggu gguccccuug   4140
accaccuauu gccucacugg ccuauggccc uucugccuac ugcucauggc acugccccgg   4200
caggcuuaug ccuaugacgc accugugcac ggacagauag gcguggguuu guugauauug   4260
aucacccucu ucacacucac cccgggguau aagacccucc ucggccagug ucugugguggg   4320
uugugcuauc ucccugaccu gggggaagcc augauucagg agugggguacc acccaugcag   4380
gugcgcggcg gccgcgaugg caucgcgugg gccgucacua uauucugccc ggguguggug   4440
uuugacauua ccaaauggcu uuuggcguug cuugggccug cuuaccucuu aagggccgcu   4500
```

-continued

```
uugacacaug ugccguacuu cgucagagcu cacgcucuga uaaggguaug cgcuuuggug   4560
aagcagcucg cggggggguag guauguucag guggcgcuau uggcccuugg cagguggacu   4620
ggcaccuaca ucuaugacca ccucacaccu augucggacu gggccgcuag cggccugcgc   4680
gacuuagcgg ucgccgugga acccaucauc uucaguccga uggagaagaa ggucaucguc   4740
uggggagcgg agacggcugc auguggggac auucuacaug gacuucccgu guccgcccga   4800
cucggccagg agauccuccu cggcccagcu gauggcuaca ccuccaaggg guggaagcuc   4860
cuugcuccca ucacugcuua ugcccagcaa acacgaggcc uccugggcgc cauaguggug   4920
aguaugacgg ggcgugacag gacagaacag gccggggaag uccaaauccu guccacaguc   4980
ucucaguccu uccucggaac aaccaucucg gggguuuugu ggacuguuua ccacggagcu   5040
ggcaacaaga cucuagccgg cuuacggggu ccggucacgc agauguacuc gagugcugag   5100
ggggacuugg uaggcuggcc cagcccccu gggaccaagu cuuuggagcc gugcaagugu   5160
ggagccgucg accuauaucu ggucacgcgg aacgcugaug ucaucccggc ucggagacgc   5220
ggggacaagc ggggagcauu gcucuccccg agacccauuu cgaccuugaa gggguccucg   5280
ggggggccgg ugcucugccc uaggggccac gucguugggc ucuuccgagc agcugugugc   5340
ucucggggcg uggccaaauc caucgauuuc auccccguug agacacucga cguuguuaca   5400
aggucuccca cuuucaguga caacagcacg ccaccggcug ugccccagac cuaucagguc   5460
ggguacuugc augcuccaac uggcagugga aagagcacca agguccugu cgcguaugcc   5520
gcccaggggu acaaaguacu agugcuuaac cccucgguag cugccacccu gggguuuggg   5580
gcguaccuau ccaaggcaca uggcaucaau cccaacauua ggacuggagu caggaccgug   5640
augaccgggg aggccaucac guacuccaca uauggcaaau uucucgccga ugggggcugc   5700
gcuagcggcg ccuaugacau caucauaugc gaugaaugcc acgcugugga ugcuaccucc   5760
auucucggca ucggaacggu ccuugaucaa gcagagacag ccggggucag acuaacugug   5820
cuggcuacgg ccacaccccc cggggucagug acaaccccc aucccgauau agaagaggua   5880
ggccucgggc gggaggguga gauccccuuc uaugggaggg cgauuccccu auccugcauc   5940
aagggaggga gacaccugau uuucugccac ucaaagaaaa agugugacga gcucgcggcg   6000
gcccuucggg gcaugggcuu gaaugccgug gcauacuaua gaggguugga cgucuccaua   6060
auaccagcuc agggagaugu gguggucguc gccaccgacg cccucaugac gggguacacu   6120
ggagacuuug acuccgugau cgacugcaau guagcgguca cccaagcugu cgacuucagc   6180
cuggacccca ccuucacuau aaccacacag acugucccac aagacgcugu cucacgcagu   6240
cagcgccgcg ggcgcacagg uagaggaaga cagggcacuu auagguaugu uuccacuggu   6300
gaacgagccu caggaauguu ugacagugua gugcuuugug agugcuacga cgcaggggcu   6360
gcgugguacg aucucacacc agcggagacc accgucaggc uuagagcgua uuucaacacg   6420
cccggccuac ccguguguca agaccaucuu gaauuuuggg aggcaguuuu caccggccuc   6480
acacacauag acgcccacuu ccucucccaa acaaagcaag cgggggagaa cuucgcguac   6540
cuaguagccu accaagcuac ggugugcgcc agagccaagg cccucccccc guccugggac   6600
gccaugugga agugccuggc ccgacucaag ccuacgcuug cgggccccac accucuccug   6660
uaccguuugg gcccuauuac caaugagguc acccucacac acccugggac gaaguacauc   6720
gccacaugca ugcaagcuga ccuugagguc augaccagca cgugggguccu agcuggagga   6780
guccuggcag ccgucgccgc auauugccug gcgacuggau gcguuuccau caucggccgc   6840
uugcacguca accagcgagu cgucguugcg ccggauaagg agguccugua ugaggcuuuu   6900
```

-continued

```
gaugagaugg aggaaugcgc cucuagggcg gcucucaucg aagaggggca gcggauagcc   6960
gagauguuga aguccaagau ccaaggcuug cugcagcagg ccucuaagca ggcccaggac   7020
auacaacccg cuaugcaggc uucauggccc aaaguggaac aauuuugggc cagacacaug   7080
uggaacuuca uuagcggcau ccaauaccuc gcaggauugu caacacugcc agggaacccc   7140
gcgguggcuu ccaugauggc auucagugcc gcccucacca guccguuguc gaccaguacc   7200
accauccuuc ucaacaucau gggaggcugg uuagcguccc agaucgcacc acccgcgggg   7260
gccaccggcu uugucgucag uggccuggug gggcugccg ugggcagcau aggccugggu   7320
aaggugcugg uggacauccu ggcaggauau ggugcgggca uuucgggggc ccucgucgca   7380
uucaagauca ugucuggcga gaagcccucu auggaagaug ucaucaaucu acugccuggg   7440
auccugucuc cgggagcccu gguggugggg gucaucugcg cggccauucu gcgccgccac   7500
gugggaccgg gggagggcgc gguccaaugg augaacaggc uuauugccuu ugcuuccaga   7560
ggaaaccacg ucgccccuac ucacuacgug acggagucgg augcgucgca gcgugugacc   7620
caacuacuug gcucucuuac uauaaccagc cuacucagaa gacuccacaa uuggauaacu   7680
gaggacugcc ccaucccaug cuccggaucc uggcuccgcg acguguggga cuggguuugc   7740
accaucuuga cagacuucaa aaauuggcug accucuaaau uguuccccaa gcugcccggc   7800
cuccccuuca ucucuuguca aaaggggua aagggugugu gggccggcac uggcaucaug   7860
accacgcgcu gcccuugcgg cgccaacauc ucuggcaaug uccgccuggg cucuaugagg   7920
aucacagggc cuaaaaccug caugaacacc uggcagggga ccuuuccuau caauugcuac   7980
acggagggcc agugcgcgcc gaaacccccc acgaacuaca agaccgccau cuggagggug   8040
gcggccucgg aguacgcgga ggugacgcag caugggucgu acuccuaugu aacaggacug   8100
accacugaca aucugaaaau ucccuugcca cuaccuucuc cagaguuuuu cuccugggug   8160
gacggugugc agauccauag guuugcaccc acaccaaagc cguuuuuccg ggaugagguc   8220
ucguucugcg uugggcuuaa uuccuaugcu gucgggucccc agcuucccug ugaaccugag   8280
cccgacgcag acguauugag guccaugcua acagauccgc cccacaucac ggcggagacu   8340
gcggcgcggc gcuuggcacg gggaucaccu ccaucugagg cgagcuccuc agugagccag   8400
cuaucagcac cgucgcugcg ggccaccugc accacccaca gcaacaccua ugacguggac   8460
auggucgaug ccaaccugcu cauggagggc ggguguggcuc agacagagcc ugaguccagg   8520
gugcccguuc uggacuuucu cgagccaaug gccgaggaag agagcgaccu ugagcccuca   8580
auaccaucgg agugcaugcu ccccaggagc ggguuuccac gggccuuacc ggcuugggca   8640
cggccugacu acaacccgcc gcucgugga ucguggagga ggccagauua ccaaccgccc   8700
accguugcug guugugcucu cccccccccc aagaaggccc cgacgccucc cccaaggaga   8760
cgccggacag ugggucugag cgagagcacc auaucagaag cccuccagca acuggccauc   8820
aagaccuuug gccagccccc cucgagcggu gaugcaggcu cguccacggg ggcgggcgcc   8880
gccgaauccg gcgguccgac guccccuggu gagccggccc ccucagagac agguuccgcc   8940
uccucuaugc ccccccucga gggggagccu ggagauccgg accuggaguc ugaucaggua   9000
gagcuucaac cuccccccca gggggggggg guagcucccg guucgggcuc ggggucuugg   9060
ucuacuugcu ccgaggagga cgauaccacc gugugcugcu ccaugucaua cuccuggacc   9120
ggggcucuaa uaacucccug uagccccgaa gaggaaaagu ugccaaucaa cccuuugagu   9180
aacucgcugu ugcgauacca uaacaaggug uacuguacaa caucaaagag cgccucacag   9240
agggcuaaaa agguaacuuu ugacaggacg caagugcucg acgcccauua ugacucaguc   9300
```

uuaaaggaca ucaagcuagc ggcuuccaag gucagcgcaa ggcuccucac cuuggaggag 9360
gcgugccagu ugacuccacc ccauucugca agauccaagu auggauucgg ggccaaggag 9420
guccgcagcu uguccgggag ggccguuaac cacaucaagu ccguguggaa ggaccuccug 9480
gaagacccac aaacaccaau ucccacaacc aucauggcca aaaaugaggu guucugcgug 9540
gaccccgcca agggggguaa gaaaccagcu cgccucaucg uuuacccuga ccucggcguc 9600
cgggucugcg agaaaauggc ccucuaugac auuacacaaa agcuuccuca ggcgguaaug 9660
ggagcuuccu auggcuucca guacuccccu gcccaacggg uggaguaucu cuugaaagca 9720
ugggcggaaa agaaggaccc caugggguuu ucguaugaua cccgaugcuu cgacucaacc 9780
gucacugaga gagacaucag gaccgaggag uccauauacc aggccugcuc ccugcccgag 9840
gaggcccgca cugccauaca cucgcugacu gagagacuuu acguaggagg gcccauguuc 9900
aacagcaagg gucaaaccug cgguuacaga cguugccgcg ccagcggggu gcuaaccacu 9960
agcaugggua acaccaucac augcuaugug aaagcccuag cggccugcaa ggcugcgggg 10020
auaguugcgc ccacaaugcu gguaugcggc aaugaccuag uagucaucuc agaaagccag 10080
gggacugagg aggacgagcg gaaccugaga gccuucacgg aggccaugac cagguacucu 10140
gccccuccug gugauccccc cagaccggaa uaugaccugg agcuaauaac auccuguucc 10200
ucaaaugugu cuguggcguu gggcccgcgg ggccgccgca gauacuaccu gaccagagac 10260
ccaaccacuc cacucgcccg ggcugccugg gaaacaguua gacacucccc uaucaauuca 10320
uggcugggaa acaucaucca guaugcucca accauauggg uucgcauggu ccuaaugaca 10380
cacuucuucu ccauucucau gguccaagac acccuggacc agaaccucaa cuuugagaug 10440
uauggaucag uauacuccgu gaauccuuug gaccuuccag ccauaauuga gagguuacac 10500
gggcuugacg ccuuuucuau gcacacauac ucucaccacg aacugacgcg gguggcuuca 10560
gcccucagaa aacuuggggc gccacccuc agggugugga agagucgggc ucgcgcaguc 10620
agggcguccc ucaucucccg uggagggaaa gcggccguuu gcggccgaua ucucuucaau 10680 ugggcggguga agaccaagcu caaacucacu ccauugccgg aggcgcgccu acuggacuua 10740
uccaguuggu ucaccgucgg cgccggcggg ggcgacauuu uucacagcgu gucgcgcgcc 10800
cgaccccgcu cauuacucuu cggccuacuc cuacuuuucg uagggguagg ccucuuccua 10860
cuccccgcuc gguagagcgg cacacacuag guacacucca uagcuaacug uuccuuuuuu 10920
uuuuuuuuuu uuuuuuuuuu uuuuuuuuuu uuuuuuucuu uuuuuuuuuu uucccucuuu 10980
cuucccuucu caucuuauuc uacuuucuuu cuugguggcu ccaucuuagc ccuagucacg 11040
gcuagcugug aaagguccgu gagccgcaug acugcagaga gugccguaac uggucucucu 11100
gcagaucaug u 11111

<210> SEQ ID NO 15
<211> LENGTH: 9678
<212> TYPE: RNA
<213> ORGANISM: Artificial Sequence
<220> FEATURE:
<223> OTHER INFORMATION: replicon RNA comprising full-length Hepatitis C virus genomic RNA derived from JFH-1 clone, wherein an amino acid motif GDD has been mutated into GND

<400> SEQUENCE: 15 accugcccu aauaggggcg acacuccgcc augaaucacu ccccugugag gaacuacugu 60
cuucacgcag aaagcgccua gccauggcgu uaguaugagu gucguacagc cuccaggccc 120
cccccucccg ggagagccau aguggucugc ggaaccggug aguacaccgg aauugccggg 180

-continued

```
aagacugggu ccuuucuugg auaaacccac ucuaugcccg gccauuuggg cgugcccccg    240
caagacugcu agccgaguag cguuggguug cgaaaggccu ugugguacug ccugauaggg    300
cgcuugcgag ugccccggga ggucucguag accgugcacc augagcacaa auccuaaacc    360
ucaaagaaaa accaaaagaa acaccaaccg ucgcccagaa gacguuaagu ucccgggcgg    420
cggccagauc guuggcggag uauacuuguu gccgcgcagg ggccccaggu ugggugugcg    480
cacgacaagg aaaacuucgg agcgguccca gccacguggg agacgccagc ccauccccaa    540
agaucggcgc uccacuggca aggccugggg aaaaccaggu cgccccuggc cccuauaugg    600
gaaugaggga cucggcuggg caggauggcu ccuguccccc cgaggcucuc gccccuccug    660
gggccccacu gacccccggc auaggucgcg caacgugggu aaagucaucg acacccuaac    720
guguggcuuu gccgaccuca uggggguacau ccccgucgua ggcgccccgc uuaguggcgc    780
cgccagagcu gucgcgcacg gcgugagagu ccuggaggac gggguuaauu augcaacagg    840
gaaccuaccc gguuuccccu uuucuaucuu cuugcuggcc cuguuguccu gcaucaccgu    900
uccggucucu gcugcccagg ugaagaauac caguagcagc uacaugguga ccaaugacug    960
cuccaaugac agcaucacuu ggcagcucga ggcugcgguu cuccacgucc ccgggugcgu   1020
cccgugcgag agagugggga auacgucacg guguugggug ccagucucgc caaacauggc   1080
ugugcggcag cccggugccc ucacgcaggg ucugcggacg cacaucgaua ugguugugau   1140
guccgccacc uucugcucug cucucuacgu gggggaccuc uguggcgggg ugaugcucgc   1200
ggcccaggug uucaucgucu cgccgcagua ccacugguuu gugcaagaau gcaauugcuc   1260
caucuacccu ggcaccauca cuggacaccg cauggcaugg gacaugauga ugaacugguc   1320
gcccacggcc accaugaucc uggcguacgu gaugcgcguc cccgagguca ucauagacau   1380
cguuagcggg gcucacuggg gcgucauguu cggcuuggcc uacuucucua ugcagggagc   1440
gugggcgaag gucauuguca uccuucugcu ggccgcuggg guggacgcgg gcaccaccac   1500
cguuggaggc gcuguugcac guuccaccaa cgugauugcc ggcguguuca gccauggccc   1560
ucagcagaac auucagcuca uuaacaccaa cggcaguugg cacaucaacc guacugccuu   1620
gaauugcaau gacuccuuga acaccggcuu ucucgcggcc uuguucuaca ccaaccgcuu   1680
uaacucguca ggguguccag ggcgccuguc cgccugccgc aacaucgagg cuuuccggau   1740
agggugggc acccuacagu acgaggauaa ugucaccaau ccagaggaua ugaggccgua   1800
cugcuggcac uacccccaa agccgugugg cguagucccc gcgaggucug uguguggccc   1860
aguguacugu uucacccca gcccgguagu aguggcacg accgacagac guggagugcc   1920
caccuacaca uggggagaga augagacaga ugucuuccua cugaacagca cccgaccgcc   1980
gcagggcuca ugguucggcu gcacguggau gaacuccacu gguuucacca agacuugugg   2040
cgcgccaccu ugccgcacca gagcugacuu caacgccagc acggacuugu ugugcccuac   2100
ggauuguuuu aggaagcauc cugaugccac uuauauuaag ugugguucug ggcccuggcu   2160
cacaccaaag ugccuggucc acuacccuua cagacucugg cauuaccccu gcacagucaa   2220
uuuuaccauc uucaagauaa gaauguaugu agggggggguu gagcacaggc ucacggccgc   2280
augcaacuuc acucguggg aucgcugcga cuuggaggac agggacagga gucagcuguc   2340
uccucuguug cacucuacca cggaaugggc cauccugccc ugcaccuacu cagacuuacc   2400
cgcuuuguca acuggucuuc uccaccuuca ccagaacauc guggacguac aauacaugua   2460
uggccucuca ccugcuauca caaaauacgu cguucgaugg gagugggugg uacucuuauu   2520
ccugcucuua gcggacgcca gagucugcgc cugcuugugg augcucaucu uguugggcca   2580
```

-continued ggccgaagca gcauuggaga aguuggucgu cuugcacgcu gcgagugcgg cuaacugcca 2640
uggccuccua uauuuugcca ucuucuucgu ggcagcuugg cacaucaggg gucgggugu 2700
ccccuugacc accuauugcc ucacuggccu auggcccuuc ugccuacugc ucauggcacu 2760
gccccggcag gcuuaugccu augacgcacc ugugcacgga cagauaggcg ugggguuguu 2820
gauauugauc acccucuuca cacucacccc gggguauaag acccuccucg gccagugucu 2880
gugguggug ugcuaucucc ugacccuggg ggaagccaug auucaggagu ggguaccacc 2940
caugcaggug cgcggcggcc gcgauggcau cgcgugggcc gucacuauau ucugcccggg 3000
uguggugguu gacauuacca aauggcuuuu ggcguugcuu gggccugcuu accucuuaag 3060
ggccgcuuug acacaugugc cguacuucgu cagagcucac gcucugauaa ggguaugcgc 3120
uuuggugaag cagcucgcgg gggguaggua uguucaggug gcgcuauugg cccuuggcag 3180
guggacuggc accuacaucu augaccaccu cacaccuaug ucggacuggg ccgcuagcgg 3240
ccugcgcgac uuagcggucg ccguggaacc caucaucuuc aguccgaugg agaagaaggu 3300
caucgucugg ggagcggaga cggcugcaug uggggacauu cuacauggac uucccguguc 3360
cgcccgacuc ggccaggaga uccuccucgg cccagcugau ggcuacaccu ccaaggggug 3420
gaagcuccuu gcucccauca cugcuuaugc ccagcaaaca cgaggccucc ugggcgccau 3480
aguggugagu augacggggc gugacaggac agaacaggcc ggggaagucc aaauccuguc 3540
cacagucucu caguccuucc ucggaacaac caucucgggg guuuugugga cuguuuacca 3600
cggagcuggc aacaagacuc uagccggcuu acgggguccg gucacgcaga uguacucgag 3660
ugcugagggg gacuugguag gcuggcccag ccccccuggg accaagucuu uggagccgug 3720
caagugugga gccgucgacc uauaucuggu cacgcggaac gcugauguca ucccggcucg 3780
gagacgcggg gacaagcggg gagcauugcu cuccccgaga cccauuucga ccuugaaggg 3840
guccucgggg gggccggugc ucugcccuag gggccacguc guugggcucu uccgagcagc 3900
ugugugcucu cggggcgugg ccaaauccau cgauuucauc cccguugaga cacucgacgu 3960
uguuacaagg ucucccacuu ucagugacaa cagcacgcca ccggcugugc cccagaccua 4020
ucaggucggg uacuugcaug cuccaacugg caguggaaag agcaccaagg ucccugucgc 4080
guaugccgcc caggggguaca aaguacuagu gcuuaacccc ucgguagcug ccacccuggg 4140
guuuggggcg uaccuaucca aggcacaugg caucaauccc aacauuagga cuggagucag 4200
gaccgugaug accggggagg ccaucacgua cuccacauau ggcaaauuuc ucgccgaugg 4260
gggcugcgcu agcggcgccu augacaucau cauaugcgau gaaugccacg cuguggaugc 4320
uaccuccauu cucggcaucg gaacggaccu ugaucaagca gagacagccg gggucagacu 4380
aacugugcug gcuacggcca caccccccgg gucagugaca accccccauc ccgauauaga 4440
agagguaggc cucgggcggg agggugagau ccccuucuau gggagggcga uuccccuauc 4500
cugcaucaag ggagggagac accugauuuu cugccacuca aagaaaaagu gugacgagcu 4560
cgcggcggcc cuucggggca ugggcuugaa ugccguggca uacuauagag gguuggacgu 4620
cuccauaaua ccagcucagg gagauguggu ggucgucgcc accgacgccc ucaugacggg 4680
guacacugga gacuuugacu ccgugaucga cugcaaugua gcggucaccc aagcugucga 4740
cuucagccug gaccccaccu ucacuauaac cacacagacu gucccacaag acgcugucuc 4800
acgcagucag cgccgcgggc gcacagguag aggaagacag ggcacuuaua gguauguuuc 4860
cacuggugaa cgagccucag gaauguuuga caguguagug cuuugugagu gcuacgacgc 4920
aggggcugcg ugguacgauc ucacaccagc ggagaccacc gucaggcuua gagcguauuu 4980

-continued

```
caacacgccc ggccuacccg ugugucaaga ccaucuugaa uuuugggagg caguuuucac   5040
cggccucaca cacauagacg cccacuuccu cucccaaaca aagcaagcgg gggagaacuu   5100
cgcguaccua guagccuacc aagcuacggu gugcgccaga gccaaggccc cuccccccguc   5160
cugggacgcc auguggaagu gccuggcccg acucaagccu acgcuugcgg gccccacacc   5220
ucuccuguac cguuugggcc cuauuaccaa ugaggucacc cucacacacc cugggacgaa   5280
guacaucgcc acaugcaugc aagcugaccu ugaggucaug accagcacgu ggguccuagc   5340
uggaggaguc cuggcagccg ucgccgcaua uugccuggcg acuggaugcg uuuccaucau   5400
cggccgcuug cacgucaacc agcgagucgu cguugcgccg gauaaggagg uccuguauga   5460
ggcuuuugau gagauggagg aaugcgccuc uagggcggcu cucaucgaag aggggcagcg   5520
gauagccgag auguugaagu ccaagaucca aggcuugcug cagcaggccu cuaagcaggc   5580
ccaggacaua caacccgcua ugcaggcuuc auggcccaaa guggaacaau uuugggccag   5640
acacauguug aacuucauua gcggcaucca auaccucgca ggauugucaa cacugccagg   5700
gaaccccgcg guggcuucca ugauggcauu cagugccgcc cucaccaguc cguugucgac   5760
caguaccacc auccuucuca acaucauggg aggcugguua gcgucccaga ucgcaccacc   5820
cgcgggggcc accggcuuug ucgucagugg ccuggugggg gcugccgugg gcagcauagg   5880
ccuggguaag gugcuggugg acauccuggc aggauauggu gcgggcauuu cgggggcccu   5940
cgucgcauuc aagaucaugu cuggcgagaa gcccucuaug gaagauguca ucaaucuacu   6000
gccugggauc cugucuccgg gagcccuggu gguggggguc aucugcgcgg ccauucugcg   6060
ccgccacgug ggaccggggg agggcgcggu ccaauggaug aacaggcuua uugccuuugc   6120
uuccagagga aaccacgucg ccccuacuca cuacgugacg gagucggaug cgucgcagcg   6180
ugugacccaa cuacuuggcu cucuuacuau aaccagccua cucagaagac uccacaauug   6240
gauaacugag gacugcccca ucccaugcuc cggauccugg cuccgcgacg ugugggacug   6300
gguuugcacc aucuugacag acuucaaaaa uuggcugacc ucuaaauugu uccccaagcu   6360
gcccggccuc cccuucaucu cuugucaaaa gggguacaag ggugugugggg ccggcacugg   6420
caucaugacc acgcgcugcc cuugcggcgc caacaucucu ggcaaugucc gccugggcuc   6480
uaugaggauc acagggccua aaaccugcau gaacaccugg caggggaccu uuccuaucaa   6540
uugcuacacg gagggccagu gcgcgccgaa acccccccacg aacuacaaga ccgccaucug   6600
gagggguggcg gccucggagu acgcggaggu gacgcagcau gggucguacu ccuauguaac   6660
aggacugacc acugacaauc ugaaaauucc uugccaacua ccuucuccag aguuuuucuc   6720
cuggguggac ggugugcaga uccauagguu ugcacccaca ccaaagccgu uuuuccggga   6780
ugaggucucg uucugcguug ggcuuaauuc cuaugcuguc ggguccccagc uucccuguga   6840
accugagccc gacgcagacg uauugagguc caugcuaaca gauccgcccc acaucacggc   6900
ggagacugcg gcgcggcgcu uggcacgggg aucaccucca ucugaggcga gcuccucagu   6960
gagccagcua ucagcaccgu cgcugcgggc caccugcacc acccacagca acaccuauga   7020
cguggacaug gucgaugcca accugcucau ggagggcggu guggcucaga cagagccuga   7080
guccagggug cccguucugg acuuucucga gccaauggcc gaggaagaga gcgaccuuga   7140
gcccucaaua ccaucggagu gcaugcuccc caggagcggg uuuccacggg ccuuaccggc   7200
uugggcacgg ccugacuaca acccgccgcu cguggaaucg uggaggaggc cagauuacca   7260
accgcccacc guugcugguu gugcucuccc cccccccaag aaggccccga cgccuccccc   7320
aaggagacgc cggacagugg gucugagcga gagcaccaua ucagaagccc uccagcaacu   7380
```

-continued

```
ggccaucaag accuuuggcc agccccccuc gagcggugau gcaggcucgu ccacgggggc   7440
gggcgccgcc gaauccggcg guccgacguc cccuggugag ccggccccccu cagagacagg   7500
uuccgccucc ucuaugcccc cccucgaggg ggagccugga gauccggacc uggagucuga   7560
ucagguagag cuucaaccuc ccccccaggg ggggggggua gcucccgguu cgggcucggg   7620
gucuuggucu acuugcuccg aggaggacga uaccaccgug ugcugcucca ugucauacuc   7680
cuggaccggg gcucuaauaa cucccuguag ccccgaagag gaaaaguugc caaucaaccc   7740
uuugaguaac ucgcuguugc gauaccauaa caaggugauc uguacaacau caaagagcgc   7800
cucacagagg gcuaaaaagg uaacuuuuga caggacgcaa gugcucgacg cccauuauga   7860
cucagucuua aaggacauca agcuagcggc uuccaagguc agcgcaaggc uccucaccuu   7920
ggaggaggcg ugccaguuga cuccacccca uucugcaaga uccaaguaug gauucggggc   7980
caaggagguc cgcagcuugu ccgggagggc cguuaaccac aucaaguccg uguggaagga   8040
ccuccuggaa gacccacaaa caccaauucc cacaaccauc auggccaaaa augaggugu    8100
cugcguggac cccgccaagg ggguaagaa  accagcucgc cucaucguuu acccugaccu   8160
cggcguccgg gucugcgaga aaauggcccu cuaugacauu acacaaaagc uuccucaggc   8220
gguaauggga gcuuccuaug gcuuccagua cuccccugcc caacgggugg aguaucucuu   8280
gaaagcaugg gcggaaaaga aggaccccau ggguuuuucg uaugauaccc gaugcuucga   8340
cucaaccguc acugagagag acaucaggac cgaggagucc auauaccagg ccugcucccu   8400
gcccgaggag gcccgcacug ccauacacuc gcugacugag agacuuuacg uaggagggcc   8460
cauguucaac agcaagguc  aaaccugcgg uuacagacgu ugccgcgcca gcggggugcu   8520
aaccacuagc augggguaaca ccaucacaug cuaugugaaa gcccuagcgg ccugcaaggc   8580
ugcggggaua guugcgccca caaugcuggu augcggcaau gaccuaguag ucaucucaga   8640
aagccagggg acugaggagg acgagcggaa ccugagagcc uucacggagg ccaugaccag   8700
guacucugcc ccuccuggug aucccccccag accggaauau gaccuggagc uaauaacauc   8760
cuguuccuca aaugugucug uggcguuggg cccgcggggc cgccgcagau acuaccugac   8820
cagagaccca accacuccac ucgcccgggc ugccugggaa acaguuagac acuccccuau   8880
caauucaugg cugggaaaca ucauccagua ugcuccaacc auaugggguuc gcaugguccu   8940
aaugacacac uucuucucca uucucauggu ccaagacacc cuggaccaga accucaacuu   9000
ugagauguau ggaucaguau acuccgugaa uccuuuggac cuuccagcca uaauugagag   9060
guuacacggg cuugacgccu uuucuaugca cacauacucu caccacgaac ugacgcgggu   9120
ggcuucagcc cucagaaaac uuggggcgcc accccucagg guguggaaga gucgggcucg   9180
cgcagucagg gcgucccuca ucucccgugg agggaaagcg gccguuugcg gccgauaucu   9240
cuucaauugg gcggugaaga ccaagcucaa acucacucca uugccggagg cgcgccuacu   9300
ggacuuaucc aguugguuca ccgucggcgc cggcgggggc gacauuuuuc acagcguguc   9360
gcgcgcccga ccccgcucau uacucuucgg ccuacuccua cuuuucguag ggguaggccu   9420
cuuccuacuc cccgcucggu agagcggcac acacuaggua cacuccauag cuaacuguuc   9480
cuuuuuuuuu uuuuuuuuuu uuuuuuuuuu uuuuuuuuuu uuuucuuuuu uuuuuuuuuc   9540
ccucuuucuu cccuucucau cuuauucuac uuucuuucuu gguggcucca ucuuagcccu   9600
agucacggcu agcugugaaa gguccgugag ccgcaugacu gcagagagug ccguaacugg   9660
ucucucugca gaucaugu                                                 9678
```

-continued

<210> SEQ ID NO 16
<211> LENGTH: 17
<212> TYPE: DNA
<213> ORGANISM: Artificial Sequence
<220> FEATURE:
<223> OTHER INFORMATION: Synthetic primer

<400> SEQUENCE: 16
cgggagagcc atagtgg 17

<210> SEQ ID NO 17
<211> LENGTH: 19
<212> TYPE: DNA
<213> ORGANISM: Artificial Sequence
<220> FEATURE:
<223> OTHER INFORMATION: Synthetic primer

<400> SEQUENCE: 17
agtaccacaa ggcctttcg 19

<210> SEQ ID NO 18
<211> LENGTH: 21
<212> TYPE: DNA
<213> ORGANISM: Artificial Sequence
<220> FEATURE:
<223> OTHER INFORMATION: Synthetic primer

<400> SEQUENCE: 18
ctgcggaacc ggtgagtaca c 21

<210> SEQ ID NO 19
<211> LENGTH: 20
<212> TYPE: DNA
<213> ORGANISM: Artificial Sequence
<220> FEATURE:
<223> OTHER INFORMATION: Synthetic primer

<400> SEQUENCE: 19
aacaagatgg attgcacgca 20

<210> SEQ ID NO 20
<211> LENGTH: 20
<212> TYPE: DNA
<213> ORGANISM: Artificial Sequence
<220> FEATURE:
<223> OTHER INFORMATION: Synthetic primer

<400> SEQUENCE: 20
cgtcaagaag gcgatagaag 20

<210> SEQ ID NO 21
<211> LENGTH: 11969
<212> TYPE: RNA
<213> ORGANISM: Artificial Sequence
<220> FEATURE:
<223> OTHER INFORMATION: replicon RNA derived from the expression
vector rFGR-JFH1/Luc

<400> SEQUENCE: 21
accugccccu aauaggggcg acacuccgcc augaaucacu ccccugugag gaacuacugu 60
cuucacgcag aaagcgccua gccauggcgu uaguaugagu gucguacagc cuccaggccc 120
cccccucccg ggagagccau aguggucugc ggaaccggug aguacaccgg aauugccggg 180
aagacugggu ccuuucuugg auaaacccac ucuaugcccg gccauuuggg cgugcccccg 240
caagacugcu agccgaguag cguuggguug cgaaaggccu ugugguacug ccugauaggg 300

-continued

```
cgcuugcgag ugccccggga ggucucguag accgugcacc augagcacaa auccuaaacc    360
ucaaagaaaa accaaaagaa acaccaaccg acgcguaaug gaagacgcca aaaacauaaa    420
gaaaggcccg gcgccauucu auccucugga ggauggaacc gcuggagagc aacugcauaa    480
ggcuaugaag agauacgccc ugguuccugg aacaauugcu uuuacagaug cacauaucga    540
ggugaacauc acguacgcgg aauacuucga aauguccguu cgguuggcag aagcuaugaa    600
acgauauggg cugaauacaa aucacagaau cgucguaugc agugaaaacu cucuucaauu    660
cuuuaugccg guguugggcg cguuauuuau cggaguugca guugcgcccg cgaacgacau    720
uuauaaugaa cgugaauugc ucaacaguau gaacauuucg cagccuaccg uaguguuugu    780
uuccaaaaag ggguugcaaa aaauuuugaa cgugcaaaaa aaauuaccaa uaauccagaa    840
aauuauuauc auggauucua aaacggauua ccagggauuu cagucgaugu acacguucgu    900
cacaucucau cuaccucccg guuuuaauga auacgauuuu guaccagagu ccuuugaucg    960
ugacaaaaca auugcacuga uaaugaacuc cucuggaucu acuggguuac cuaagggugu   1020
ggcccuuccg cauagaacug ccugcgucag auucucgcau gccagagauc cuauuuuugg   1080
caaucaaauc auuccggaua cugcgauuuu aaguguuguu ccauuccauc acgguuuugg   1140
aauguuuacu acacucggau auuugauaug uggauuucga gucgucuuaa uguauagauu   1200
ugaagaagag cuguuuuuac gaucccuuca ggauuacaaa auucaaagug cguugcuagu   1260
accaacccua uuuucauucu ucgccaaaag cacucugauu gacaaauacg auuuaucuaa   1320
uuuacacgaa auugcuucug gggcgcaccc ucuuucgaaa gaagucgggg aagcgguugc   1380
aaaacgcuuc caucuuccag ggauacgaca aggauauggg cucacugaga cuacaucagc   1440
uauucugauu acacccgagg gggaugauaa accgggcgcg gucgguaaag uuguuccauu   1500
uuuugaagcg aagguugugg aucuggauac cgggaaaacg cugggcguua aucagagagg   1560
cgaauuaugu gucagaggac cuaugauuau guccgguuau guaaacaauc cggaagcgac   1620
caacgccuug auugacaagg auggauggcu acauucugga gacauagcuu acugggacga   1680
agacgaacac uucuucauag uugaccgcuu gaagucuuua auuaaauaca aaggauauca   1740
gguggccccc gcugaauugg aaucgauauu guuacaacac cccaacaucu ucgacgcggg   1800
cguggcaggu cuucccgacg augacgccgg ugaacuuccc gccgccguug uuguuuugga   1860
gcacggaaag acgaugacgg aaaaagagau cguggauuac gucgccaguc aaguaacaac   1920
cgcgaaaaag uugcgcggag gaguuguguu uguggacgaa guaccgaaag gucuuaccgg   1980
aaaacucgac gcaagaaaaa ucagagagau ccucauaaag gccaagaagg gcggaaaguc   2040
caaauuguaa guuuaaaccc ucucccuccc ccccccuaa cguuacuggc cgaagccgcu    2100
uggaauaagg ccggugugcg uuugucuaua uguuauuuuc caccauauug ccgucuuuug   2160
gcaaugugag ggcccggaaa ccuggcccug ucuucuugac gagcauuccu aggggucuuu   2220
ccccucucgc caaaggaaug caaggucugu ugaaugucgu gaaggaagca guuccucugg   2280
aagcuucuug aagacaaaca acgucuguag cgacccuuug caggcagcgg aaccccccac   2340
cuggcgacag gugccucugc ggccaaaagc cacguguaua agauacaccu gcaaaggcgg   2400
cacaacccca gugccacguu gugaguugga uaguugugga aagagucaaa uggcucuccu   2460
caagcguauu caacaagggg cugaaggaug cccagaaggu accccauugu augggaucug   2520
aucuggggcc ucggugcaca ugcuuuacau guguuuaguc gagguuaaaa aaacgucuag   2580
gccccccgaa ccacggggac gugguuuucc uuugaaaaac acgaugauac caugagcaca   2640
aauccuaaac cucaaagaaa aaccaaaaga aacaccaacc gucgcccaga agacguuaag   2700
```

-continued

```
uucccgggcg gcggccagau cguuggcgga guauacuugu ugccgcgcag gggccccagg   2760
uugggugugc gcacgacaag gaaaacuucg gagcggaccc agccacgugg gagacgccag   2820
cccaucccca aagaucggcg cuccacuggc aaggccuggg gaaaaccagg ucgccccugg   2880
ccccuauaug ggaaugaggg acucggcugg gcaggauggc uccuguccc ccgaggcucu    2940
cgccccuccu ggggccccac ugacccccgg cauaggucgc gcaacguggg uaaagucauc   3000
gacacccuaa cguguggcuu ugccgaccuc augggguaca uccccgucgu aggcgccccg   3060
cuuaguggcg ccgccagagc ugucgcgcac ggcgugagag uccuggagga cgggguuaau   3120
uaugcaacag ggaaccuacc cgguuucccc uuuucuaucu ucuugcuggc ccuguugucc   3180
ugcaucaccg uuccggucuc ugcugcccag gugaagaaua ccaguagcag cuacauggug   3240
accaaugacu gcuccaauga cagcaucacu uggcagcucg aggcugcggu ucuccacguc   3300
cccgggugcg ucccgugcga gagagugggg aauacgucac gguguugggu gccagucucg   3360
ccaaacaugg cugugcggca gcccggugcc cucacgcagg gucugcggac gcacaucgau   3420
augguuguga uguccgccac cuucugcucu gcucucuacg ugggggaccu cuguggcggg   3480
gugaugcucg cggcccaggu guucaucguc ucgccgcagu accacugguu ugugcaagaa   3540
ugcaauugcu ccaucuaccc uggcaccauc acuggacacc gcauggcaug ggacaugaug   3600
augaacuggu cgcccacggc caccaugauc cuggcguacg ugaugcgcgu ccccgagguc   3660
aucauagaca ucguuagcgg ggcucacugg ggcgucaugu ucggcuuggc cuacuucucu   3720
augcagggag cgugggcgaa ggucauuguc auccuucugc uggccgcugg gguggacgcg   3780
ggcaccacca ccguuggagg cgcuguugca cguuccacca acgugauugc cggcguguuc   3840
agccauggcc cucagcagaa cauucagcuc auuaacacca acggcaguug gcacaucaac   3900
cguacugccu ugaauugcaa ugacuccuug aacaccggcu uucucgcggc cuuguucuac   3960
accaaccgcu uuaacucguc agggugucca gggcgccugu ccgccugccg caacaucgag   4020
gcuuuccgga uagggugggg cacccuacag uacgaggaua augucaccaa uccagaggau   4080
augaggccgu acugcuggca cuaccccca aagccgugug gcguaguccc cgcgaggucu    4140
gugugugcc caguguacug uuucaccccc agcccgguag uagugggcac gaccgacaga    4200
cguggagugc ccaccuacac auggggagag aaugagacag augucuuccu acugaacagc   4260
acccgaccgc cgcagggcuc augguucggc ugcacgugga ugaacuccac ugguuucacc   4320
aagacuugug gcgcgccacc uugccgcacc agagcugacu ucaacgccag cacggacuug   4380
uugugcccua cggauuguuu uaggaagcau ccugaugcca cuuauauuaa gugugguucu   4440
gggcccuggc ucacaccaaa gugccugguc cacuacccuu acagacucug gcauuacccc   4500
ugcacaguca auuuuaccau cuucaagaua agaauguaug uaggggggu ugagcacagg    4560
cucacggccg caugcaacuu cacucguggg gaucgcugcg acuuggagga cagggacagg   4620
agucagcugu cuccucuguu gcacucuacc acggaauggg ccauccugcc cugcaccuac   4680
ucagacuuac ccgcuuuguc aacuggucuu cuccaccuuc accagaacau cguggacgua   4740
caauacaugu auggccucuc accugcuauc acaaaauacg ucguucgaug ggagugggug   4800
guacucuuau uccugcucuu agcggacgcc agagucugcg ccugcuugug gaugcucauc   4860
uuguugggcc aggccgaagc agcauuggag aaguuggucg ucuugcacgc ugcgagugcg   4920
gcuaacugcc auggccuccu auauuuugcc aucuucuucg uggcagcuug gcacaucagg   4980
ggucgggugg uccccuugac caccuauugc cucacuggcc uauggcccuu cugccuacug   5040
cucauggcac ugccccggca ggcuuaugcc uaugacgcac cugugcacgg acagauaggc   5100
```

-continued

```
gugggguuugu ugauauugau cacccucuuc acacucaccc cgggguauaa gacccuccuc   5160
ggccagugucc uguggugguu gugcuaucuc cugacccugg gggaagccau gauucaggag   5220
uggguaccac ccaugcaggu gcgcggcggc cgcgauggca ucgcgugggc cgucacuaua   5280
uucugcccgg guguggugu ugacauuacc aaauggcuuu uggcguugcu ugggccugcu   5340
uaccucuuaa gggccgcuuu gacacaugug ccguacuucg ucagagcuca cgcucugaua   5400
aggguaugcg cuuuggugaa gcagcucgcg gggggguaggu auguucaggu ggcgcuauug   5460
gcccuuggca gguggacugg caccuacauc uaugaccacc ucacaccuau gucggacugg   5520
gccgcuagcg gccugcgcga cuuagcgguc gccguggaac ccaucaucuu caguccgaug   5580
gagaagaagg ucaucgucug gggagcggag acggcugcau guggggacau ucuacaugga   5640
cuucccgugu ccgcccgacu cggccaggag auccuccucg gcccagcuga uggcuacacc   5700
uccaaggggu ggaagcuccu ugcucccauc acugcuuaug cccagcaaac acgaggccuc   5760
cugggcgcca uaguggugag uaugacgggg cgugacagga cagaacaggc cggggaaguc   5820
caaauccugu ccacagucuc ucaguccuuc cucggaacaa ccaucucggg gguuuugugg   5880
acuguuuacc acggagcugg caacaagacu cuagccggcu uacgggggucc ggucacgcag   5940
auguacucga gugcugaggg ggacuuggua ggcuggccca gcccccccugg gaccaagucu   6000
uuggagccgu gcaagugugg agccgucgac cuauaucugg ucacgcggaa cgcugauguc   6060
aucccggcuc ggagacgcgg ggacaagcgg ggagcauugc ucucccccgag acccauuucg   6120
accuugaagg gguccucggg ggggccggug cucugcccua ggggccacgu cguugggcuc   6180
uuccgagcag cugugugcuc ucggggcgug gccaaaucca ucgauuucau ccccguugag   6240
acacucgacg uuguuacaag gucucccacu uucagugaca acagcacgcc accggcugug   6300
ccccagaccu aucaggucgg guacuugcau gcuccaacug gcaguggaaa gagcaccaag   6360
gucccugucg cguaugccgc ccagggguac aaaguacuag ugcuuaaccc cucgguagcu   6420
gccacccugg gguuuggggc guaccuaucc aaggcacaug gcaucaaucc caacauuagg   6480
acuggaguca ggaccgugau gaccggggag gccaucacgu acuccacaua uggcaaauuu   6540
cucgccgaug ggggcugcgc uagcggcgcc uaugacauca ucauaugcga ugaaugccac   6600
gcuguggaug cuaccuccau ucucggcauc ggaacggucc uugaucaagc agagacagcc   6660
ggggucagac uaacugugcu ggcuacggcc acacccccccg ggucagugac aaccccccau   6720
cccgauauag aagagguagg ccucgggcgg gagggugaga uccccuucua ugggagggcg   6780
auuccccuau ccugcaucaa gggagggaga caccugauuu ucugccacuc aaagaaaaag   6840
ugugacgagc ucgcggcggc ccuucggggc augggcuuga augccguggc auacuauaga   6900
ggguuggacg ucuccauaau accagcucag ggagaugugg uggucgucgc caccgacgcc   6960
cucaugacgg gguacacugg agacuuugac uccgugaucg acugcaaugu agcggucacc   7020
caagcugucg acuucagccu ggaccccacc uucacuauaa ccacacagac ugucccacaa   7080
gacgcugucu cacgcaguca gcgccgcggg cgcacaggua gaggaagaca gggcacuuau   7140
agguauguuu ccacugguga acgagccuca ggaauguuug acaguguagu gcuuugugag   7200
ugcuacgacg caggggcugc gugguacgau cucacaccag cggagaccac cgucaggcuu   7260
agagcguauu ucaacacgcc cggccuaccc gugugucaag accaucuuga auuuugggag   7320
gcaguuuuca ccggccucac acacauagac gcccacuucc ucucccaaac aaagcaagcg   7380
ggggagaacu ucgcguaccu aguagccuac caagcuacgg ugugcgccag agccaaggcc   7440
ccucccccgu ccugggacgc cauguggaag ugccuggccc gacucaagcc uacgcuugcg   7500
```

-continued

```
ggccccacac cucuccugua ccguuugggc ccuauuacca augaggucac ccucacacac   7560
ccugggacga aguacaucgc cacaugcaug caagcugacc uugaggucau gaccagcacg   7620
uggguccuag cuggaggagu ccuggcagcc gucgccgcau auugccuggc gacuggaugc   7680
guuuccauca ucggccgcuu gcacgucaac cagcgagucg ucguugcgcc ggauaaggag   7740
guccuguaug aggcuuuuga ugagauggag gaaugcgccu cuagggcggc ucucaucgaa   7800
gaggggcagc ggauagccga gauguugaag uccaagaucc aaggcuugcu gcagcaggcc   7860
ucuaagcagg cccaggacau acaacccgcu augcaggcuu cauggcccaa aguggaacaa   7920
uuuugggcca gacacaugug gaacuucauu agcggcaucc aauaccucgc aggauuguca   7980
acacugccag ggaaccccgc gguggcuucc augauggcau ucagugccgc ccucaccagu   8040
ccguugucga ccaguaccac cauccuucuc aacaucaugg gaggcugguu agcgucccag   8100
aucgcaccac ccgcgggggc caccggcuuu gucgucagug gccugguggg ggcugccgug   8160
ggcagcauag gccuggguaa ggugcuggug gacauccugg caggauaugg ugcgggcauu   8220
ucgggggccc ucgucgcauu caagaucaug ucuggcgaga agcccucuau ggaagauguc   8280
aucaaucuac ugccugggau ccugucuccg ggagcccugg uggugggggu caucugcgcg   8340
gccauucugc gccgccacgu gggaccgggg gagggcgcgg uccaauggau gaacaggcuu   8400
auugccuuug cuuccagagg aaaccacguc gccccuacuc acuacgugac ggagucggau   8460
gcgucgcagc gugugaccca acuacuuggc ucucuuacua uaaccagccu acucagaaga   8520
cuccacaauu ggauaacuga ggacugcccc aucccaugcu ccggauccug gcuccgcgac   8580
gugugggacu ggguuugcac caucuugaca gacuucaaaa auuggcugac cucuaaauug   8640
uuccccaagc ugcccggccu ccccuucauc ucuugucaaa aggguacaa gggugugugg   8700
gccggcacug gcaucaugac cacgcgcugc ccuugcggcg ccaacaucuc uggcaauguc   8760
cgccugggcu cuaugaggau cacagggccu aaaaccugca ugaacaccug gcaggggacc   8820
uuuccuauca auugcuacac ggagggccag ugcgcgccga aacccccac gaacuacaag   8880
accgccaucu ggaggguggc ggccucggag uacgcggagg ugacgcagca ugggucguac   8940
uccuauguaa caggacugac cacugacaau cugaaaauuc cuugccaacu accuucucca   9000
gaguuuuucu ccugggugga cggugugcag auccauaggu uugcacccac accaaagccg   9060
uuuuuccggg augaggucuc guucugcguu gggcuuaauu ccuaugcugu cggguccag   9120
cuucccugug aaccugagcc cgacgcagac guauugaggu ccaugcuaac agauccgccc   9180
cacaucacgg cggagacugc ggcgcggcgc uuggcacggg gaucaccucc aucugaggcg   9240
agcuccucag ugagccagcu aucagcaccg ucgcugcggg ccaccugcac cacccacagc   9300
aacaccuaug acguggacau ggucgaugcc aaccugcuca uggagggcgg uguggcucag   9360
acagagccug aguccagggu gcccguucug gacuuucucg agccaauggc cgaggaagag   9420
agcgaccuug agcccucaau accaucggag ugcaugcucc ccaggagcgg guuuccacgg   9480
gccuuaccgg cuugggcacg gccugacuac aacccgccgc ucguggaauc guggaggagg   9540
ccagauuacc aaccgcccac cguugcuggu ugugcucucc cccccccaa gaaggccccg   9600
acgccucccc caaggagacg ccggacagug ggucugagcg agagcaccau aucagaagcc   9660
cuccagcaac uggccaucaa gaccuuuggc cagccccccu cgagcgguga ugcaggcucg   9720
uccacggggg cgggcgccgc cgaauccggc gguccgacgu ccccuggua gccggccccc   9780
ucagagacag guuccgccuc cucuaugccc ccccucgagg gggagccugg agauccggac   9840
cuggagucug aucagguaga gcuucaaccu cccccccagg gggggggggu agcucccggu   9900
```

ucgggcucgg ggucuugguc uacuugcucc gaggaggacg auaccaccgu gugcugcucc 9960
augucauacu ccuggaccgg ggcucuaaua acucccugua gccccgaaga ggaaaaguug 10020
ccaaucaacc cuuugaguaa cucgcuguug cgauaccaua acaaggugua cuguacaaca 10080
ucaaagagcg ccucacagag ggcuaaaaag guaacuuuug acaggacgca agugcucgac 10140
gcccauuaug acucagucuu aaaggacauc aagcuagcgg cuuccaaggu cagcgcaagg 10200
cuccucaccu uggaggaggc gugccaguug acuccacccc auucugcaag auccaaguau 10260
ggauucgggg ccaaggaggu ccgcagcuug uccgggaggg ccguuaacca caucaagucc 10320
guguggaagg accuccugga agacccacaa acaccaauuc ccacaaccau cauggccaaa 10380
aaugaggugu ucugcgugga ccccgccaag gggggggggguaaga aaccagcucg ccucaucguu 10440
uacccugacc ucggcguccg ggucugcgag aaaauggccc ucuaugacau uacacaaaag 10500
cuuccucagg cgguaauggg agcuuccuau ggcuuccagu acuccccugc ccaacgggug 10560
gaguaucucu ugaaagcaug ggcggaaaag aaggacccca uggguuuuuc guaugauacc 10620
cgaugcuucg acucaaccgu cacugagaga gacaucagga ccgaggaguc cauauaccag 10680
gccugcuccc ugcccgagga ggcccgcacu gccauacacu cgcugacuga gagacuuuac 10740
guaggagggc ccauguucaa cagcaagggu caaaccugcg guuacagacg uugccgcgcc 10800
agcggggugc uaaccacuag caugggguaac accaucacau gcuaugugaa agcccuagcg 10860
gccugcaagg cugcggggau aguugcgccc acaaugcugg uaugcggcga ugaccuagua 10920
gucaucucag aaagccaggg gacugaggag gacgagcgga accugagagc cuucacggag 10980
gccaugacca gguacucugc cccuccuggu gaucccccca gaccggaaua ugaccuggag 11040
cuaauaacau ccuguuccuc aaaugugucu guggcguugg gcccgcgggg ccgccgcaga 11100
uacuaccuga ccagagaccc aaccacucca cucgcccggg cugccuggga aacaguuaga 11160
cacuccccua ucaauucaug gcugggaaac aucauccagu augcuccaac cauaugggguu 11220 cgcauggucc uaaugacaca cuucuucucc auucucaugg uccaagacac ccuggaccag 11280
aaccucaacu uugagaugua uggaucagua uacuccguga auccuuugga ccuuccagcc 11340
auaauugaga gguuacacgg gcuugacgcc uuuucuaugc acacauacuc ucaccacgaa 11400
cugacgcggg uggcuucagc ccucagaaaa cuuggggcgc caccccucag ggugguggaag 11460 agucgggcuc gcgcagucag ggcgucccuc aucucccgug gagggaaagc ggccguuugc 11520
ggccgauauc ucuucaauug ggcggugaag accaagcuca aacucacucc auugccggag 11580
gcgcgccuac uggacuuauc caguugguuc accgucggcg ccggcggggg cgacauuuuu 11640
cacagcgugu cgcgcgcccg accccgcuca uuacucuucg gccuacuccu acuuuucgua 11700
gggguaggcc ucuuccuacu ccccgcucgg uagagcggca cacacuaggu acacuccaua 11760
gcuaacuguu ccuuuuuuuu uuuuuuuuuu uuuuuuuuuu uuuuuuuuuu uuuuucuuuu 11820
uuuuuuuuuu cccucuuucu ucccuucuca ucuuauucua cuuucuuucu ugguggcucc 11880
aucuuagccc uagucacggc uagcugugaa agguccguga gccgcaugac ugcagagagu 11940
gccguaacug gucucucugc agaucaugu 11969

<210> SEQ ID NO 22
<211> LENGTH: 11969
<212> TYPE: RNA
<213> ORGANISM: Artificial Sequence
<220> FEATURE:
<223> OTHER INFORMATION: replicon RNA derived from the expression
vector rFGR-JFH1/Luc/GND

<400> SEQUENCE: 22

-continued

```
accugcccu aauaggggcg acacuccgcc augaaucacu ccccugugag gaacuacugu      60
cuucacgcag aaagcgccua gccauggcgu uaguaugagu gucguacagc cuccaggccc     120
cccccucccg ggagagccau aguggucugc ggaaccggug aguacaccgg aauugccggg     180
aagacugggu ccuuucuugg auaaacccac ucuaugcccg gccauuuggg cgugcccccg     240
caagacugcu agccgaguag cguuggguug cgaaaggccu ugugguacug ccugauaggg     300
cgcuugcgag ugccccggga ggucucguag accgugcacc augagcacaa auccuaaacc     360
ucaaagaaaa accaaaagaa acaccaaccg acgcguaaug gaagacgcca aaaacauaaa     420
gaaaggcccg gcgccauucu auccucugga ggauggaacc gcuggagagc aacugcauaa     480
ggcuaugaag agauacgccc ugguuccugg aacaauugcu uuuacagaug cacauaucga     540
ggugaacauc acguacgcgg aauacuucga aauguccguu cgguuggcag aagcuaugaa     600
acgauauggg cugaauacaa aucacagaau cgucguaugc agugaaaacu cucuucaauu     660
cuuuaugccg guguugggcg cguuauuuau cggaguugca guugcgcccg cgaacgacau     720
uuauaaugaa cgugaauugc ucaacaguau gaacauuucg cagccuaccg uaguguuugu     780
uuccaaaaag ggguugcaaa aaauuuugaa cgugcaaaaa aaauuaccaa uaauccagaa     840
aauuauuauc auggauucua aaacggauua ccagggauuu cagucgaugu acacguucgu     900
cacaucucau cuaccucccg guuuuaauga auacgauuuu guaccagagu ccuuugaucg     960
ugacaaaaca auugcacuga uaaugaacuc cucuggaucu acuggguuac cuaagggugu    1020
ggcccuuccg cauagaacug ccugcgucag auucucgcau gccagagauc cuauuuuugg    1080
caaucaaauc auuccggaua cugcgauuuu aaguguuguu ccauuccauc acgguuuugg    1140
aauguuuacu acacucggau auuugauaug uggauuucga gucgucuuaa uguauagauu    1200
ugaagaagag cuguuuuuac gaucccuuca ggauuacaaa auucaaagug cguugcuagu    1260
accaacccua uuuucauucu ucgccaaaag cacucugauu gacaaauacg auuuaucuaa    1320
uuuacacgaa auugcuucug ggggcgcacc ucuuucgaaa gaagucgggg aagcgguugc    1380
aaaacgcuuc caucuuccag ggauacgaca aggauauggg cucacugaga cuacaucagc    1440
uauucugauu acacccgagg gggaugauaa accgggcgcg gucgguaaag uuguuccauu    1500
uuuugaagcg aagguugugg aucuggauac cgggaaaacg cugggcguua aucagagagg    1560
cgaauuaugu gucagaggac cuaugauuau guccgguuau guaaacaauc cggaagcgac    1620
caacgccuug auugacaagg auggauggcu acauucugga gacauagcuu acugggacga    1680
agacgaacac uucuucauag uugaccgcuu gaagucuuua auuaaauaca aaggauauca    1740
gguggccccc gcugaauugg aaucgauauu guuacaacac cccaacaucu ucgacgcggg    1800
cguggcaggu cuucccgacg augacgccgg ugaacuuccc gccgccguug uuguuuugga    1860
gcacggaaag acgaugacgg aaaaagagau cguggauuac gucgccaguc aaguaacaac    1920
cgcgaaaaag uugcgcggag gaguuguguu uguggacgaa guaccgaaag gucuuaccgg    1980
aaaacucgac gcaagaaaaa ucagagagau ccucauaaag gccaagaagg gcggaaaguc    2040
caaauuguaa guuuaaaccc ucucccuccc cccccccuaa cguuacuggc cgaagccgcu    2100
uggaauaagg ccggugugcg uuugucuaua uguuauuuuc caccauauug ccgucuuuug    2160
gcaaugugag ggcccggaaa ccuggcccug ucuucuugac gagcauuccu aggggucuuu    2220
ccccucucgc caaaggaaug caaggucugu ugaaugucgu gaaggaagca guuccucugg    2280
aagcuucuug aagacaaaca acgucuguag cgacccuuug caggcagcgg aaccccccac    2340
cuggcgacag gugccucugc ggccaaaagc cacguguaua agauacaccu gcaaaggcgg    2400
```

-continued cacaacccca gugccacguu gugaguugga uaguugugga aagagucaaa uggcucuccu 2460
caagcguauu caacaagggg cugaaggaug cccagaaggu accccauugu augggaucug 2520
aucuggggcc ucggugcaca ugcuuuacau guguuuaguc gagguuaaaa aaacgucuag 2580
gccccccgaa ccacggggac gugguuuucc uuugaaaaac acgaugauac caugagcaca 2640
aauccuaaac cucaaagaaa aaccaaaaga aacaccaacc gucgcccaga agacguuaag 2700
uucccgggcg gcggccagau cguuggcgga guauacuugu ugccgcgcag gggccccagg 2760
uugggugugc gcacgacaag gaaaacuucg gagcgguccc agccacgugg gagacgccag 2820
cccaucccca aagaucggcg cuccacuggc aaggccuggg gaaaaccagg ucgccccugg 2880
ccccuauaug ggaaugaggg acucggcugg gcaggauggc uccuguccc ccgaggcucu 2940 cgccccuccu ggggccccac ugacccccgg cauaggucgc gcaacguggg uaaagucauc 3000
gacacccuaa cguguggcuu ugccgaccuc auggggguaca uccccgucgu aggcgccccg 3060
cuuaguggcg ccgccagagc ugucgcgcac ggcgugagag uccuggagga cggggguuaau 3120 uaugcaacag ggaaccuacc cgguuucccc uuuucuaucu ucuugcuggc ccuguuguccc 3180 ugcaucaccg uuccggucuc ugcugcccag gugaagaaua ccaguagcag cuacauggug 3240
accaaugacu gcuccaauga cagcaucacu uggcagcucg aggcugcggu ucuccacguc 3300
cccgggugcg ucccgugcga gagaguuggg aauacgucac gguguugggu gccagucucg 3360
ccaaacaugg cugugcggca gcccggugcc cucacgcagg gucugcggac gcacaucgau 3420
augguuguga uguccgccac cuucugcucu gcucucuacg ugggggaccu cuguggcggg 3480
gugaugcucg cggcccaggu guucaucguc ucgccgcagu accacugguu ugugcaagaa 3540
ugcaauugcu ccaucuaccc uggcaccauc acuggacacc gcauggcaug ggacaugaug 3600
augaacuggu cgcccacggc caccaugauc cuggcguacg ugaugcgcgu ccccgagguc 3660
aucauagaca ucguuagcgg ggcucacugg ggcgucaugu ucggcuuggc cuacuucucu 3720
augcagggag cgugggcgaa ggucauuguc auccuucugc uggccgcugg ggugggacgcg 3780 ggcaccacca ccguuggagg cgcuguugca cguuccacca acgugauugc cggcguguuc 3840
agccauggcc cucagcagaa cauucagcuc auuaacacca acggcaguug gcacaucaac 3900
cguacugccu ugaauugcaa ugacuccuug aacaccggcu uucucgcggc cuuguucuac 3960
accaaccgcu uuaacucguc agggugucca gggcgccugu ccgccugccg caacaucgag 4020
gcuuuccgga uagggugggg cacccuacag uacgaggaua augucaccaa uccagaggau 4080
augaggccgu acugcuggca cuaccccca aagccgugug gcguaguccc cgcgaggucu 4140
gugugugccc caguguacug uuucacccc agcccgguag uaguggcac gaccgacaga 4200 cguggagugc ccaccuacac auggggagag aaugagacag augucuuccu acugaacagc 4260
acccgaccgc cgcagggcuc augguucggc ugcacgugga ugaacuccac ugguuucacc 4320
aagacuugug gcgcgccacc uugccgcacc agagcugacu ucaacgccag cacggacuug 4380
uugugcccua cggauuguuu uaggaagcau ccugaugcca cuuauauuaa guguggguucu 4440 gggcccuggc ucacaccaaa gugccugguc cacuacccuu acagacucug gcauuacccc 4500
ugcacaguca auuuuaccau cuucaagaua agaauguaug uaggggggu ugagcacagg 4560 cucacggccg caugcaacuu cacucguggg gaucgcugcg acuuggagga cagggacagg 4620
agucagcugu cuccucuguu gcacucuacc acggaauggg ccauccugcc cugcaccuac 4680
ucagacuuac ccgcuuuguc aacuggucuu cuccaccuuc accagaacau cguggacgua 4740
caauacaugu auggccucuc accugcuauc acaaaauacg ucguucgaug ggagugggug 4800
guacucuuau uccugcucuu agcggacgcc agagucugcg ccugcuugug gaugcucauc 4860
uuguugggcc aggccgaagc agcauuggag aaguuggucg ucuugcacgc ugcgagugcg 4920
gcuaacugcc auggccuccu auauuuugcc aucuucuucg uggcagcuug gcacaucagg 4980
ggucgggugg uccccuugac caccuauugc cucacuggcc uauggcccuu cugccuacug 5040
cucauggcac ugccccggca ggcuuaugcc uaugacgcac cugugcacgg acagauaggc 5100 gugggguuugu ugauauugau cacccucuuc acacucaccc cgggguauaa gacccuccuc 5160
ggccaguguc uguggugguu gugcuaucuc cugacccugg gggaagccau gauucaggag 5220
uggguaccac ccaugcaggu gcgcggcggc cgcgauggca ucgcgugggc cgucacuaua 5280
uucugcccgg guguggugu ugacauuacc aaauggcuuu uggcguugcu ugggccugcu 5340
uaccucuuaa gggccgcuuu gacacaugug ccguacuucg ucagagcuca cgcucugaua 5400
aggguaugcg cuuuggugaa gcagcucgcg gggggguaggu auguucaggu ggcgcuauug 5460
gcccuuggca gguggacugg caccuacauc uaugaccacc ucacaccuau gucggacugg 5520
gccgcuagcg gccugcgcga cuuagcgguc gccguggaac ccaucaucuu caguccgaug 5580
gagaagaagg ucaucgucug ggagcggag acggcugcau guggggacau ucuacaugga 5640
cuucccgugu ccgcccgacu cggccaggag auccuccucg gcccagcuga uggcuacacc 5700
uccaaggggu ggaagcuccu ugcucccauc acugcuuaug cccagcaaac acgaggccuc 5760
cugggcgcca uagugguag uaugacgggg cgugacagga cagaacaggc cggggaaguc 5820
caaauccugu ccacagucuc ucaguccuuc cucggaacaa ccaucucggg gguuuugugg 5880
acuguuuacc acggagcugg caacaagacu cuagccggcu uacggggucc ggucacgcag 5940
auguacucga gugcugaggg ggacuuggua ggcuggccca gcccccccugg gaccaagucu 6000 uuggagccgu gcaagugugg agccgucgac cuauaucugg ucacgcggaa cgcugauguc 6060
aucccggcuc ggagacgcgg ggacaagcgg ggagcauugc ucucccccgag acccauuucg 6120 accuugaagg gguccucggg ggggccggug cucugcccua ggggccacgu cguugggcuc 6180
uuccgagcag cugugugcuc ucggggcgug gccaaaucca ucgauuucau ccccguugag 6240
acacucgacg uuguuacaag gucucccacu uucagugaca acagcacgcc accggcugug 6300
ccccagaccu aucaggucgg guacuugcau gcuccaacug gcaguggaaa gagcaccaag 6360
gucccugucg cguaugccgc ccaggggguac aaaguacuag ugcuuaaccc cucgguagcu 6420
gccacccugg gguuuggggc guaccuaucc aaggcacaug gcaucaaucc caacauuagg 6480
acuggaguca ggaccgugau gaccggggag gccaucacgu acuccacaua uggcaaauuu 6540
cucgccgaug gggcugcgc uagcggcgcc uaugacauca ucauaugcga ugaaugccac 6600
gcuguggaug cuaccuccau ucucggcauc ggaacggucc uugaucaagc agagacagcc 6660
ggggucagac uaacugugcu ggcuacggcc acacccccccg ggucagugac aacccccccau 6720 cccgauauag aagagguagg ccucgggcgg gagggugaga uccccuucua ugggagggcg 6780
auuccccuau ccugcaucaa gggagggaga caccugauuu ucugccacuc aaagaaaaag 6840
ugugacgagc ucgcggcggc ccuucggggc augggcuuga augccguggc auacuauaga 6900
ggguuggacg ucuccauaau accagcucag ggagaugugg uggucgucgc caccgacgcc 6960
cucaugacgg gguacacugg agacuuugac uccgugaucg acugcaaugu agcggucacc 7020
caagcugucg acuucagccu ggaccccacc uucacuauaa ccacacagac ugucccacaa 7080
gacgcugucu cacgcaguca gcgccgcggg cgcacaggua gaggaagaca gggcacuuau 7140
agguauguuu ccacugguga acgagccuca ggaauguuug acaguguagu gcuuugugag 7200

-continued ugcuacgacg caggggcugc gugguacgau cucacaccag cggagaccac cgucaggcuu 7260
agagcguauu ucaacacgcc cggccuaccc gugugucaag accaucuuga auuuugggag 7320
gcaguuuuca ccggccucac acacauagac gcccacuucc ucucccaaac aaagcaagcg 7380
ggggagaacu ucgcguaccu aguagccuac caagcuacgg ugugcgccag agccaaggcc 7440
ccucccccgu ccugggacgc cauguggaag ugccuggccc gacucaagcc uacgcuugcg 7500
ggccccacac cucuccugua ccguuugggc ccuauuacca augaggucac ccucacacac 7560
ccugggacga aguacaucgc cacaugcaug caagcugacc uugaggucau gaccagcacg 7620 ugggucccuag cuggaggagu ccuggcagcc gucgccgcau auugccuggc gacuggaugc 7680
guuuccauca ucggccgcuu gcacgucaac cagcgagucg ucguugcgcc ggauaaggag 7740
guccuguaug aggcuuuuga ugagauggag gaaugcgccu cuagggcggc ucucaucgaa 7800
gaggggcagc ggauagccga gauguugaag uccaagaucc aaggcuugcu gcagcaggcc 7860
ucuaagcagg cccaggacau acaacccgcu augcaggcuu cauggcccaa aguggaacaa 7920
uuuugggcca gacacaugug gaacuucauu agcggcaucc aauaccucgc aggauuguca 7980
acacugccag ggaaccccgc gguggcuucc augauggcau ucagugccgc ccucaccagu 8040
ccguugucga ccaguaccac cauccuucuc aacaucaugg gaggcugguu agcgucccag 8100
aucgcaccac ccgcgggggc caccggcuuu gucgucagug gccuggugggg ggcugccgug 8160 ggcagcauag gccuggguaa ggugcuggug gacauccugg caggauaugg ugcgggcauu 8220
ucgggggccc ucgucgcauu caagaucaug ucuggcgaga agcccucuau ggaagauguc 8280
aucaaucuac ugccugggau ccugucuccg ggagcccugg uggugggggu caucugcgcg 8340
gccauucugc gccgccacgu gggaccgggg gagggcgcgg uccaauggau gaacaggcuu 8400
auugccuuug cuuccagagg aaaccacguc gccccuacuc acuacgugac ggagucggau 8460
gcgucgcagc gugugaccca acuacuuggc ucucuuacua uaaccagccu acucagaaga 8520
cuccacaauu ggauaacuga ggacugcccc aucccaugcu ccggauccug gcuccgcgac 8580
gugugggacu ggguuugcac caucuugaca gacuucaaaa auuggcugac cucuaaauug 8640
uuccccaagc ugcccggccu ccccuucauc ucuugucaaa agggguacaa gggugugugg 8700
gccggcacug gcaucaugac cacgcgcugc ccuugcggcg ccaacaucuc uggcaauguc 8760
cgccugggcu cuaugaggau cacagggccu aaaaccugca ugaacaccug gcaggggacc 8820
uuuccuauca auugcuacac ggagggccag ugcgcgccga aaccccccac gaacuacaag 8880
accgccaucu ggagggguggc ggccucggag uacgcggagg ugacgcagca ugggucguac 8940
ucccuaugua caggacugac cacugacaau cugaaaauuc cuugccaacu accuucucca 9000
gaguuuuucu ccugggugga cggugugcag auccauaggu uugcacccac accaaagccg 9060
uuuuuccggg augaggucuc guucugcguu gggcuuaauu ccuaugcugu cgggucccag 9120
cuucccugug aaccugagcc cgacgcagac guauugaggu ccaugcuaac agauccgccc 9180
cacaucacgg cggagacugc ggcgcggcgc uuggcacggg gaucaccucc aucugaggcg 9240
agcuccucag ugagccagcu aucagcaccg ucgcugcggg ccaccugcac cacccacagc 9300
aacaccuaug acguggacau ggucgaugcc aaccugcuca uggagggcgg uguggcucag 9360
acagagccug aguccagggu gcccguucug gacuuucucg agccaauggc cgaggaagag 9420
agcgaccuug agcccucaau accaucggag ugcaugcucc ccaggagcgg guuuccacgg 9480
gccuuaccgg cuugggcacg gccugacuac aacccgccgc ucguggaauc guggaggagg 9540
ccagauuacc aaccgcccac cguugcuggu ugugcucucc cccccccaa gaaggccccg 9600

-continued acgccucccc caaggagacg ccggacagug ggucugagcg agagcaccau aucagaagcc 9660
cuccagcaac uggccaucaa gaccuuuggc cagcccccu cgagcgguga ugcaggcucg 9720
uccacggggg cgggcgccgc cgaauccggc gguccgacgu ccccugguga gccggccccc 9780
ucagagacag guuccgccuc cucuaugccc ccccucgagg gggagccugg agauccggac 9840
cuggagucug aucagguaga gcuucaaccu cccccccagg ggggggggu agcucccggu 9900
ucgggcucgg ggucuugguc uacuugcucc gaggaggacg auaccaccgu gugcugcucc 9960
augucauacu ccuggaccgg ggcucuaaua acucccugua gccccgaaga ggaaaaguug 10020
ccaaucaacc cuuugaguaa cucgcuguug cgauaccaua acaaggugua cuguacaaca 10080
ucaaagagcg ccucacagag ggcuaaaaag guaacuuuug acaggacgca agugcucgac 10140
gcccauuaug acucagucuu aaaggacauc aagcuagcgg cuuccaaggu cagcgcaagg 10200
cuccucaccu uggaggaggc gugccaguug acuccacccc auucugcaag auccaaguau 10260
ggauucgggg ccaaggaggu ccgcagcuug uccgggaggg ccguuaacca caucaagucc 10320
guguggaagg accuccugga agacccacaa acaccaauuc ccacaaccau cauggccaaa 10380
aaugaggugu ucugcgugga ccccgccaag gggggguaaga aaccagcucg ccucaucguu 10440
uacccugacc ucggcguccg ggucugcgag aaaauggccc ucuaugacau uacacaaaag 10500
cuuccucagg cgguaauggg agcuuccuau ggcuuccagu acuccccugc ccaacgggug 10560
gaguaucucu ugaaagcaug ggcggaaaag aaggacccca ugggguuuuc guaugauacc 10620
cgaugcuucg acucaaccgu cacugagaga gacaucagga ccgaggaguc cauauaccag 10680
gccugcuccc ugcccgagga ggcccgcacu gccauacacu cgcugacuga gagacuuuac 10740
guaggagggc ccauguucaa cagcaagggu caaaccugcg guuacagacg uugccgcgcc 10800
agcggggugc uaaccacuag caugggguaac accaucacau gcuaugugaa agcccuagcg 10860
gccugcaagg cugcggggau aguugcgccc acaaugcugg uaugcggcaa ugaccuagua 10920
gucaucucag aaagccaggg gacugaggag gacgagcgga accugagagc cuucacggag 10980
gccaugacca gguacucugc cccuccuggu gauccccca gaccggaaua ugaccuggag 11040
cuaauaacau ccuguuccuc aaaugugucu guggcguugg gcccgcgggg ccgccgcaga 11100
uacuaccuga ccagagaccc aaccacucca cucgcccggg cugccuggga aacaguuaga 11160
cacuccccua ucaauucaug gcugggaaac aucauccagu augcuccaac cauaugggu 11220
cgcaugguce uaaugacaca cuucuucucc auucucaugg uccaagacac ccuggaccag 11280
aaccucaacu uugagaugua uggaucagua uacuccguga auccuuugga ccuuccagcc 11340
auaauugaga gguuacacgg gcuugacgcc uuuucuaugc acacauacuc ucaccacgaa 11400
cugacgcggg uggcuucagc ccucagaaaa cuuggggcgc caccccucag ggguguggaag 11460
agucgggcuc gcgcagucag ggcgucccuc aucucccgug gagggaaagc ggccguuugc 11520
ggccgauauc ucuucaauug ggcggugaag accaagcuca aacucacucc auugccggag 11580
gcgcgccuac uggacuuauc caguugguuc accgucggcg ccggcggggg cgacauuuuu 11640
cacagcgugu cgcgcgcccg accccgcuca uuacucuucg gccuacuccu acuuuucgua 11700
gggguaggcc ucuuccuacu ccccgcucgg uagagcggca cacacuaggu acacuccaua 11760
gcuaacuguu ccuuuuuuuu uuuuuuuuuu uuuuuuuuuu uuuuuuuuuu uuuuucuuuu 11820
uuuuuuuuuu cccucuuucu ucccuucuca ucuuauucua cuuucuuucu ugguggcucc 11880
aucuuagccc uagucacggc uagcugugaa agguccguga gccgcaugac ugcagagagu 11940
gccguaacug gucucucugc agaucaugu 11969

<210> SEQ ID NO 23
<211> LENGTH: 11036
<212> TYPE: RNA
<213> ORGANISM: Artificial Sequence
<220> FEATURE:
<223> OTHER INFORMATION: replicon RNA derived from the expression
vector rFGR-JFH1/EGFP

<400> SEQUENCE: 23
accugccccu aauaggggcg acacuccgcc augaaucacu ccccugugag gaacuacugu 60
cuucacgcag aaagcgccua gccauggcgu uaguaugagu gucguacagc cuccaggccc 120
cccccucccg ggagagccau aguggucugc ggaaccggug aguacaccgg aauugccggg 180
aagacugggu ccuuucuugg auaaacccac ucuaugcccg gccauuuggg cgugcccccg 240
caagacugcu agccgaguag cguuggguug cgaaaggccu ugugguacug ccugauaggg 300
cgcuugcgag ugccccggga ggucucguag accgugcacc augagcacaa auccuaaacc 360
ucaaagaaaa accaaaagaa acaccaaccg acgcguaaug gugagcaagg gcgaggagcu 420
guucaccggg guggugccca uccuggucga gcuggacggc gacguaaacg gccacaaguu 480
cagcgugucc ggcgagggcg agggcgaugc caccuacggc aagcugaccc ugaaguucau 540
cugcaccacc ggcaagcugc ccgugcccug gcccacccuc gugaccaccc ugaccuacgg 600
cgugcagugc uucagccgcu accccgacca caugaagcag cacgacuucu ucaaguccgc 660
caugcccgaa ggcuacgucc aggagcgcac caucuucuuc aaggacgacg gcaacuacaa 720
gacccgcgcc gaggugaagu ucgagggcga cacccuggug aaccgcaucg agcugaaggg 780
caucgacuuc aaggaggacg gcaacauccu ggggcacaag cuggaguaca acuacaacag 840
ccacaacguc uauaucaugg ccgacaagca gaagaacggc aucaagguga acuucaagau 900
ccgccacaac aucgaggacg gcagcgugca gcucgccgac cacuaccagc agaacacccc 960
caucggcgac ggccccgugc ugcugcccga caaccacuac cugagcaccc aguccgcccu 1020
gagcaaagac cccaacgaga agcgcgauca cauggUccug cuggaguucg ugaccgccgc 1080
cgggaucacu cucggcaugg acgagcugua caaguaaguu uaaacccucu cccucccccc 1140
ccccuaacgu uacuggccga agccgcuugg aauaaggccg gugugcguuu gucuauaugu 1200
uauuuuccac cauauugccg ucuuuuggca augugagggc ccggaaaccu ggcccugucu 1260
ucuugacgag cauuccuagg ggucuuuccc cucucgccaa aggaaugcaa ggucuguuga 1320
augucgugaa ggaagcaguu ccucuggaag cuucuugaag acaaacaacg ucuguagcga 1380
cccuuugcag gcagcggaac cccccaccug gcgacaggug ccucugcggc caaaagccac 1440
guguauaaga uacaccugca aaggcggcac aaccccagug ccacguugug aguuggauag 1500
uuguggaaag agucaaaugg cucuccucaa gcguauucaa caaggggcug aaggaugccc 1560
agaagguacc ccauuguaug ggaucugauc uggggccucg gugcacaugc uuuacaugug 1620
uuuagucgag guuaaaaaaa cgucuaggcc ccccgaacca cggggacgug guuuuccuuu 1680
gaaaaacacg augauaccau gagcacaaau ccuaaaccuc aaagaaaaac caaaagaaac 1740
accaaccguc gcccagaaga cguuaaguuc ccgggcggcg gccagaucgu uggcggagua 1800
uacuuguugc cgcgcagggg ccccagguug ggugugcgca cgacaaggaa aacuucggag 1860 cgguccccagc cacgugggag acgccagccc auccccaaag aucggcgcuc cacuggcaag 1920
gccuggggaa aaccaggucg ccccuggccc cuauauggga augagggacu cggcugggca 1980
ggauggcucc uguccccccg aggcucucgc cccuccuggg gccccacuga cccccggcau 2040

-continued

```
aggucgcgca acgugggguaa agucaucgac acccuaacgu guggcuuugc cgaccucaug   2100
ggguacaucc ccgucguagg cgcccccgcuu aguggcgccg ccagagcugu cgcgcacggc   2160
gugagagucc uggaggacgg gguuaauuau gcaacaggga accuacccgg uuuccccuuu   2220
ucuaucuucu ugcuggcccu guuguccugc aucaccguuc cggucucugc ugcccaggug   2280
aagaauacca guagcagcua cauggugacc aaugacugcu ccaaugacag caucacuugg   2340
cagcucgagg cugcgguucu ccacgucccc gggugcgucc cgugcgagag aguggggaau   2400
acgucacggu guugggugcc agucucgcca aacauggcug ugcggcagcc cggugcccuc   2460
acgcagggguc ugcggacgca caucgauaug guugugaugu ccgccaccuu cugcucugcu   2520
cucuacgugg gggaccucug uggcggggug augcucgcgg cccagguguu caucgucucg   2580
ccgcaguacc acugguuugu gcaagaaugc aauugcucca ucuacccugg caccaucacu   2640
ggacaccgca uggcauggga caugaugaug aacuggucgc ccacggccac caugauccug   2700
gcguacguga ugcgcguccc cgaggucauc auagacaucg uuagcggggc ucacuggggc   2760
gucauguucg gcuuggccua cuucucuaug cagggagcgu gggcgaaggu cauugucauc   2820
cuucugcugg ccgcuggggu ggacgcgggc accaccaccg uuggaggcgc uguugcacgu   2880
uccaccaacg ugauugccgg cguguucagc cauggcccuc agcagaacau ucagcucauu   2940
aacaccaacg gcaguuggca caucaaccgu acugccuuga auugcaauga cucccuugaac   3000
accggcuuuc ucgcggccuu guucuacacc aaccgcuuua acucgucagg guguccaggg   3060
cgccuguccg ccugccgcaa caucgaggcu uuccggauag ggugggggcac ccuacaguac   3120
gaggauaaug ucaccaaucc agaggauaug aggccguacu gcuggcacua ccccccaaag   3180
ccguguggcg uagucccccgc gaggucugug uguggcccag uguacuguuu cacccccagc   3240
ccgguaguag ugggcacgac cgacagacgu ggagugccca ccuacacaug ggagagagau   3300
gagacagaug ucuuccuacu gaacagcacc cgaccgccgc agggcucaug guucggcugc   3360
acguggauga acuccacugg uuucaccaag acuuguggcg cgccaccuug ccgcaccaga   3420
gcugacuuca acgccagcac ggacuuguug ugcccuacgg auuguuuuag gaagcauccu   3480
gaugccacuu auauuaagug ugguucuggg cccuggcuca caccaaagug ccugguccac   3540
uacccuuaca gacucuggca uuacccccugc acagucaauu uuaccaucuu caagauaaga   3600
auguauguag gggggguuga gcacaggcuc acggccgcau gcaacuucac ucgugggggau   3660
cgcugcgacu uggaggacag ggacaggagu cagcugucuc cucuguugca cucuaccacg   3720
gaaugggcca uccugcccug caccuacuca gacuuacccg cuuugucaac ugguucuucuc   3780
caccuucacc agaacaucgu ggacguacaa uacauguaug gccucucacc ugcuaucaca   3840
aaauacgucg uucgauggga gugggguggua cucuuauucc ugcucuuagc ggacgccaga   3900
gucugcgccu gcuuguggau gcucaucuug uugggccagg ccgaagcagc auuggagaag   3960
uuggucgucu ugcacgcugc gagugcggcu aacugccaug gccuccuaua uuuugccauc   4020
uucuucgugg cagcuuggca caucaggggu cgggguggucc ccuugaccac cuauugccuc   4080
acuggccuau ggcccuucug ccuacugcuc auggcacugc cccggcaggc uuaugccuau   4140
gacgcaccug ugcacggaca gauaggcgug gguuuguuga uauugaucac ccucuucaca   4200
cucaccccgg gguauaagac ccuccucggc cagugucugu ggugguugug cuaucuccug   4260
acccuggggg aagccaugau ucaggagugg guaccaccca ugcaggugcg cggcggccgc   4320
gauggcaucg cgugggccgu cacuauauuc ugcccgggug ugguguuuga cauuaccaaa   4380
uggcuuuugg cguugcuugg gccugcuuac cucuuaaggg ccgcuuugac acaugugccg   4440
```

-continued

```
uacuucguca gagcucacgc ucugauaagg guaugcgcuu uggugaagca gcucgcgggg   4500
gguagguaug uucagguggc gcuauuggcc cuuggcaggu ggacuggcac cuacaucuau   4560
gaccaccuca caccuauguc ggacugggcc gcuagcggcc ugcgcgacuu agcggucgcc   4620
guggaaccca ucaucuucag uccgauggag aagaagguca ucgucugggg agcggagacg   4680
gcugcaugug gggacauucu acauggacuu cccguguccg cccgacucgg ccaggagauc   4740
cuccucggcc cagcugaugg cuacaccucc aaggggugga agcuccuugc ucccaucacu   4800
gcuuaugccc agcaaacacg aggccuccug ggcgccauag uggugaguau gacggggcgu   4860
gacaggacag aacaggccgg ggaaguccaa auccugucca cagucucuca guccuuccuc   4920
ggaacaacca ucucgggggu uuuguggacu guuuaccacg gagcuggcaa caagacucua   4980
gccggcuuac ggggucoggu cacgcagaug uacucgagug cugaggggga cuugguaggc   5040
uggcccagcc ccccugggac caagucuuug gagccgugca aguguggagc cgucgaccua   5100
uaucugguca cgcggaacgc ugaugucauc ccggcucgga gacgcgggga caagcgggga   5160
gcauugcucu ccccgagacc cauuucgacc uugaaggggu ccucgggggg gccggugcuc   5220
ugcccuaggg gccacgucgu ugggcucuuc cgagcagcug ugugcucucg ggcgguggcc   5280
aaauccaucg auuucauccc cguugagaca cucgacguug uuacaagguc ucccacuuuc   5340
agugacaaca gcacgccacc ggcugugccc cagaccuauc aggucgggua cuugcaugcu   5400
ccaacuggca guggaaagag caccaagguc ccugucgcgu augccgccca gggguacaaa   5460
guacuagugc uuaaccccuc gguagcugcc acccuggggu uuggggcgua ccuauccaag   5520
gcacauggca ucaaucccaa cauuaggacu ggagucagga ccgugaugac cggggaggcc   5580
aucacguacu ccacauaugg caaauuucuc gccgaugggg gcugcgcuag cggcgccuau   5640
gacaucauca uaugcgauga augccacgcu guggaugcua ccuccauucu cggcaucgga   5700
acgguccuug aucaagcaga gacagccggg gucagacuaa cugugcuggc uacggccaca   5760
ccccccgggu cagugacaac ccccccaucccc gauauagaag agguaggccu cgggcgggag   5820
ggugagaucc ccuucuaugg gagggcgauu ccccuauccu gcaucaaggg agggagacac   5880
cugauuuucu gccacucaaa gaaaaagugu gacgagcucg cggcggcccu ucggggcaug   5940
ggcuugaaug ccguggcaua cuauagaggg uuggacgucu ccauaaauacc agcucaggga   6000
gauguggugg ucgucgccac cgacgcccuc augacggggu acacuggaga cuuugacucc   6060
gugaucgacu gcaauguagc ggucacccaa gcugucgacu ucagccugga ccccaccuuc   6120
acuauaacca cacagacugu cccacaagac gcugucucac gcagucagcg ccgcgggcgc   6180
acagguagag gaagacaggg cacuuauagg uauguuucca cuggugaacg agccucagga   6240
auguuugaca guguagugcu uugugagugc uacgacgcag ggcugcgug guacgaucuc   6300
acaccagcgg agaccaccgu caggcuuaga gcguauuuca acacgcccgg ccuacccgug   6360
ugucaagacc aucuugaauu uugggaggca guuuucaccg gccucacaca cauagacgcc   6420
cacuuccucu cccaaacaaa gcaagcgggg gagaacuucg cguaccuagu agccuaccaa   6480
gcuacggugu gcgccagagc caaggccccu cccccguccu gggacgccau guggaagugc   6540
cuggcccgac ucaagccuac gcuugcgggc cccacaccuc uccuguaccg uuugggcccu   6600
auuaccaaug aggucacccu cacacacccu gggacgaagu acaucgccac augcaugcaa   6660
gcugaccuug aggucaugac cagcacgugg guccuagcug gaggaguccu ggcagccguc   6720
gccgcauauu gccuggcgac uggaugcguu uccaucaucg gccgcuugca cgucaaccag   6780
cgagucgucg uugcgccgga uaaggagguc cuguaugagg cuuuugauga gauggaggaa   6840
```

-continued ugcgccucua gggcggcucu caucgaagag gggcagcgga uagccgagau guugaagucc 6900
aagauccaag gcuugcugca gcaggccucu aagcaggccc aggacauaca acccgcuaug 6960
caggcuucau ggcccaaagu ggaacaauuu ugggccagac acauguggaa cuucauuagc 7020
ggcauccaau accucgcagg auugucaaca cugccaggga accccgcggu ggcuuccaug 7080
auggcauuca gugccgcccu caccaguccg uugucgacca guaccaccau ccuucucaac 7140
aucaugggag gcugguuagc gucccagauc gcaccacccg cgggggccac cggcuuuguc 7200
gucaguggcc uggugggggc ugccgugggc agcauaggcc uggguaaggu gcugguggac 7260
auccuggcag gauauggugc gggcauuucg ggggcccucg ucgcauucaa gaucaugucu 7320
ggcgagaagc ccucuaugga agaugucauc aaucuacugc cugggauccu gucuccggga 7380
gcccuggugg ugggggucau cugcgcggcc auucugcgcc gccacguggg accgggggag 7440
ggcgcggucc aauggaugaa caggcuuauu gccuuugcuu ccagaggaaa ccacgucgcc 7500
ccuacucacu acgugacgga gucggaugcg ucgcagcgug ugacccaacu acuuggcucu 7560
cuuacuauaa ccagccuacu cagaagacuc cacaauugga uaacugagga cugccccauc 7620
ccaugcuccg gauccuggcu ccgcgacgug ugggacuggg uuugcaccau cuugacagac 7680
uucaaaaauu ggcugaccuc uaaauuguuc cccaagcugc ccggccuccc cuucaucucu 7740
ugucaaaagg gguacaaggg ugugugggcc ggcacuggca ucaugaccac gcgcugcccu 7800
ugcggcgcca acaucucugg caauguccgc cugggcucua ugaggaucac agggccuaaa 7860
accugcauga acaccuggca ggggaccuuu ccuaucaauu gcuacacgga gggccagugc 7920
gcgccgaaac cccccacgaa cuacaagacc gccaucugga ggguggcggc cucggaguac 7980
gcggagguga cgcagcaugg gucguacucc uauguaacag gacugaccac ugacaaucug 8040
aaaauuccuu gccaacuacc uucuccagag uuuuucuccu ggguggacgg ugugcagauc 8100
cauagguuug cacccacacc aaagccguuu uuccgggaug aggucucguu cugcguuggg 8160
cuuaauuccu augcugucgg gucccagcuu cccugugaac cugagcccga cgcagacgua 8220
uugaggucca ugcuaacaga uccgccccac aucacggcgg agacugcggc gcggcgcuug 8280
gcacggggau caccuccauc ugaggcgagc uccucaguga gccagcuauc agcaccgucg 8340
cugcgggcca ccugcaccac ccacagcaac accuaugacg uggacauggu cgaugccaac 8400
cugcucaugg agggcggugu ggcucagaca gagccugagu ccagggugcc cguucuggac 8460
uuucucgagc caauggccga ggaagagagc gaccuugagc ccucaauacc aucggagugc 8520
augcucccca ggagcggguu uccacgggcc uuaccggcuu gggcacggcc ugacuacaac 8580
ccgccgcucg uggaaucgug gaggaggcca gauuaccaac cgcccaccgu ugcugguugu 8640
gcucuccccc cccccaagaa ggccccgacg ccucccccaa ggagacgccg gacagugggu 8700
cugagcgaga gcaccauauc agaagcccuc cagcaacugg ccaucaagac cuuuggccag 8760
ccccccucga gcggugaugc aggcucgucc acgggggcgg gcgccgccga auccggcggu 8820
ccgacguccc cuggugagcc ggcccccuca gagacagguu ccgccuccuc uaugcccccc 8880
cucgaggggg agccuggaga uccggaccug gagucugauc agguagagcu ucaaccuccc 8940
ccccaggggg ggggggguagc ucccgguucg ggcucggggu cuuggucuac uugcuccgag 9000
gaggacgaua ccaccgugug cugcuccaug ucauacuccu ggaccggggc ucuaauaacu 9060
cccuguagcc ccgaagagga aaaguugcca aucaacccuu ugaguaacuc gcuguugcga 9120
uaccauaaca agguguacug uacaacauca aagagcgccu cacagagggc uaaaaaggua 9180
acuuuugaca ggacgcaagu gcucgacgcc cauuaugacu cagucuuaaa ggacaucaag 9240

```
cuagcggcuu ccaaggucag cgcaaggcuc cucaccuugg aggaggcgug ccaguugacu   9300
ccaccccauu cugcaagauc caaguaugga uucggggcca aggagguccg cagcuugucc   9360
gggagggccg uuaaccacau caaguccgug uggaaggacc uccuggaaga cccacaaaca   9420
ccaauuccca caaccaucau ggccaaaaau gagguguucu gcguggaccc cgccaagggg   9480
gguaagaaac cagcucgccu caucguuuac ccugaccucg gcguccgggu cugcgagaaa   9540
auggcccucu augacauuac acaaaagcuu ccucaggcgg uaaugggagc uuccuauggc   9600
uuccaguacu ccccugccca acgggguggag uaucucuuga aagcaugggc ggaaaagaag   9660
gaccccaugg guuuuucgua ugauacccga ugcuucgacu caaccgucac ugagagagac   9720
aucaggaccg aggaguccau auaccaggcc ugcucccugc ccgaggaggc ccgcacugcc   9780
auacacucgc ugacugagag acuuuacgua ggagggccca uguucaacag caagggucaa   9840
accugcgguu acagacguug ccgcgccagc ggggugcuaa ccacuagcau ggguaacacc   9900
aucacaugcu augugaaagc ccuagcggcc ugcaaggcug cggggauagu ugcgccccaca   9960
augcugguau gcggcgauga ccuaguaguc aucucagaaa gccaggggac ugaggaggac  10020
gagcggaacc ugagagccuu cacggaggcc augaccaggu acucugcccc uccuggugau  10080
ccccccagac cggaauauga ccuggagcua auaaacaucu guuccucaaa ugugucugug  10140
gcguugggcc cgcggggccg ccgcagauac uaccugacca gagacccaac cacuccacuc  10200
gcccgggcug ccugggaaac aguuagacac uccccuauca auucauggcu gggaaacauc  10260
auccaguaug cuccaaccau augguucgc augguccuaa ugacacacuu cuucuccauu  10320
cucauggucc aagacacccu ggaccagaac cucaacuuug agauguaugg aucaguauac  10380
uccgugaauc cuuuggaccu uccagccaua auugagaggu uacacgggcu ugacgccuuu  10440
ucuaugcaca cauacucuca ccacgaacug acgcgggugg cuucagcccu cagaaaacuu  10500
ggggcgccac cccucagggu guggaagagu cgggcucgcg cagucagggc gucccucauc  10560
ucccguggag ggaaagcggc cguuugcggc cgauaucucu ucaauugggc ggugaagacc  10620
aagcucaaac ucacuccauu gccggaggcg cgccuacugg acuuauccag uugguucacc  10680
gucggcgccg gcgggggcga cauuuuucac agcgugucgc gcgcccgacc ccgcucauua  10740
cucuucggcc uacuccuacu uuucguaggg guaggccucu uccuacuccc cgcucgguag  10800
agcggcacac acuagguaca cuccauagcu aacuguuccu uuuuuuuuuu uuuuuuuuuu  10860
uuuuuuuuuu uuuuuuuuuu uucuuuuuuu uuuuuuuccc ucuuucuucc cuucucaucu  10920
uauucuacuu ucuuucuugg uggcuccauc uuagcccuag ucacggcuag cugugaaagg  10980
uccgugagcc gcaugacugc agagagugcc guaacugguc ucucugcaga ucaugu      11036
```

```
<210> SEQ ID NO 24
<211> LENGTH: 11036
<212> TYPE: RNA
<213> ORGANISM: Artificial Sequence
<220> FEATURE:
<223> OTHER INFORMATION: replicon RNA derived from the expression vector
      rFGR-JFH1/EGFP/GND

<400> SEQUENCE: 24
```

```
accugccccu aauaggggcg acacuccgcc augaaucacu ccccugugag gaacuacugu     60
cuucacgcag aaagcgccua gccauggcgu uaguaugagu gucguacagc cuccaggccc    120
ccccucccg ggagagccau aguggucugc ggaaccggug aguacaccgg aauugccggg    180
aagacugggu ccuuucuugg auaaacccac ucuaugcccg gccauuuggg cgugcccccg    240
caagacugcu agccgaguag cguuggguug cgaaaggccu ugugguacug ccugauaggg    300
```

-continued

```
cgcuugcgag ugccccggga ggucucguag accgugcacc augagcacaa auccuaaacc    360
ucaaagaaaa accaaaagaa acaccaaccg acgcguaaug gugagcaagg gcgaggagcu    420
guucaccggg guggugccca uccuggucga gcuggacggc gacguaaacg gccacaaguu    480
cagcgugucc ggcgagggcg agggcgaugc caccuacggc aagcugaccc ugaaguucau    540
cugcaccacc ggcaagcugc ccgugcccug gcccacccuc gugaccaccc ugaccuacgg    600
cgugcagugc uucagccgcu accccgacca caugaagcag cacgacuucu ucaaguccgc    660
caugcccgaa ggcuacgucc aggagcgcac caucuucuuc aaggacgacg gcaacuacaa    720
gacccgcgcc gaggugaagu ucgagggcga cacccuggug aaccgcaucg agcugaaggg    780
caucgacuuc aaggaggacg gcaacauccu ggggcacaag cuggaguaca acuacaacag    840
ccacaacguc uauaucaugg ccgacaagca gaagaacggc aucaagguga acuucaagau    900
ccgccacaac aucgaggacg gcagcgugca gcucgccgac cacuaccagc agaacacccc    960
caucggcgac ggccccgugc ugcugcccga caaccacuac cugagcaccc aguccgcccu   1020
gagcaaagac cccaacgaga agcgcgauca cauggucug cuggaguucg ugaccgccgc   1080
cgggaucacu cucggcaugg acgagcugua caaguaaguu uaaacccucu cccucccccc   1140
ccccuaacgu uacuggccga agccgcuugg aauaaggccg gugugcguuu gucuauaugu   1200
uauuuuccac cauauugccg ucuuuuggca augugagggc ccggaaaccu ggcccugucu   1260
ucuugacgag cauuccuagg ggucuuuccc cucucgccaa aggaaugcaa ggucuguuga   1320
augucgugaa ggaagcaguu ccucuggaag cuucuugaag acaaacaacg ucuguagcga   1380
cccuuugcag gcagcggaac cccccaccug gcgacaggug ccucugcggc caaaagccac   1440
guguauaaga uacaccugca aaggcggcac aaccccagug ccacguugug aguuggauag   1500
uuguggaaag agucaaaugg cucuccucaa gcguauucaa caaggggcug aaggaugccc   1560
agaagguacc ccauuguaug ggaucugauc uggggccucg gugcacaugc uuuacaugug   1620
uuuagucgag guuaaaaaaa cgucuaggcc ccccgaacca cggggacgug guuuuccuuu   1680
gaaaaacacg augauaccau gagcacaaau ccuaaaccuc aaagaaaaac caaaagaaac   1740
accaaccguc gcccagaaga cguuaaguuc ccgggcggcg gccagaucgu uggcggagua   1800
uacuuguugc cgcgcagggg ccccagguug ggugugcgca cgacaaggaa aacuucggag   1860
cggucccagc cacgugggag acgccagccc auccccaaag aucggcgcuc cacuggcaag   1920
gccuggggaa aaccaggucg ccccuggccc cuauauggga augagggacu cggcugggca   1980
ggauggcucc uguccccccg aggcucucgc cccuccuggg gccccacuga cccccggcau   2040
aggucgcgca acgugggusaa agucaucgac acccuaacgu guggcuuugc cgaccucaug   2100
ggguacaucc ccgucguagg cgccccgcuu aguggcgccg ccagagcugu cgcgcacggc   2160
gugagagucc uggaggacgg gguuaauuau gcaacaggga accuacccgg uuuccccuuu   2220
ucuaucuucu ugcuggcccu guuguccugc aucaccguuc cggucucugc ugcccaggug   2280
aagaauacca guagcagcua cauggugacc aaugacugcu ccaaugacag caucacuugg   2340
cagcucgagg cugcgguucu ccacgucccc gggugcgucc cgugcgagag aguggggaau   2400
acgucacggu guugggugcc agucucgcca aacauggcug ugcggcagcc cggugcccuc   2460
acgcaggguc ugcggacgca caucgauaug guugugaugu ccgccaccuu cugcucugcu   2520
cucuacgugg gggaccucug uggcggggug augcucgcgg cccaggugu caucgucucg   2580
ccgcaguacc acugguuugu gcaagaaugc aauugcucca ucuacccugg caccaucacu   2640
ggacaccgca uggcauggga caugaugaug aacuggucgc ccacggccac caugauccug   2700
```

gcguacguga ugcgcguccc cgaggucauc auagacaucg uuagcggggc ucacuggggc 2760
gucauguucg gcuuggccua cuucucuaug cagggagcgu gggcgaaggu cauugucauc 2820
cuucugcugg ccgcuggggu ggacgcgggc accaccaccg uuggaggcgc uguugcacgu 2880
uccaccaacg ugauugccgg cguguucagc cauggcccuc agcagaacau ucagcucauu 2940
aacaccaacg gcaguuggca caucaaccgu acugccuuga auugcaauga cuccuugaac 3000
accggcuuuc ucgcggccuu guucuacacc aaccgcuuua acucgucagg guguccaggg 3060
cgccuguccg ccugccgcaa caucgaggcu uuccggauag ggugggggcac ccuacaguac 3120 gaggauaaug ucaccaaucc agaggauaug aggccguacu gcuggcacua ccccccaaag 3180
ccguguggcg uaguccccgc gaggucugug uguggcccag uguacuguuu cacccccagc 3240
ccgguaguag ugggcacgac cgacagacgu ggagugccca ccuacacaug ggagagagau 3300
gagacagaug ucuuccuacu gaacagcacc cgaccgccgc agggcucaug guucggcugc 3360
acguggauga acuccacugg uuucaccaag acuuguggcg cgccaccuug ccgcaccaga 3420
gcugacuuca acgccagcac ggacuuguug ugcccuacgg auuguuuuag gaagcauccu 3480
gaugccacuu auauuaagug ugguucuggg cccuggcuca caccaaagug ccugguccac 3540
uacccuuaca gacucuggca uuaccccugc acagucaauu uuaccaucuu caagauaaga 3600
auguauguag ggggguuga gcacaggcuc acggccgcau gcaacuucac ucguggggau 3660
cgcugcgacu uggaggacag ggacaggagu cagcugucuc cucuguugca cucuaccacg 3720
gaaugggcca uccugcccug caccuacuca gacuuacccg cuuugucaac uggucuucuc 3780
caccuucacc agaacaucgu ggacguacaa uacauguaug gccucucacc ugcuaucaca 3840
aaauacgucg uucgauggga gugggguggua cucuuauucc ugcucuuagc ggacgccaga 3900
gucugcgccu gcuuguggau gcucaucuug uugggccagg ccgaagcagc auuggagaag 3960
uuggucgucu ugcacgcugc gagugcggcu aacugccaug gccuccuaua uuuugccauc 4020
uucuucgugg cagcuuggca caucaggggu cgggugguccc ccuugaccac cuauugccuc 4080
acuggccuau ggcccuucug ccuacugcuc auggcacugc cccggcaggc uuaugccuau 4140
gacgcaccug ugcacggaca gauaggcgug gguuuguuga uauugaucac ccucuucaca 4200
cucaccccgg gguauaagac ccuccucggc cagugucugu ggugguugug cuaucuccug 4260
acccuggggg aagccaugau ucaggagugg guaccaccca ugcaggugcg cggcggccgc 4320
gauggcaucg cgugggccgu cacuauauuc ugcccgggug ugguguuuga cauuaccaaa 4380
uggcuuuugg cguugcuugg gccugcuuac cucuuaaggg ccgcuuugac acaugugccg 4440
uacuucguca gagcucacgc ucugauaagg guaugcgcuu uggugaagca gcucgcgggg 4500
gguagguaug uucagguggc gcuauuggcc cuuggcaggu ggacuggcac cuacaucuau 4560
gaccaccuca caccuauguc ggacugggcc gcuagcggcc ugcgcgacuu agcggucgcc 4620
guggaaccca ucaucuucag uccgauggag aagaagguca ucgucugggg agcggagacg 4680
gcugcaugug gggacauucu acauggacuu cccguguccg cccgacucgg ccaggagauc 4740
cuccucggcc cagcugaugg cuacaccucc aaggggugga agcuccuugc ucccaucacu 4800
gcuuaugccc agcaaacacg aggccuccug ggcgccauag uggugaguau gacggggcgu 4860
gacaggacag aacaggccgg ggaaguccaa auccugucca cagucucuca guccuuccuc 4920
ggaacaacca ucucgggggu uuuguggacu guuuaccacg gagcuggcaa caagacucua 4980
gccggcuuac gggguccggu cacgcagaug uacucgagug cugaggggga cuugguaggc 5040
uggcccagcc ccccugggac caagucuuug gagccgugca aguguggagc cgucgaccua 5100
uaucugguca cgcggaacgc ugaugucauc ccggcucgga gacgcgggga caagcgggga 5160
gcauugcucu ccccgagacc cauuucgacc uugaaggggu ccucgggggg gccggugcuc 5220
ugcccuaggg gccacgucgu ugggcucuuc cgagcagcug ugugcucucg gggcguggcc 5280
aaauccaucg auuucauccc cguugagaca cucgacguug uuacaagguc ucccacuuuc 5340
agugacaaca gcacgccacc ggcugugccc cagaccuauc aggucgggua cuugcaugcu 5400
ccaacuggca guggaaagag caccaagguc ccugucgcgu augccgccca gggguacaaa 5460
guacuagugc uuaaccccuc gguagcugcc acccuggggu uuggggcgua ccuauccaag 5520
gcacauggca ucaaucccaa cauuaggacu ggagucagga ccgugaugac cggggaggcc 5580
aucacguacu ccacauaugg caaauuucuc gccgaugggg gcugcgcuag cggcgccuau 5640
gacaucauca uaugcgauga augccacgcu guggaugcua ccuccauucu cggcaucgga 5700
acgguccuug aucaagcaga gacagccggg gucagacuaa cugugcuggc uacggccaca 5760
cccccgggu cagugacaac cccccauccc gauauagaag agguaggccu cgggcgggag 5820
ggugagaucc ccuucuaugg gagggcgauu ccccuauccu gcaucaaggg agggagacac 5880
cugauuuucu gccacucaaa gaaaaagugu gacgagcucg cggcggcccu ucggggcaug 5940
ggcuugaaug ccguggcaua cuauagaggg uuggacgucu ccauaauacc agcucaggga 6000
gauguggugg ucgucgccac cgacgcccuc augacggggu acacuggaga cuuugacucc 6060
gugaucgacu gcaauguagc ggucacccaa gcugucgacu ucagccugga ccccaccuuc 6120
acuauaacca cacagacugu cccacaagac gcugucucac gcagucagcg ccgcgggcgc 6180
acagguagag gaagacaggg cacuuauagg uauguuucca cuggugaacg agccucagga 6240
auguuugaca guguagugcu uugugagugc uacgacgcag ggcugcgug guacgaucuc 6300
acaccagcgg agaccaccgu caggcuuaga gcguauuuca acacgcccgg ccuacccgug 6360
ugucaagacc aucuugaauu uugggaggca guuuucaccg gccucacaca cauagacgcc 6420
cacuuccucu cccaaacaaa gcaagcgggg gagaacuucg cguaccuagu agccuaccaa 6480
gcuacggugu gcgccagagc caaggccccu cccccguccu gggacgccau guggaagugc 6540
cuggcccgac ucaagccuac gcuugcgggc cccacaccuc uccuguaccg uuugggcccu 6600
auuaccaaug aggucacccu cacacacccu gggacgaagu acaucgccac augcaugcaa 6660
gcugaccuug aggucaugac cagcacgugg guccuagcug gaggaguccu ggcagccguc 6720
gccgcauauu gccuggcgac uggaugcguu uccaucaucg gccgcuugca cgucaaccag 6780
cgagucgucg uugcgccgga uaaggagguc cuguaugagg cuuuugauga gauggaggaa 6840
ugcgccucua gggcggcucu caucgaagag gggcagcgga uagccgagau guugaagucc 6900
aagauccaag gcuugcugca gcaggccucu aagcaggccc aggacauaca acccgcuaug 6960
caggcuucau ggcccaaagu ggaacaauuu ugggccagac acauguggaa cuucauuagc 7020
ggcauccaau accucgcagg auugucaaca cugccaggga accccgcggu ggcuuccaug 7080
auggcauuca gugccgcccu caccaguccg uugucgacca guaccaccau ccuucucaac 7140
aucaugggag gcugguuagc gucccagauc gcaccacccg cgggggccac cggcuuuguc 7200
gucaguggcc ugguggggc ugccgugggc agcauaggcc uggguaaggu gcugguggac 7260
auccuggcag gauauggugc gggcauuucg ggggcccucg ucgcauucaa gaucaugucu 7320
ggcgagaagc ccucuaugga agaugucauc aaucuacugc cugggauccu gucuccggga 7380
gcccuggugg ugggggucau cugcgcggcc auucugcgcc gccacguggg accgggggag 7440
ggcgcggucc aauggaugaa caggcuuauu gccuuugcuu ccagaggaaa ccacgucgcc 7500
ccuacucacu acgugacgga gucggaugcg ucgcagcgug ugacccaacu acuuggcucu 7560
cuuacuauaa ccagccuacu cagaagacuc cacaauugga uaacugagga cugccccauc 7620
ccaugcuccg gauccuggcu ccgcgacgug ugggacuggg uuugcaccau cuugacagac 7680
uucaaaaauu ggcugaccuc uaaauuguuc cccaagcugc ccggccuccc cuucaucucu 7740
ugucaaaagg gguacaaggg ugugugggcc ggcacuggca ucaugaccac gcgcugcccu 7800
ugcggcgcca acaucucugg caauguccgc cugggcucua ugaggaucac agggccuaaa 7860
accugcauga acaccuggca ggggaccuuu ccuaucaauu gcuacacgga gggccagugc 7920
gcgccgaaac cccccacgaa cuacaagacc gccaucugga gggguggcgc cucggaguac 7980
gcggagguga cgcagcaugg gucguacucc uauguaacag gacugaccac ugacaaucug 8040
aaaauuccuu gccaacuacc uucuccagag uuuuucuccu ggguggacgg ugugcagauc 8100
cauagguuug cacccacacc aaagccguuu uuccgggaug aggucucguu cugcguuggg 8160
cuuaauuccu augcugucgg gucccagcuu cccugugaac cugagcccga cgcagacgua 8220
uugaggucca ugcuaacaga uccgccccac aucacggcgg agacugcggc gcggcgcuug 8280
gcacggggau caccuccauc ugaggcgagc uccucaguga gccagcuauc agcaccgucg 8340
cugcgggcca ccugcaccac ccacagcaac accuaugacg uggacauggu cgaugccaac 8400
cugcucaugg agggcggugu ggcucagaca gagccugagu ccagggugcc cguucuggac 8460
uuucucgagc caauggccga ggaagagagc gaccuugagc ccucaauacc aucggagugc 8520
augcucccca ggagcggguu uccacgggcc uuaccggcuu gggcacggcc ugacuacaac 8580
ccgccgcucg uggaaucgug gaggaggcca gauuaccaac cgcccaccgu ugcugguugu 8640
gcucuccccc cccccaagaa ggccccgacg ccucccccaa ggagacgccg gacagugggu 8700
cugagcgaga gcaccauauc agaagcccuc cagcaacugg ccaucaagac cuuuggccag 8760
ccccccucga gcggugaugc aggcucgucc acgggggcgg gcgccgccga auccggcggu 8820
ccgacguccc cuggugagcc ggcccccuca gagacagguu ccgccuccuc uaugcccccc 8880
cucgaggggg agccuggaga uccggaccug gagucugauc agguagagcu ucaaccuccc 8940
ccccaggggg gggggguagc ucccgguucg ggcucggggu cuuggucuac uugcuccgag 9000
gaggacgaua ccaccgugug cugcuccaug ucauacuccu ggaccggggc ucuaauaacu 9060
cccuguagcc ccgaagagga aaaguugcca aucaacccuu ugaguaacuc gcuguugcga 9120
uaccauaaca agguguacug uacaacauca aagagcgccu cacagagggc uaaaaaggua 9180
acuuugaca ggacgcaagu gcucgacgcc cauuaugacu cagucuuaaa ggacaucaag 9240
cuagcggcuu ccaaggucag cgcaaggcuc cucaccuugg aggaggcgug ccaguugacu 9300
ccaccccauu cugcaagauc caaguaugga uucggggcca aggagguccg cagcuugucc 9360
gggagggccg uuaaccacau caaguccgug uggaaggacc uccuggaaga cccacaaaca 9420
ccaauuccca caaccaucau ggccaaaaau gaggugunucu gcguggaccc cgccaagggg 9480
gguaagaaac cagcucgccu caucguuuac ccugaccucg gcguccgggu cugcgagaaa 9540
auggcccucu augacauuac acaaaagcuu ccucaggcgg uaaugggagc uuccuauggc 9600
uuccaguacu ccccugccca acggguggag uaucucuuga aagcaugggc ggaaaagaag 9660
gaccccaugg guuuuucgua ugauacccga ugcuucgacu caaccgucac ugagagagac 9720
aucaggaccg aggaguccau auaccaggcc ugcucccugc ccgaggaggc ccgcacugcc 9780
auacacucgc ugacugagag acuuuacgua ggagggccca uguucaacag caagggucaa 9840
accugcgguu acagacguug ccgcgccagc ggggugcuaa ccacuagcau ggguaacacc 9900

-continued aucacaugcu augugaaagc ccuagcggcc ugcaaggcug cggggauagu ugcgcccaca 9960
augcugguau gcggcaauga ccuaguaguc aucucagaaa gccaggggac ugaggaggac 10020
gagcggaacc ugagagccuu cacggaggcc augaccaggu acucugcccc uccuggugau 10080
ccccccagac cggaauauga ccuggagcua auaacauccu guuccucaaa ugugucugug 10140
gcguugggcc cgcggggccg ccgcagauac uaccugacca gagacccaac cacuccacuc 10200
gcccgggcug ccugggaaac aguuagacac uccccuauca auucauggcu gggaaacauc 10260
auccaguaug cuccaaccau auggguucgc augguccuaa ugacacacuu cuucuccauu 10320
cucauggucc aagacacccu ggaccagaac cucaacuuug agauguaugg aucaguauac 10380
uccgugaauc cuuuggaccu uccagccaua auugagaggu uacacgggcu ugacgccuuu 10440
ucuaugcaca cauacucuca ccacgaacug acgcgggugg cuucagcccu cagaaaacuu 10500
ggggcgccac cccucagggu guggaagagu cgggcucgcg cagucagggc gucccucauc 10560
ucccguggag ggaaagcggc cguuugcggc cgauaucucu ucaauugggc ggugaagacc 10620
aagcucaaac ucacuccauu gccggaggcg cgccuacugg acuuauccag uugguucacc 10680
gucggcgccg gcgggggcga cauuuuucac agcgugucgc gcgcccgacc ccgcucauua 10740
cucuucggcc uacuccuacu uuucguaggg guaggccucu uccuacuccc cgcucgguag 10800
agcggcacac acuagguaca cuccauagcu aacuguuccu uuuuuuuuuu uuuuuuuuuu 10860
uuuuuuuuuu uuuuuuuuuu uucuuuuuuu uuuuuuuccc ucuuucuucc cuucucaucu 10920
uauucuacuu ucuuucuugg uggcuccauc uuagcccuag ucacggcuag cugugaaagg 10980
uccgugagcc gcaugacugc agagagugcc guaacugguc ucucugcaga ucaugu 11036

<210> SEQ ID NO 25
<211> LENGTH: 11876
<212> TYPE: RNA
<213> ORGANISM: Artificial Sequence
<220> FEATURE:
<223> OTHER INFORMATION: replicon RNA derived from the expression vector rFGR-JFH1/SEAP

<400> SEQUENCE: 25
accugccccu aauaggggcg acacuccgcc augaaucacu ccccugugag gaacuacugu 60
cuucacgcag aaagcgccua gccauggcgu uaguaugagu gucguacagc cuccaggccc 120
cccccucccg ggagagccau aguggucugc ggaaccggug aguacaccgg aauugccggg 180
aagacugggu ccuuucuugg auaaacccac ucuaugcccg gccauuuggg cgugcccccg 240
caagacugcu agccgaguag cguuggguug cgaaaggccu ugugguacug ccugauaggg 300
cgcuugcgag ugccccggga ggucucguag accgugcacc augagcacaa auccuaaacc 360
ucaaagaaaa accaaaagaa acaccaaccg acgcguaaug cugcugcugc ugcugcugcu 420
gggccugagg cuacagcucu cccugggcau caucccaguu gaggaggaga acccggacuu 480
cuggaaccgc gaggcagccg aggcccuggg ugccgccaag aagcugcagc cugcacagac 540
agccgccaag aaccucauca ucuuccuggg cgaugggaug ggggugucua cggugacagc 600
ugccaggauc cuaaaagggc agaagaagga caaacugggg ccugagauac cccuggccau 660
ggaccgcuuc ccauaugugg cucuguccaa gacauacaau guagacaaac augugccaga 720
caguggagcc acagccacgg ccuaccugug cggggucaag ggcaacuucc agaccauugg 780
cuugagugca gccgcccgcu uuaaccagug caacacgaca cgcggcaacg aggucaucuc 840
cgugaugaau cgggccaaga aagcagggaa gucaguggga gugguaacca ccacacgagu 900

-continued

```
gcagcacgcc ucgccagccg gcaccuacgc ccacacggug aaccgcaacu gguacucgga    960
cgccgacgug ccugccucgg cccgccagga ggggugccag gacaucgcua cgcagcucau   1020
cuccaacaug gacauugacg ugauccuagg uggaggccga aaguacaugu uucgcauggg   1080
aaccccagac ccugaguacc cagaugacua cagccaaggu gggaccaggc uggacgggaa   1140
gaaucuggug caggaauggc uggcgaagcg ccagggugcc cgguaugugu ggaaccgcac   1200
ugagcucaug caggcuuccc uggacccguc ugugacccau cucaugggguc ucuuugagcc   1260
uggagacaug aaauacgaga uccaccgaga cuccacacug gaccccuccc ugauggagau   1320
gacagaggcu gcccugcgcc ugcugagcag gaacccccgc ggcuucuucc ucuucgugga   1380
ggguggucgc aucgaccaug gucaucauga aagcagggcu uaccgggcac ugacugagac   1440
gaucauguuc gacgacgcca uugagagggc gggccagcuc accagcgagg aggacacgcu   1500
gagccucguc acugccgacc acucccacgu cuucuccuuc ggaggcuacc cccugcgagg   1560
gagcuccauc uucgggcugg ccccuggcaa ggcccgggac aggaaggccu acacgguccu   1620
ccuauacgga aacgguccag gcuaugugcu caaggacggc gcccggccgg auguuaccga   1680
gagcgagagc gggagccccg aguaucggca gcagucagca gugccccugg acgaagagac   1740
ccacgcaggc gaggacgugg cgguguucgc gcgcggcccg caggcgcacc ugguucacgg   1800
cgugcaggag cagaccuuca uagcgcacgu cauggccuuc gccgccugcc uggagcccua   1860
caccgccugc gaccuggcgc cccccgccgg caccaccgac gccgcgcacc cggguuacuc   1920
uagagucggg gcggccggcc gcuucgagca gacaugaguu uaaacccucu cccuccccc    1980
ccccuaacgu uacuggccga agccgcuugg aauaaggccg gugugcguuu gucuauaugu   2040
uauuuuccac cauauugccg ucuuuuggca augugagggc ccggaaaccu ggcccugucu   2100
ucuugacgag cauuccuagg ggucuuuccc cucucgccaa aggaaugcaa ggucuguuga   2160
augucgugaa ggaagcaguu ccucuggaag cuucuugaag acaaacaacg ucuguagcga   2220
cccuuugcag gcagcggaac cccccaccug gcgacaggug ccucugcggc caaaagccac   2280
guguauaaga uacaccugca aaggcggcac aaccccagug ccacguugug aguuggauag   2340
uuguggaaag agucaaaugg cucuccucaa gcguauucaa caaggggcug aaggaugccc   2400
agaagguacc ccauuguaug ggaucugauc uggggccucg gugcacaugc uuuacaugug   2460
uuuagucgag guuaaaaaaa cgucuaggcc ccccgaacca cggggacgug guuuuccuuu   2520
gaaaaacacg augauaccau gagcacaaau ccuaaaccuc aaagaaaaac caaaagaaac   2580
accaaccguc gcccagaaga cguuaaguuc ccgggcggcg gccagaucgu uggcggagua   2640
uacuuguugc cgcgcagggg ccccagguug ggugugcgca cgacaaggaa aacuucggag   2700
cggucccagc cacgugggag acgccagccc auccccaaag aucggcgcuc cacuggcaag   2760
gccuggggaa aaccaggucg ccccuggccc cuauauggga augagggacu cggcugggca   2820
ggauggcucc uguccccccg aggcucucgc cccuccuggg gccccacuga cccccggcau   2880
aggucgcgca acgugggguaa agucaucgac acccuaacgu guggcuuugc cgaccucaug   2940
ggguacaucc ccgucguagg cgccccgcuu aguggcgccg ccagagcugu cgcgcacggc   3000
gugagagucc uggaggacgg gguuaauuau gcaacaggga accuacccgg uuuccccuuu   3060
ucuaucuucu ugcuggcccu guuguccugc aucaccguuc cggucucugc ugcccaggug   3120
aagaauacca guagcagcua cauggugacc aaugacugcu ccaaugacag caucacuugg   3180
cagcucgagg cugcgguucu ccacgucccc gggugcgucc cgugcgagag aguggggaau   3240
acgucacggu guugggugcc agucucgcca aacauggcug ugcggcagcc cggugcccuc   3300
```

-continued

```
acgcagggguc ugcggacgca caucgauaug guugugaugu ccgccaccuu cugcucugcu   3360
cucuacgugg gggaccucug uggcggggug augcucgcgg cccaggugguu caucgucucg   3420
ccgcaguacc acugguuugu gcaagaaugc aauugcucca ucuacccugg caccaucacu   3480
ggacaccgca uggcauggga caugaugaug aacuggucgc ccacggccac caugauccug   3540
gcguacguga ugcgcguccc cgaggucauc auagacaucg uuagcggggc ucacuggggc   3600
gucauguucg gcuuggccua cuucucuaug cagggagcgu gggcgaaggu cauugucauc   3660
cuucugcugg ccgcuggggu ggacgcgggc accaccaccg uuggaggcgc uguugcacgu   3720
uccaccaacg ugauugccgg cguguucagc cauggcccuc agcagaacau ucagcucauu   3780
aacaccaacg gcaguuggca caucaaccgu acugccuuga auugcaauga cuccuugaac   3840
accggcuuuc ucgcggccuu guucuacacc aaccgcuuua acucgucagg guguccaggg   3900
cgccuguccg ccugccgcaa caucgaggcu uuccggauag gguggggcac ccuacaguac   3960
gaggauaaug ucaccaaucc agaggauaug aggccguacu gcuggcacua ccccccaaag   4020
ccguguggcg uaguccccgc gaggucugug uguggcccag uguacuguuu cacccccagc   4080
ccgguaguag ugggcacgac cgacagacgu ggagugccca ccuacacaug ggagagaau   4140
gagacagaug ucuuccuacu gaacagcacc cgaccgccgc agggcucaug guucggcugc   4200
acguggauga acuccacugg uuucaccaag acuuguggcg cgccaccuug ccgcaccaga   4260
gcugacuuca acgccagcac ggacuuguug ugcccuacgg auuguuuuag gaagcauccu   4320
gaugccacuu auauuaagug ugguucuggg cccuggcuca caccaaagug ccugguccac   4380
uacccuuaca gacucuggca uuaccccugc acagucaauu uuaccaucuu caagauaaga   4440
auguauguag ggggguuga gcacaggcuc acggccgcau gcaacuucac ucgugggau   4500
cgcugcgacu uggaggacag ggacaggagu cagcugucuc cucuguugca cucuaccacg   4560
gaaugggcca uccugcccug caccuacuca gacuuacccg cuuugucaac uggucuucuc   4620
caccuucacc agaacaucgu ggacguacaa uacauguaug gccucucacc ugcuaucaca   4680
aaauacgucg uucgauggga gugggguggua cucuuauucc ugcucuuagc ggacgccaga   4740
gucugcgccu gcuuguggau gcucaucuug uugggccagg ccgaagcagc auuggagaag   4800
uuggucgucu ugcacgcugc gagugcggcu aacugccaug gccucccuaua uuuugccauc   4860
uucuucgugg cagcuuggca caucaggggu cgggugguucc ccuugaccac cuauugccuc   4920
acuggccuau ggcccuucug ccuacugcuc auggcacugc cccggcaggc uuaugccuau   4980
gacgcaccug ugcacggaca gauaggcgug gguuuguuga uauugaucac ccucuucaca   5040
cucaccccgg gguauaagac ccuccucggc cagugucugu ggugguugug cuaucuccug   5100
acccuggggg aagccaugau ucaggagugg guaccaccca ugcaggugcg cggcggccgc   5160
gauggcaucg cgugggccgu cacuauauuc ugcccgggug ugguguuuga cauuaccaaa   5220
uggcuuuugg cguugcuugg gccugcuuac cucuuaaggg ccgcuuugac acaugugccg   5280
uacuucguca gagcucacgc ucugauaagg guaugcgcuu uggugaagca gcucgcgggg   5340
gguagguaug uucaggugggc gcuauuggcc cuuggcaggu ggacuggcac cuacaucuau   5400
gaccaccuca caccuauguc ggacugggcc gcuagcggcc ugcgcgacuu agcggucgcc   5460
guggaaccca ucaucuucag uccgauggag aagaagguca ucgucugggg agcggagacg   5520
gcugcaugug gggacauucu acauggacuu cccgugucccg cccgacucgg ccaggagauc   5580
cuccucggcc cagcugaugg cuacaccucc aaggggugga agcuccuugc ucccaucacu   5640
gcuuaugccc agcaaacacg aggccuccug ggcgccauag uggugaguau gacggggcgu   5700
```

-continued

```
gacaggacag aacaggccgg ggaaguccaa auccugucca cagucucuca guccuuccuc   5760
ggaacaacca ucucgggggu uuuguggacu guuuaccacg gagcuggcaa caagacucua   5820
gccggcuuac ggggucccggu cacgcagaug uacucgagug cugaggggga cuugguaggc   5880
uggcccagcc ccccugggac caagucuuug gagccgugca aguguggagc cgucgaccua   5940
uaucugguca cgcggaacgc ugaugucauc ccggcucgga gacgcgggga caagcgggga   6000
gcauugcucu ccccgagacc cauuucgacc uugaaggggu ccucgggggg gccggugcuc   6060
ugcccuaggg gccacgucgu ugggcucuuc cgagcagcug ugugcucucg gggcguggcc   6120
aaauccaucg auuucauccc cguugagaca cucgacguug uuacaagguc ucccacuuuc   6180
agugacaaca gcacgccacc ggcugugccc cagaccuauc aggucgggua cuugcaugcu   6240
ccaacuggca guggaaagag caccaagguc ccugucgcgu augccgccca gggguacaaa   6300
guacuagugc uuaaccccuc gguagcugcc acccuggggu uuggggcgua ccuauccaag   6360
gcacauggca ucaaucccaa cauuaggacu ggagucagga ccgugaugac cggggaggcc   6420
aucacguacu ccacauaugg caaauuucuc gccgaugggg gcugcgcuag cggcgccuau   6480
gacaucauca uaugcgauga augccacgcu guggaugcua ccuccauucu cggcaucgga   6540
acgguccuug aucaagcaga gacagccggg gucagacuaa cugugcuggc uacggccaca   6600
ccccccgggu cagugacaac cccccauccc gauauagaag agguaggccu cgggcgggag   6660
ggugagaucc ccuucuaugg gagggcgauu ccccuauccu gcaucaaggg agggagacac   6720
cugauuuucu gccacucaaa gaaaaagugu gacgagcucg cggcggcccu ucggggcaug   6780
ggcuugaaug ccguggcaua cuauagaggg uuggacgucu ccauaauacc agcucaggga   6840
gauguggugg ucgucgccac cgacgcccuc augacggggu acacuggaga cuuugacucc   6900
gugaucgacu gcaauguagc ggucacccaa gcugucgacu ucagccugga ccccaccuuc   6960
acuauaacca cacagacugu cccacaagac gcugucucac gcagucagcg ccgcgggcgc   7020
acagguagag gaagacaggg cacuuauagg uauguuucca cuggugaacg agccucagga   7080
auguuugaca guguagugcu uugugagugc uacgacgcag ggcugcgug guacgaucuc   7140
acaccagcgg agaccaccgu caggcuuaga gcguauuuca acacgcccgg ccuacccgug   7200
ugucaagacc aucuugaauu uugggaggca guuuucaccg gccucacaca cauagacgcc   7260
cacuuccucu cccaaacaaa gcaagcgggg gagaacuucg cguaccuagu agccuaccaa   7320
gcuacggugu gcgccagagc caaggccccu cccccguccu gggacgccau guggaagugc   7380
cuggcccgac ucaagccuac gcuugcgggc cccacaccuc uccuguaccg uuugggcccu   7440
auuaccaaug aggucacccu cacacacccu gggacgaagu acaucgccac augcaugcaa   7500
gcugaccuug aggucaugac cagcacgugg guccuagcug gaggaguccu ggcagccguc   7560
gccgcauauu gccuggcgac uggaugcguu uccaucaucg gccgcuugca cgucaaccag   7620
cgagucgucg uugcgccgga uaaggagguc cuguaugagg cuuuugauga gauggaggaa   7680
ugcgccucua gggcggcucu caucgaagag gggcagcgga uagccgagau guugaagucc   7740
aagauccaag gcuugcugca gcaggccucu aagcaggccc aggacauaca acccgcuaug   7800
caggcuucau ggcccaaagu ggaacaauuu ugggccagac acauguggaa cuucauuagc   7860
ggcauccaau accucgcagg auugucaaca cugccaggga accccgcggu ggcuuccaug   7920
auggcauuca gugccgcccu caccaguccg uugucgacca guaccaccau ccuucucaac   7980
aucaugggag gcugguuagc gucccagauc gcaccacccg cgggggccac cggcuuuguc   8040
gucaguggcc uggugggggc ugccgugggc agcauaggcc uggguaaggu gcugguggac   8100
```

-continued

```
auccuggcag gauauggugc gggcauuucg ggggcccucg ucgcauucaa gaucaugucu   8160
ggcgagaagc ccucuaugga agaugucauc aaucuacugc cugggauccu gucuccggga   8220
gcccuggugg ugggggucau cugcgcggcc auucugcgcc gccacguggg accgggggag   8280
ggcgcggucc aauggaugaa caggcuuauu gccuuugcuu ccagaggaaa ccacgucgcc   8340
ccuacucacu acgugacgga gucggaugcg ucgcagcgug ugacccaacu acuuggcucu   8400
cuuacuauaa ccagccuacu cagaagacuc cacaauugga uaacugagga cugccccauc   8460
ccaugcuccg gauccuggcu ccgcgacgug ugggacuggg uuugcaccau cuugacagac   8520
uucaaaaauu ggcugaccuc uaaauuguuc cccaagcugc ccggccuccc cuucaucucu   8580
ugucaaaagg gguacaaggg ugugugggcc ggcacuggca ucaugaccac gcgcugcccu   8640
ugcggcgcca acaucucugg caauguccgc cugggcucua ugaggaucac agggccuaaa   8700
accugcauga acaccuggca ggggaccuuu ccuaucaauu gcuacacgga gggccagugc   8760
gcgccgaaac cccccacgaa cuacaagacc gccaucugga ggguggcggc cucggaguac   8820
gcggaggnga cgcagcaugg gucguacucc uauguaacag gacugaccac ugacaaucug   8880
aaaauuccuu gccaacuacc uucuccagag uuuuucuccu ggguggacgg ugugcagauc   8940
cauagguuug cacccacacc aaagccguuu uuccgggaug aggucucguu cugcguuggg   9000
cuuaauuccu augcugucgg gucccagcuu cccugugaac cugagcccga cgcagacgua   9060
uugaggucca ugcuaacaga uccgccccac aucacggcgg agacugcggc gcggcgcuug   9120
gcacggggau caccuccauc ugaggcgagc uccucaguga gccagcuauc agcaccgucg   9180
cugcgggcca ccugcaccac ccacagcaac accuaugacg uggacauggu cgaugccaac   9240
cugcucaugg agggcggugu ggcucagaca gagccugagu ccagggugcc cguucuggac   9300
uuucucgagc caauggccga ggaagagagc gaccuugagc ccucaauacc aucggagugc   9360
augcucccca ggagcggguu uccacgggcc uuaccggcuu gggcacggcc ugacuacaac   9420
ccgccgcucg uggaaucgug gaggaggcca gauuaccaac cgcccaccgu ugcugguugu   9480
gcucuccccc cccccaagaa ggccccgacg ccucccccaa ggagacgccg gacagugggu   9540
cugagcgaga gcaccauauc agaagcccuc cagcaacugg ccaucaagac cuuuggccag   9600
ccccccucga gcggugaugc aggcucgucc acgggggcgg gcgccgccga auccggcggu   9660
ccgacguccc cuggugagcc ggccccccuca gagacagguu ccgccuccuc uaugcccccc   9720
cucgaggggg agccuggaga uccggaccug gagucugauc agguagagcu ucaaccuccc   9780
ccccaggggg gggggguagc ucccgguucg ggcucggggu cuuggucuac uugcuccgag   9840
gaggacgaua ccaccgugug cugcuccaug ucauacuccu ggaccggggc ucuaauaacu   9900
cccuguagcc ccgaagagga aaaguugcca aucaacccuu ugaguaacuc gcuguugcga   9960
uaccauaaca aggugacug uacaacauca aagagcgccu cacagagggc uaaaaaggua  10020
acuuuugaca ggacgcaagu gcucgacgcc cauuaugacu cagucuuaaa ggacaucaag  10080
cuagcggcuu ccaaggucag cgcaaggcuc cucaccuugg aggaggcgug ccaguugacu  10140
ccaccccauu cugcaagauc caaguaugga uucggggcca aggagguccg cagcuugucc  10200
gggagggccg uuaaccacau caaguccgug uggaaggacc uccuggaaga cccacaaaca  10260
ccaauuccca caaccaucau ggccaaaaau gagguguucu gcguggaccc cgccaagggg  10320
gguaagaaac cagcucgccu caucguuuac ccugaccucg gcguccgggu cugcgagaaa  10380
auggcccucu augacauuac acaaaagcuu ccucaggcgg uaaugggagc uuccuauggc  10440
uuccaguacu ccccugccca acggguggag uaucucuuga aagcaugggc ggaaaagaag  10500
```

gaccccaugg guuuuucgua ugauacccga ugcuucgacu caaccgucac ugagagagac 10560
aucaggaccg aggaguccau auaccaggcc ugcucccugc ccgaggaggc ccgcacugcc 10620
auacacucgc ugacugagag acuuuacgua ggagggccca uguucaacag caagggucaa 10680
accugcgguu acagacguug ccgcgccagc ggggugcuaa ccacuagcau ggguaacacc 10740
aucacaugcu augugaaagc ccuagcggcc ugcaaggcug cggggauagu ugcgccccaca 10800 augcugguau gcggcgauga ccuaguaguc aucucagaaa gccaggggac ugaggaggac 10860
gagcggaacc ugagagccuu cacggaggcc augaccaggu acucugcccc uccuggugau 10920
ccccccagac cggaauauga ccuggagcua auaaacaucu guuccucaaa ugugucugug 10980
gcguugggcc cgcggggccg ccgcagauac uaccugacca gagacccaac cacuccacuc 11040
gcccgggcug ccugggaaac aguuagacac uccccuauca auucauggcu gggaaacauc 11100
auccaguaug cuccaaccau augggguucgc augguccuaa ugacacacuu cuucuccauu 11160
cucauggucc aagacacccu ggaccagaac cucaacuuug agauguaugg aucaguauac 11220
uccgugaauc cuuuggaccu uccagccaua auugagaggu uacacgggcu ugacgccuuu 11280
ucuaugcaca cauacucuca ccacgaacug acgcgggugg cuucagcccu cagaaaacuu 11340
ggggcgccac cccucagggu guggaagagu cgggcucgcg cagucagggc gucccucauc 11400
ucccguggag ggaaagcggc cguuugcggc cgauaucucu ucaauugggc ggugaagacc 11460
aagcucaaac ucacuccauu gccggaggcg cgccuacugg acuuauccag uugguucacc 11520
gucggcgccg gcgggggcga cauuuuucac agcgugucgc gcgcccgacc ccgcucauua 11580
cucuucggcc uacuccuacu uuucguaggg guaggccucu uccuacuccc cgcucgguag 11640
agcggcacac acuagguaca cuccauagcu aacuguuccu uuuuuuuuuu uuuuuuuuuu 11700
uuuuuuuuuu uuuuuuuuuu uucuuuuuuu uuuuuuuccc ucuuucuucc cuucucaucu 11760
uauucuacuu ucuuucuugg uggcuccauc uuagcccuag ucacggcuag cugugaaagg 11820
uccgugagcc gcaugacugc agagagugcc guaacugguc ucucugcaga ucaugu 11876

<210> SEQ ID NO 26
<211> LENGTH: 11876
<212> TYPE: RNA
<213> ORGANISM: Artificial Sequence
<220> FEATURE:
<223> OTHER INFORMATION: replicon RNA derived from the expression vector rFGR-JFH1/SEAP/GND

<400> SEQUENCE: 26 accugcccu aauaggggcg acacuccgcc augaaucacu ccccugugag gaacuacugu 60
cuucacgcag aaagcgccua gccauggcgu uaguaugagu gucguacagc cuccaggccc 120 ccccucccg ggagagccau aguggucugc ggaaccggug aguacaccgg aauugccggg 180
aagacugggu ccuuucuugg auaaacccac ucuaugcccg gccauuuggg cgugcccccg 240
caagacugcu agccgaguag cguuggguug cgaaaggccu ugugguacug ccugauaggg 300
cgcuugcgag ugccccggga ggucucguag accgugcacc augagcacaa auccuaaacc 360
ucaaagaaaa accaaaagaa acaccaaccg acgcguaaug cugcugcugc ugcugcugcu 420
gggccugagg cuacagcucu cccugggcau caucccaguu gaggaggaga acccggacuu 480
cuggaaccgc gaggcagccg aggcccuggg ugccgccaag aagcugcagc cugcacagac 540
agccgccaag aaccucauca ucuuccuggg cgaugggaug ggggugucua cggugacagc 600
ugccaggauc cuaaaagggc agaagaagga caaacugggg ccugagauac cccuggccau 660
ggaccgcuuc ccauaugugg cucuguccaa gacauacaau guagacaaac augugccaga 720

-continued

```
caguggagcc acagccacgg ccuaccugug cggggucaag ggcaacuucc agaccauugg    780
cuugagugca gccgcccgcu uuaaccagug caacacgaca cgcggcaacg aggucaucuc    840
cgugaugaau cgggccaaga aagcagggaa gucaguggga gugguaacca ccacacgagu    900
gcagcacgcc ucgccagccg gcaccuacgc ccacacggug aaccgcaacu gguacucgga    960
cgccgacgug ccugccucgg cccgccagga ggggugccag gacaucgcua cgcagcucau   1020
cuccaacaug gacauugacg ugauccuagg uggaggccga aaguacaugu uucgcauggg   1080
aaccccagac ccugaguacc cagaugacua cagccaaggu gggaccaggc uggacgggaa   1140
gaaucuggug caggaauggc uggcgaagcg ccagggugcc cgguaugugu ggaaccgcac   1200
ugagcucaug caggcuuccc uggacccguc ugugacccau cucaugggguc ucuuugagcc   1260
uggagacaug aaauacgaga uccaccgaga cuccacacug gaccccuccc ugauggagau   1320
gacagaggcu gcccugcgcc ugcugagcag gaacccccgc ggcuucuucc ucuucgugga   1380
gggugggucgc aucgaccaug gucaucauga aagcagggcu uaccgggcac ugacugagac   1440
gaucauguuc gacgacgcca uugagagggc gggccagcuc accagcgagg aggacacgcu   1500
gagccucguc acugccgacc acucccacgu cuucuccuuc ggaggcuacc cccugcgagg   1560
gagcuccauc uucgggcugg ccccuggcaa ggcccgggac aggaaggccu acacgguccu   1620
ccuauacgga aacgguccag gcuaugugcu caaggacggc gcccggccgg auguuaccga   1680
gagcgagagc gggagccccg aguaucggca gcagucagca gugccccugg acgaagagac   1740
ccacgcaggc gaggacgugg cgguguucgc gcgcggcccg caggcgcacc ugguucacgg   1800
cgugcaggag cagaccuuca uagcgcacgu cauggccuuc gccgccugcc uggagcccua   1860
caccgccugc gaccuggcgc cccccgccgg caccaccgac gccgcgcacc cggguuacuc   1920
uagagucggg gcggccggcc gcuucgagca gacaugaguu uaaacccucu cccuccccc    1980
ccccuaacgu uacuggccga agccgcuugg aauaaggccg gugugcguuu gucuauaugu   2040
uauuuuccac cauauugccg ucuuuuggca augugagggc ccggaaaccu ggcccugucu   2100
ucuugacgag cauuccuagg ggucuuuccc cucucgccaa aggaaugcaa ggucuguuga   2160
augucgugaa ggaagcaguu ccucuggaag cuucuugaag acaaacaacg ucuguagcga   2220
cccuuugcag gcagcggaac cccccaccug gcgacaggug ccucugcggc caaaagccac   2280
guguauaaga uacaccugca aaggcggcac aaccccagug ccacguugug aguuggauag   2340
uuguggaaag agucaaaugg cucuccucaa gcguauucaa caaggggcug aaggaugccc   2400
agaagguacc ccauuguaug ggaucugauc uggggccucg gugcacaugc uuuacaugug   2460
uuuagucgag guuaaaaaaa cgucuaggcc ccccgaacca cggggacgug guuuuccuuu   2520
gaaaaacacg augauaccau gagcacaaau ccuaaaccuc aaagaaaaac caaaagaaac   2580
accaaccguc gcccagaaga cguuaaguuc ccgggcggcg gccagaucgu uggcggagua   2640
uacuuguugc cgcgcagggg ccccagguug ggugugcgca cgacaaggaa aacuucggag   2700
cggucccagc cacgugggag acgccagccc auccccaaag aucggcgcuc cacuggcaag   2760
gccuggggaa aaccaggucg ccccuggccc cuauauggga augagggacu cggcugggca   2820
ggauggcucc uguccccccg aggcucucgc cccuccuggg gccccacuga cccccggcau   2880
aggucgcgca acgugggguaa agucaucgac acccuaacgu guggcuuugc cgaccucaug   2940
ggguacaucc ccgucguagg cgccccgcuu aguggcgccg ccagagcugu cgcgcacggc   3000
gugagagucc uggaggacgg gguuaauuau gcaacaggga accuacccgg uuuccccuuu   3060
ucuaucuucu ugcuggcccu guuguccugc aucaccguuc cggucucugc ugcccaggug   3120
```

aagaauacca guagcagcua cauggugacc aaugacugcu ccaaugacag caucacuugg 3180
cagcucgagg cugcgguucu ccacgucccc gggugcgucc cgugcgagag aguggggaau 3240
acgucacggu guugggugcc agucucgcca aacauggcug ugcggcagcc cggugcccuc 3300
acgcaggguc ugcggacgca caucgauaug guugugaugu ccgccaccuu cugcucugcu 3360
cucuacgugg gggaccucug uggcggggug augcucgcgg cccagguguu caucgucucg 3420
ccgcaguacc acugguuugu gcaagaaugc aauugcucca ucuacccugg caccaucacu 3480
ggacaccgca uggcauggga caugaugaug aacuggucgc ccacggccac caugauccug 3540
gcguacguga ugcgcguccc cgaggucauc auagacaucg uuagcggggc ucacuggggc 3600
gucauguucg gcuuggccua cuucucuaug cagggagcgu gggcgaaggu cauugucauc 3660
cuucugcugg ccgcuggggu ggacgcgggc accaccaccg uuggaggcgc uguugcacgu 3720
uccaccaacg ugauugccgg cguguucagc cauggcccuc agcagaacau ucagcucauu 3780
aacaccaacg gcaguuggca caucaaccgu acugccuuga auugcaauga cuccuugaac 3840
accggcuuuc ucgcggccuu guucuacacc aaccgcuuua acucgucagg guguccaggg 3900
cgccuguccg ccugccgcaa caucgaggcu uuccggauag gguggggcac ccuacaguac 3960
gaggauaaug ucaccaaucc agaggauaug aggccguacu gcuggcacua ccccccaaag 4020
ccguguggcg uagucccccgc gaggucugug uguggcccag uguacuguuu cacccccagc 4080
ccgguaguag ugggcacgac cgacagacgu ggagugccca ccuacacaug gggagagaau 4140
gagacagaug ucuuccuacu gaacagcacc cgaccgccgc agggcucaug guucggcugc 4200
acguggauga acuccacugg uuucaccaag acuuguggcg cgccaccuug ccgcaccaga 4260
gcugacuuca acgccagcac ggacuuguug ugcccuacgg auuguuuuag gaagcauccu 4320
gaugccacuu auauuaagug ugguucuggg cccuggcuca caccaaagug ccugguccac 4380
uacccuuaca gacucuggca uuaccccugc acagucaauu uuaccaucuu caagauaaga 4440
auguauguag ggggguuga gcacaggcuc acggccgcau gcaacuucac ucguggggau 4500
cgcugcgacu uggaggacag ggacaggagu cagcugucuc cucuguugca cucuaccacg 4560
gaaugggcca uccugcccug caccuacuca gacuuacccg cuuugucaac uggucuucuc 4620
caccuucacc agaacaucgu ggacguacaa uacauguaug gccucucacc ugcuaucaca 4680
aaauacgucg uucgauggga gugggugua cucuuauucc ugcucuuagc ggacgccaga 4740
gucugcgccu gcuuguggau gcucaucuug uugggccagg ccgaagcagc auuggagaag 4800
uuggucgucu ugcacgcugc gagugcggcu aacugccaug gccuccuaua uuuugccauc 4860
uucuucgugg cagcuuggca caucaggggu cgggugguccc ccuugaccac cuauugccuc 4920
acuggccuau ggcccuucug ccuacugcuc auggcacugc cccggcaggc uuaugccuau 4980
gacgcaccug ugcacggaca gauaggcgug gguuuguuga uauugaucac ccucuucaca 5040
cucaccccgg gguauaagac ccuccucggc caguqucugu ggugguugug cuaucuccug 5100
acccuggggg aagccaugau ucaggagugg guaccaccca ugcaggugcg cggcggccgc 5160
gauggcaucg cgugggccgu cacuauauuc ugcccgggug ugguguuuga cauuaccaaa 5220
uggcuuuugg cguugcuugg gccugcuuac cucuuaaggg ccgcuuugac acaugugccg 5280
uacuucguca gagcucacgc ucugauaagg guaugcgcuu uggugaagca gcucgcgggg 5340
gguagguaug uucagguggc gcuauuggcc cuuggcaggu ggacuggcac cuacaucuau 5400
gaccaccuca caccuauguc ggacugggcc gcuagcggcc ugcgcgacuu agcggucgcc 5460
guggaaccca ucaucuucag uccgauggag aagaagguca ucgucugggg agcggagacg 5520
gcugcaugug gggacauucu acauggacuu cccguguccg cccgacucgg ccaggagauc 5580
cuccucggcc cagcugaugg cuacaccucc aaggggugga agcuccuugc ucccaucacu 5640
gcuuaugccc agcaaacacg aggccuccug ggcgccauag uggugaguau gacggggcgu 5700
gacaggacag aacaggccgg ggaaguccaa auccugucca cagucucuca guccuuccuc 5760
ggaacaacca ucucgggggu uuuguggacu guuuaccacg gagcuggcaa caagacucua 5820
gccggcuuac gggguccggu cacgcagaug uacucgagug cugagggggga cuugguaggc 5880
uggcccagcc ccccugggac caagucuuug gagccgugca aguguggagc cgucgaccua 5940
uaucugguca cgcggaacgc ugaugucauc ccggcucgga gacgcgggga caagcgggga 6000
gcauugcucu ccccgagacc cauuucgacc uugaaggggu ccucgggggg gccggugcuc 6060
ugcccuaggg gccacgucgu ugggcucuuc cgagcagcug ugugcucucg gggcguggcc 6120
aaauccaucg auuucauccc cguugagaca cucgacguug uuacaagguc ucccacuuuc 6180
agugacaaca gcacgccacc ggcugugccc cagaccuauc aggucgggua cuugcaugcu 6240
ccaacuggca guggaaagag caccaagguc ccugucgcgu augccgccca gggguacaaa 6300
guacuagugc uuaaccccuc gguagcugcc acccuggggu uuggggcgua ccuauccaag 6360
gcacauggca ucaaucccaa cauuaggacu ggagucagga ccgugaugac cggggaggcc 6420
aucacguacu ccacauaugg caaauuucuc gccgaugggg gcugcgcuag cggcgccuau 6480
gacaucauca uaugcgauga augccacgcu guggaugcua ccuccauucu cggcaucgga 6540
acgguccuug aucaagcaga gacagccggg gucagacuaa cugugcuggc uacggccaca 6600
ccccccgggu cagugacaac cccccauccc gauauagaag agguaggccu cgggcgggag 6660
ggugagaucc ccuucuaugg gagggcgauu ccccuauccu gcaucaaggg agggagacac 6720
cugauuuucu gccacucaaa gaaaaagugu gacgagcucg cggcggcccu ucggggcaug 6780
ggcuugaaug ccguggcaua cuauagaggg uuggacgucu ccauaauacc agcucaggga 6840
gauguggugg ucgucgccac cgacgcccuc augacggggu acacuggaga cuuugacucc 6900
gugaucgacu gcaauguagc ggucacccaa gcugucgacu ucagccugga ccccaccuuc 6960
acuauaacca cacagacugu cccacaagac gcugucucac gcagucagcg ccgcgggcgc 7020
acagguagag gaagacaggg cacuuauagg uauguuucca cuggugaacg agccucagga 7080
auguuugaca guguagugcu uugugagugc uacgacgcag ggcugcgug guacgaucuc 7140
acaccagcgg agaccaccgu caggcuuaga gcguauuuca acacgcccgg ccuacccgug 7200
ugucaagacc aucuugaauu uugggaggca guuuucaccg gccucacaca cauagacgcc 7260
cacuuccucu cccaaacaaa gcaagcgggg gagaacuucg cguaccuagu agccuaccaa 7320
gcuacggugu gcgccagagc caaggccccu cccccguccu gggacgccau guggaagugc 7380
cuggcccgac ucaagccuac gcuugcgggc cccacaccuc uccuguaccg uuugggcccu 7440
auuaccaaug aggucacccu cacacacccu gggacgaagu acaucgccac augcaugcaa 7500
gcugaccuug aggucaugac cagcacgugg guccuagcug gaggaguccu ggcagccguc 7560
gccgcauauu gccuggcgac uggaugcguu uccaucaucg gccgcuugca cgucaaccag 7620
cgagucgucg uugcgccgga uaaggagguc cuguaugagg cuuuugauga gauggaggaa 7680
ugcgccucua gggcggcucu caucgaagag gggcagcgga uagccgagau guugaagucc 7740
aagauccaag gcuugcugca gcaggccucu aagcaggccc aggacauaca acccgcuaug 7800
caggcuucau ggcccaaagu ggaacaauuu ugggccagac acauguggaa cuucauuagc 7860
ggcauccaau accucgcagg auugucaaca cugccaggga accccgcggu ggcuuccaug 7920

```
auggcauuca gugccgcccu caccaguccg uugucgacca guaccaccau ccuucucaac   7980
aucaugggag gcugguuagc gucccagauc gcaccacccg cgggggccac cggcuuuguc   8040
gucaguggcc uggugggggc ugccgugggc agcauaggcc uggguaaggu gcugguggac   8100
auccuggcag gauauggugc gggcauuucg ggggcccucg ucgcauucaa gaucaugucu   8160
ggcgagaagc ccucuaugga agaugucauc aaucuacugc cugggauccu gucuccggga   8220
gcccuggugg ugggggucau cugcgcggcc auucugcgcc gccacguggg accgggggag   8280
ggcgcggucc aauggaugaa caggcuuauu gccuuugcuu ccagaggaaa ccacgucgcc   8340
ccuacucacu acgugacgga gucggaugcg ucgcagcgug ugacccaacu acuuggcucu   8400
cuuacuauaa ccagccuacu cagaagacuc cacaauugga uaacugagga cugccccauc   8460
ccaugcuccg gauccuggcu ccgcgacgug ugggacuggg uuugcaccau cuugacagac   8520
uucaaaaauu ggcugaccuc uaaauuguuc cccaagcugc ccggccuccc cuucaucucu   8580
ugucaaaagg gguacaaggg ugugugggcc ggcacuggca ucaugaccac gcgcugcccu   8640
ugcggcgcca acaucucugg caauguccgc cugggcucua ugaggaucac agggccuaaa   8700
accugcauga acaccuggca ggggaccuuu ccuaucaauu gcuacacgga gggccagugc   8760
gcgccgaaac cccccacgaa cuacaagacc gccaucugga ggguggcggc cucggaguac   8820
gcggagguga cgcagcaugg gucguacucc uauguaacag gacugaccac ugacaaucug   8880
aaaauuccuu gccaacuacc uucuccagag uuuuucuccu ggguggacgg ugugcagauc   8940
cauagguuug cacccacacc aaagccguuu uuccgggaug aggucucguu cugcguuggg   9000
cuuaauuccu augcugucgg gucccagcuu cccugugaac cugagcccga cgcagacgua   9060
uugaggucca ugcuaacaga uccgccccac aucacggcgg agacugcggc gcggcgcuug   9120
gcacggggau caccuccauc ugaggcgagc uccucaguga gccagcuauc agcaccgucg   9180
cugcgggcca ccugcaccac ccacagcaac accuaugacg uggacauggu cgaugccaac   9240
cugcucaugg agggcggugu ggcucagaca gagccugagu ccagggugcc cguucuggac   9300
uuucucgagc caauggccga ggaagagagc gaccuugagc ccucaauacc aucggagugc   9360
augcucccca ggagcggguu uccacgggcc uuaccggcuu gggcacggcc ugacuacaac   9420
ccgccgcucg uggaaucgug gaggaggcca gauuaccaac cgcccaccgu ugcugguugu   9480
gcucuccccc cccccaagaa ggccccgacg ccucccccaa ggagacgccg gacagugggu   9540
cugagcgaga gcaccauauc agaagcccuc cagcaacugg ccaucaagac cuuuggccag   9600
ccccccucga gcggugaugc aggcucgucc acgggggcgg gcgccgccga auccggcggu   9660
ccgacguccc cuggugagcc ggccccccuca gagacagguu ccgccuccuc uaugcccccc   9720
cucgaggggg agccuggaga uccggaccug gagucugauc agguagagcu ucaaccuccc   9780
ccccaggggg gggggguagc ucccgguucg ggcucggggu cuuggucuac uugcuccgag   9840
gaggacgaua ccaccgugug cugcuccaug ucauacuccu ggaccggggc ucuaauaacu   9900
cccuguagcc ccgaagagga aaaguugcca aucaacccuu ugaguaacuc gcuguugcga   9960
uaccauaaca agguguacug uacaacauca aagagcgccu cacagagggc uaaaaaggua  10020
acuuuugaca ggacgcaagu gcucgacgcc cauuaugacu cagucuuaaa ggacaucaag  10080
cuagcggcuu ccaaggucag cgcaaggcuc cucaccuugg aggaggcgug ccaguugacu  10140
ccaccccauu cugcaagauc caaguaugga uucggggcca aggagguccg cagcuugucc  10200
gggagggccg uuaaccacau caaguccgug uggaaggacc uccuggaaga cccacaaaca  10260
ccaauuccca caaccaucau ggccaaaaau gagguguucu gcguggaccc cgccaagggg  10320
```

-continued

```
gguaagaaac cagcucgccu caucguuuac ccugaccucg gcguccgggu cugcgagaaa  10380
auggcccucu augacauuac acaaaagcuu ccucaggcgg uaaugggagc uuccuauggc  10440
uuccaguacu ccccugccca acgggugggag uaucucuuga aagcaugggc ggaaaagaag  10500
gaccccaugg guuuuucgua ugauacccga ugcuucgacu caaccgucac ugagagagac  10560
aucaggaccg aggaguccau auaccaggcc ugcucccugc ccgaggaggc ccgcacugcc  10620
auacacucgc ugacugagag acuuuacgua ggagggccca uguucaacag caagggucaa  10680
accugcgguu acagacguug ccgcgccagc ggggugcuaa ccacuagcau ggguaacacc  10740
aucacaugcu augugaaagc ccuagcggcc ugcaaggcug cggggauagu ugcgcccaca  10800
augcugguau gcggcaauga ccuaguaguc aucucagaaa gccaggggac ugaggaggac  10860
gagcggaacc ugagagccuu cacggaggcc augaccaggu acucugcccc uccuggugau  10920
ccccccagac cggaauauga ccuggagcua auaacauccu guuccucaaa ugugucugug  10980
gcguugggcc cgcggggccg ccgcagauac uaccugacca gagacccaac cacuccacuc  11040
gcccgggcug ccugggaaac aguuagacac uccccuauca auucauggcu gggaaacauc  11100
auccaguaug cuccaaccau augguucgc augguccuaa ugacacacuu cuucuccauu  11160
cucauggucc aagacacccu ggaccagaac cucaacuuug agauguaugg aucaguauac  11220
uccgugaauc cuuuggaccu uccagccaua auugagaggu uacacgggcu ugacgccuuu  11280
ucuaugcaca cauacucuca ccacgaacug acgcgggugg cuucagcccu cagaaaacuu  11340
ggggcgccac cccucagggu guggaagagu cgggcucgcg cagucagggc gucccucauc  11400
ucccguggag ggaaagcggc cguuugcggc cgauaucucu ucaauugggc ggugaagacc  11460
aagcucaaac ucacuccauu gccggaggcg cgccuacugg acuuauccag uugguucacc  11520
gucggcgccg gcgggggcga cauuuuucac agcgugucgc gcgcccgacc ccgcucauua  11580
cucuucggcc uacuccuacu uuucguaggg guaggccucu uccuacuccc cgcucgguag  11640
agcggcacac acuagguaca cuccauagcu aacuguuccu uuuuuuuuuu uuuuuuuuuu  11700
uuuuuuuuuu uuuuuuuuuu uucuuuuuuu uuuuuuuccc ucuuucuucc cuucucaucu  11760
uauucuacuu ucuuucuugg uggcuccauc uuagcccuag ucacggcuag cugugaaagg  11820
uccgugagcc gcaugacugc agagagugcc guaacugguc ucucugcaga ucaugu      11876
```

NUCLEIC ACID CONSTRUCT CONTAINING FULL LENGTH GENOME OF HUMAN HEPATITIS C VIRUS, RECOMBINANT FULL LENGTH VIRUS GENOME-REPLICATING CELLS HAVING THE NUCLEIC ACID CONSTRUCT TRANSFERRED THEREINTO AND METHOD OF PRODUCING HEPATITIS C VIRUS PARTICLE

CROSS REFERENCES TO RELATED APPLICATIONS

This application is a Divisional of application Ser. No. 10/589,902, filed on Aug. 17, 2006, which issued as U.S. Pat. No. 7,659,103, which is a national phase under 35 U.S.C. §371 of PCT International Application No. PCT/JP2005/003232 which has an international filing date of Feb. 21, 2005, which designated the United States and on which priority is claimed under 35 U.S.C. §120, the entire contents of which are hereby incorporated by reference. This Divisional application claims priority under 35 U.S.C. §119 on Application 2004-045489 filed in Japan on Feb. 20, 2004, the entire contents of which are hereby incorporated by reference.

TECHNICAL FIELD

The present invention relates to nucleic acid constructs containing full length genome of hepatitis C virus, an in vitro method for producing hepatitis C virus particles and use of the produced hepatitis C virus particles.

BACKGROUND ART

Hepatitis C virus (HCV) belongs to the family Flaviviridae and is a virus having a single stranded (+) sense RNA genome and is known to cause hepatitis C.

HCV causes chronic hepatitis by persistent infection. Currently, the main cause of chronic hepatitis observed worldwide is persistent HCV infection. Actually, around 50% of individuals with persistent infection develop chronic hepatitis. Chronic hepatitis in approximately 20% of these patients shifts to liver cirrhosis over the course of 10 to 20 years, and some of these patients further go on to advanced lethal pathological conditions such as hepatic cancer.

Hepatitis C is currently treated mainly by a therapy using interferon-α or interferon-β, or a therapy using a combination of interferon-α and ribavirin, a purine-nucleoside derivative. However, even when these therapies are performed, the therapeutic effects are observed in only approximately 60% of all treated patients. When therapies are ceased after effects are seen, the disease recrudesces in more than half of the patients.

It is an important goal to develop therapeutic agents or prophylactic agents effective against hepatitis C. The incidence rate of hepatitis C, which in the end brings about serious consequences, is high in industrial countries, and there is currently no causal treatment available. Hence, the development of HCV-specific chemotherapies and vaccine therapies are desired. A target for the development of an anti-HCV agent may be the suppression of HCV replication or the suppression of infection of cells with HCV.

Recently, HCV subgenomic RNA replicon systems have been prepared as HCV-derived autonomously replicable RNA (see, Patent Documents 1, 2 and 3, Non-Patent Documents 1-4). In the HCV subgenomic RNA replicon systems, HCV replicon RNA in which the structural genes of the HCV genome is eliminated and replaced with a drug-selectable marker gene, are prepared and introduced into cultured cells, and thereby the replicon RNA is replicated autonomously in the cells. By using these systems it becomes possible to analyze the replication mechanism of HCV. However, this is an experimental system in which only viral RNA replication is evaluated in the process of the proliferation and replication of HCV virus, and the process of the formation of HCV virus particles in the infected cells and the extracellular release or infection to another cell cannot be analyzed.

At this time, the process of HCV virus particle formation and extracellular release as well as infection to another cell can only be evaluated in the experimental systems using animals such as chimpanzees (Non-Patent Document 5). However, the experimental systems using living organisms such as animals are complicated and very difficult to analyze. Therefore, in order to analyze the process of HCV virus particle formation and extracellular release as well as infection to another cell, and to produce an anti-HCV agent which will have the action mechanism of inhibiting this process, it is necessary to establish a highly simplified experimental system reproducing this process, i.e. a HCV virus particle production system in cell culture experimental systems.

Further, once HCV virus particles can be provided stably using the cell culture system, it is possible to attenuate the virus or to produce noninfectious HCV virus using molecular biological techniques, and this can be used in vaccines.

Patent Document 1: JP Patent Publication (Kokai) No. 2001-17187
Patent Document 2: International Patent Application PCT/JP03/15038
Patent Document 3: JP Patent Application No. 2003-329082
Non-Patent Document 1: Lohmann et al., Science, (1999) 285, p. 110-113
Non-Patent Document 2: Blight et al., Science, (2000) 290, p. 1972-1974
Non-Patent Document 3: Friebe et al., J. Virol., (2001) 75(24): p. 12047-12057
Non-Patent Document 4: Ikeda et al., J. Virol., (2002) 76(6): p. 2997-3006
Non-Patent Document 5: Kolykhalov et al., Science, (1997) 277, p. 570-574
Non-Patent Document 6: Kato et al., Gastroenterology, (2003) 125, p. 1808-1817
Non-Patent Document 7: Yanagi et al., Proc. Natl. Acad. Sci., (1997) 96(16): p. 8738-8743
Non-Patent Document 8: Okamoto et al., J. Gen. Virol., (1991) 73, p 2697-26704
Non-Patent Document 9: Aoyagi et al., J. Clin. Microbiol., (1999) 37(6): p. 1802-1808

DISCLOSURE OF THE INVENTION

The objective of the present invention is to provide a method for efficiently replicating RNA containing full length HCV genomic sequences and a method for producing HCV virus particles containing full length HCV replicon RNA or full length HCV genomic RNA in a cell culture system. The objective of the present invention has never been achieved so far.

As a result of intensive studies to achieve the above object, the present inventors have developed a method for producing HCV virus particles in a cell culture system. That is, the present invention is as follows.

[1] A replicon RNA, comprising a nucleotide sequence comprising a 5' untranslated region, a core protein coding sequence, an E1 protein coding sequence, an E2 protein coding sequence, an NS2 protein coding sequence, an NS3 protein coding sequence, an NS4A protein coding sequence, an NS4B protein coding sequence, an NS5A protein coding sequence, an NS5B protein coding sequence, and a 3' untranslated region of genomic RNA of hepatitis C virus of genotype 2a, at least one selectable marker gene and/or at least one reporter gene, and at least one IRES sequence.

In this replicon RNA, preferably the nucleotide sequence comprises the 5' untranslated region, the at least one selectable marker gene and/or the at least one reporter gene, and the at least one IRES sequence, and the core protein coding sequence, the E1 protein coding sequence, the E2 protein coding sequence, the NS2 protein coding sequence, the NS3 protein coding sequence, the NS4A protein coding sequence, the NS4B protein coding sequence, the NS5A protein coding sequence, the NS5B protein coding sequence, and the 3' untranslated region, in this order in the 5' to 3' direction.

In the more preferable embodiment of this replicon RNA, the genomic RNA of hepatitis C virus of genotype 2a is an RNA comprising a nucleotide sequence shown in SEQ ID NO: 12.

In the still more preferable embodiment of this replicon RNA, the 5' untranslated region comprises a nucleotide sequence shown in SEQ ID NO: 1, the core protein coding sequence comprises a nucleotide sequence shown in SEQ ID NO: 2, the E1 protein coding sequence comprises a nucleotide sequence shown in SEQ ID NO: 3, the E2 protein coding sequence comprises a nucleotide sequence shown in SEQ ID NO: 4, the NS2 protein coding sequence comprises a nucleotide sequence shown in SEQ ID NO: 5, the NS3 protein coding sequence comprises a nucleotide sequence shown in SEQ ID NO: 6, the NS4A protein coding sequence comprises a nucleotide sequence shown in SEQ ID NO: 7, the NS4B protein coding sequence comprises a nucleotide sequence shown in SEQ ID NO: 8, the NS5A protein coding sequence comprises a nucleotide sequence shown in SEQ ID NO: 9, the NS5B protein coding sequence comprises a nucleotide sequence shown in SEQ ID NO: 10, and the 3' untranslated region comprises a nucleotide sequence shown in SEQ ID NO: 11.

[2] A replicon RNA, comprising the following RNA (a) or (b):

(a) an RNA comprising a nucleotide sequence shown in SEQ ID NO: 13; or (b) an RNA comprising a nucleotide sequence derived from the nucleotide sequence shown in SEQ ID NO: 13 by deletion, substitution or addition of 1 to 100 nucleotides, and having autonomous replication ability and virus particle production ability.

[3] A method for producing a cell which replicates a replicon RNA and produces a virus particle, comprising introducing the replicon RNA of any one of [1] or [2] described above into a cell.

For this method the cell is preferably a proliferative cell. For this method the cell is also or otherwise preferably a eukaryotic cell.

For this method, the eukaryotic cell is preferably a human liver-derived cell, a human uterine cervix-derived cell or a human fetal kidney-derived cell. More preferably, the eukaryotic cell is a Huh7 cell, a HepG2 cell, an IMY-N9 cell, a HeLa cell or a 293 cell.

[4] A cell obtainable by the method of [3] described above, which replicates the replicon RNA and produces the virus particle.

[5] A method for producing a hepatitis C virus particle, comprising culturing the cell of [4] described above to allow the cell to produce the virus particle.

[6] A hepatitis C virus particle obtainable by the method of [5] described above.

[7] A method for producing a hepatitis C virus infected cell, comprising culturing the cell of [4] described above and infecting other cells with the virus particle in the culture.

[8] A hepatitis C virus infected cell obtainable by the method of [7] described above.

[9] A method for screening an anti-hepatitis C virus substance, comprising culturing, in the presence of a test substance, at lease one selected from the group consisting of following (a), (b) and (c):

(a) the cell of [4] described above, (b) the hepatitis C virus infected cell of [8] described above, and (c) the hepatitis C virus particle of [6] described above and a hepatitis C virus permissive cell;

and detecting the replicon RNA or the virus particles in the resulting culture.

[10] A hepatitis C vaccine, comprising the hepatitis C virus particle of [6] described above or a part thereof.

[11] A method for producing a hepatitis C vaccine by using the hepatitis C virus particle of [6] described above or part thereof as an antigen.

[12] A method for producing a hepatotropic virus vector for gene therapy by using the replicon RNA of [1] or [2] described above.

[13] A hepatotropic virus vector obtainable by the method of [12] described above.

[14] A method for replicating and/or expressing a foreign gene in a cell, comprising inserting an RNA encoding the foreign gene to the replicon RNA of any one of [1] or [2] described above and introducing it into said cell.

[15] A method for producing a cell which replicates an RNA and produces a virus particle, comprising introducing into the cell the RNA comprising a nucleotide sequence shown in SEQ ID NO. 12.

[16] A method for producing a hepatitis C virus particle, comprising introducing into a cell the RNA comprising a nucleotide sequence shown in SEQ ID NO: 12 and culturing the cell to allow the cell to produce a virus particle.

[17] A method of [15] or [16] described above, wherein the cell is a proliferative cell.

[18] A method for producing a virus vector comprising a foreign gene, comprising inserting an RNA encoding a foreign gene into an RNA comprising the nucleotide sequence shown in SEQ ID NO: 12, introducing it into a cell, and culturing the cell to allow the cell to produce a virus particle.

[19] An antibody against the hepatitis C virus particle of [6] described above

The contents in the description and the drawings of Japanese Patent Application No. 2004-045489, from which the present application claims priority, are incorporated herein.

BRIEF DESCRIPTION OF THE DRAWINGS

The patent or patent application file contains at least one drawing executed in color. Copies of this patent or patent application publication with color drawing(s) will be provided by the Office upon request and payment of the necessary fee.

BEST MODE FOR CARRYING OUT THE INVENTION

Figure 1:
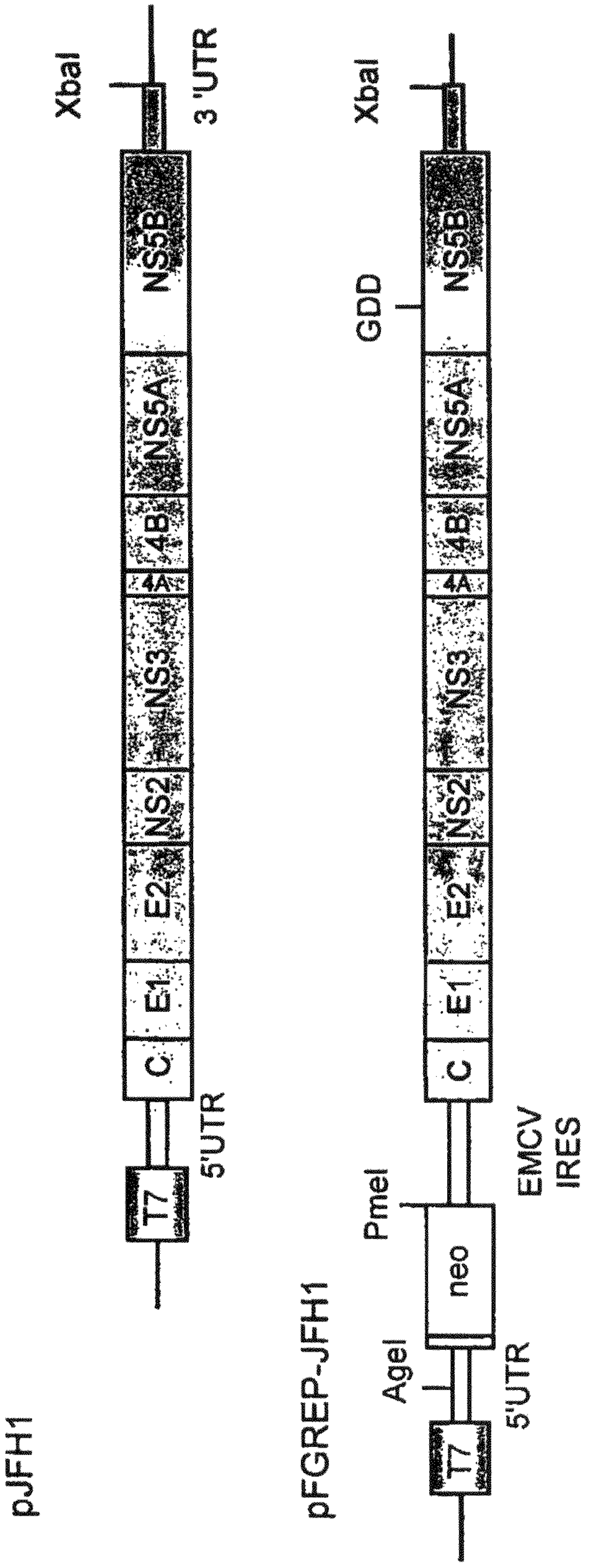
FIG. 1 is a schematic view showing procedures for constructing a template DNA for preparing the full length HCV replicon RNA or the full length HCV genomic RNA of the present invention. The upper part of FIG. 1 shows the structure of a plasmid clone pJFH1, which is produced by inserting the full length HCV genome downstream of the T7 promoter. The lower part of FIG. 1 shows the structure of plasmid clone pFGREP-JFH1 comprising the full length HCV genomic sequence, in which a DNA fragment containing the neomycin resistance gene and EMCV IRES is inserted downstream of the T7 promoter of pJFH1 and the 5' untranslated region. The terms shown in the Figure are as follows. T7: T7 RNA promoter, 5' UTR: 5' untranslated region, C: core protein, E1, E2: envelope proteins. NS2, NS3, NS4A, NS4B, 4A, 4B: non-structural proteins. 3' UTR: 3' untranslated region. AgeI, PmeI, XbaI: restriction sites of the restriction enzymes AgeI, PmeI and XbaI. GDD: the site of the amino acids motif GDD which corresponds to the active center of NS5B protein. neo: the neomycin resistant gene. EMCV IRES: encephalomyocarditis virus internal ribosomal entry site.

The present invention is explained in detail as follows.

1. Full Length HCV Replicon RNA

The genome of hepatitis C virus (HCV) is a single-stranded (+) strand RNA comprising approximately 9600 nucleotides. This genomic RNA comprises the 5' untranslated region (also denoted as 5' NTR or 5' UTR), a translated region composed of a structural region and a non-structural region, and the 3' untranslated region (also denoted as 3' NTR or 3' UTR). HCV structural proteins are encoded in the structural region, and a plurality of non-structural proteins are encoded in the non-structural region.

Such HCV structural proteins (core, E1 and E2) and non-structural proteins (NS2, NS3, NS4A, NS4B, NS5A and NS5B) are generated by first translating the translated region into a single continuous polyprotein and then releasing by having restricted cleavage of the polyprotein by proteases. Among these structural proteins and non-structural proteins (that is, viral proteins of HCV), core is a core protein, E1 and E2 are envelope proteins. The non-structural proteins are proteins involved in viral own replication, and NS2 is known to have metalloprotease activity, and NS3 is known to have serine protease activity (at one-third of the N terminal side) and helicase activity (at two-thirds of the C-terminal side). Furthermore, NS4A is a cofactor for protease activity of NS3, and NS5B has been reported to have RNA-dependent RNA polymerase activity.

The present inventors constructed a replicon RNA having autonomous replication ability and virus particles production ability, using HCV genomic RNA.

RNA having autonomous replication ability which has been produced by modifying the HCV genomic RNA is called “replicon RNA” or “RNA replicon” herein. In the present specification, the replicon RNA derived from HCV may also be called HCV-RNA replicon. The replicon RNA of the present invention comprising the full length of HCV genomic RNA is called “full length HCV replicon RNA” herein. The full length HCV replicon RNA of the present invention has an ability of producing virus particles.

In the preferred embodiment of the full length HCV replicon RNA in the present invention, hepatitis C virus is, but not limited to, preferably hepatitis C virus of genotype 2a. In the present invention, “hepatitis C virus of genotype 2a” or “HCV of genotype 2a” means a hepatitis virus identified as the genotype 2a according to the international classification by Simmonds et al. (see Simmonds, P. et al, Hepatology, (1994) 10, p. 1321-1324). In the present invention, “hepatitis C virus of genotype 2a” or “HCV of genotype 2a” includes not only virus having naturally-occurring HCV genomic RNA but also virus having a genomic RNA in which the naturally-occurring HCV genomic sequence is modified artificially. A particular example of the HCV of genotype 2a includes JFH-1 strain (see JP Patent Publication (Kokai) No. 2002-171978)

In the present specification, “the genomic RNA of hepatitis C virus” means RNA comprising the nucleotide sequence over the entire region of the single-stranded (+) sense RNA genome of hepatitis C virus. The genomic RNA of hepatitis C virus of genotype 2a is, but not limited to, preferably RNA comprising the nucleotide sequence shown in SEQ ID NO: 12.

One of the embodiments of the full length HCV replicon RNA according to the present invention is a replicon RNA comprising the nucleotide sequence comprising a 5' untranslated region, a core protein coding sequence, an E1 protein coding sequence, an E2 protein coding sequence, an NS2 protein coding sequence, an NS3 protein coding sequence, an NS4A protein coding sequence, an NS4B protein coding sequence, an NS5A protein coding sequence, an NS5B protein coding sequence, and a 3' untranslated region, at least one selectable marker gene or reporter gene, and at least one IRES sequence.

It is not limited but preferable that the full length HCV replicon RNA according to the present invention comprises: the 5' untranslated region, at least one selectable marker gene or reporter gene, at least one IRES sequence, the core protein coding sequence, the E1 protein coding sequence, the E2 protein coding sequence, the NS2 protein coding sequence, the NS3 protein coding sequence, the NS4A protein coding sequence, the NS4B protein coding sequence, the NS5A protein coding sequence, the NS5B protein coding sequence, and the 3' untranslated region, in this order in the 5' to 3' direction.

In the specification of the present application, “5' untranslated region” (5' NTR or 5' UTR), “core protein coding sequence” (core region or C region), “E1 protein coding sequence” (E1 region), “E2 protein coding sequence” (E2 region), “NS2 protein coding sequence” (NS2 region), “NS3 protein coding sequence” (NS3 region), “NS4A protein coding sequence” (NS4A region), “NS4B protein coding sequence” (NS4B region), “NS5A protein coding sequence” (NS5A region), “NS5B protein coding sequence” (NS5B region) and “3'untranslated region” (3' NTR or 3' UTR), and other specific regions or sites are defined based on the full length genomic RNA (SEQ ID NO: 12) comprising the entire region of the genome of the JFH-1 strain (JP Patent Publication (Kokai) No. 2002-171978), which is a HCV virus of genotype 2a.

Also, a partial region or site in the genome of hepatitis C virus (HCV) according to the present invention may be defined based on the sequences shown in SEQ ID NOs: 1-11 that are the partial nucleotide sequences of the genomic RNA of JFH-1 strain (SEQ ID NO: 12). “5' untranslated region” of the full length genomic RNA of JFH-1 strain (derived from JFH-1 clone; SEQ ID NO: 12) comprises the nucleotide sequence shown in SEQ ID NO: 1. “Core protein coding sequence” comprises the nucleotide sequence shown in SEQ ID NO: 2. “E1 protein coding sequence” comprises the nucleotide sequence shown in SEQ ID NO: 3. “E2 protein coding sequence” comprises the nucleotide sequence shown in SEQ ID NO: 4. “NS2 protein coding sequence” comprises the nucleotide sequence shown in SEQ ID NO: 5. “NS3 protein coding sequence” comprises the nucleotide sequence shown in SEQ ID NO: 6. “NS4A protein coding sequence” comprises the nucleotide sequence shown in SEQ ID NO: 7. “NS4B protein coding sequence” comprises the nucleotide sequence shown in SEQ ID NO: 8. “NS5A protein coding sequence” comprises the nucleotide sequence shown in SEQ ID NO: 9. “NS5B protein coding sequence” comprises the nucleotide sequence shown in SEQ ID NO: 10. “3' untranslated region” comprises the nucleotide sequence shown in SEQ ID NO: 11.

For example, a region or site in the RNA sequence derived from HCV may be defined by the nucleotide numbers within the nucleotide sequences of SEQ ID NOs. 1-12 which are determined by alignment of the RNA sequence and the nucleotide sequences shown in the SEQ ID NOs. 1-12. In the alignment, a gap, addition, deletion, substitution and the like may be present.

In more preferable embodiment of the present invention, the 5' untranslated region, the core protein coding sequence, the E1 protein coding sequence, the E2 protein coding sequence, the NS2 protein coding sequence, the NS3 protein coding sequence, the NS4A protein coding sequence, the NS4B protein coding sequence, the NS5A protein coding sequence, the NS5B protein coding sequence, and the 3' untranslated region, which are contained in the full length HCV replicon RNA, preferably comprises the nucleotide sequences shown in SEQ ID NOs. 1-11, respectively.

A preferred embodiment of the full length HCV replicon RNA according to the present invention is a replicon RNA comprising nucleotide sequences shown in SEQ ID NOs: 1-11, at least one marker gene and/or reporter gene, and at lease one IRES sequence.

“Selectable marker gene” in the present invention means a gene conferring selectability to a cell so that only the cell expressing the gene can be selected. A general example of the selectable marker gene includes an antibiotic resistant gene. The examples of the selectable marker gene preferred in the present invention include a neomycin resistance gene, a thymidine kinase gene, a kanamycin resistance gene, a pyrithiamine resistance gene, an adenylyl transferase gene, a Zeocin resistance gene and a puromycin resistance gene. The neomycin resistance gene and the thymidine kinase gene are preferred, and the neomycin resistance gene is more preferred. However, the selectable marker gene in the present invention is not limited to these genes.

Furthermore in the present invention, “reporter gene” means a marker gene encoding a gene product that may act as an indicator for the expression of the gene. General examples of a reporter gene include structural genes of enzymes that catalyze light emitting reaction or color reaction. Preferred examples of the reporter gene in the present invention include transposon Tn9-derived chloramphenicol acetyltransferase gene, *Escherichia coli*-derived β-glucuronidase gene or β-galactosidase gene, luciferase gene, a green fluorescent protein gene, aequorin gene from jellyfish, and secreted placental alkaline phosphatase (SEAP) gene. However, the reporter gene in the present invention is not limited to these genes.

Either only one or both of the above selectable marker gene and reporter gene may be contained in a full length replicon RNA. One or more of the selectable marker genes or reporter genes may be present in one full length HCV replicon RNA.

In the present invention, “IRES sequence” means an internal ribosome entry site that allows translation to be initiated by binding ribosomes within the inside of the RNA. Preferred examples of IRES sequence in the present invention include, but are not limited to, EMCV IRES (the internal ribosome entry site of encephalomyocarditis virus), FMDV IRES and HCV IRES. EMCV IRES and HCV IRES are more preferred, and EMCV IRES is the most preferred sequence.

A still more preferred embodiment of a full length HCV replicon RNA according to the present invention is an RNA comprising the nucleotide sequence shown in SEQ ID NO: 13. Furthermore, a replicon RNA comprising a nucleotide sequence derived from the nucleotide sequence shown in SEQ ID NO: 13 by deletion, substitution or addition of 1-100, preferably 1-30, more preferably 1-10, still more preferably 1-6 and most preferably one to several (2-5) nucleotides in the nucleotide sequence shown in SEQ ID NO: 13 and having autonomous replication ability and virus particle production ability is a preferred embodiment of the full length HCV replicon RNA and also included in the scope of the present invention.

The full length HCV replicon RNA according to the present invention may also contain an RNA encoding an optional foreign gene to be expressed within a cell into which the full length replicon RNA is introduced. The RNA encoding the foreign gene may also be ligated downstream of the 5' untranslated region or ligated upstream or downstream of a selectable marker gene or a reporter gene, or ligated upstream of the 3' untranslated region. The RNA encoding the foreign gene may be inserted in any site between the core protein coding sequence, the E1 protein coding sequence, the E2 protein coding sequence, the NS2 protein coding sequence, the NS3 protein coding sequence, the NS4A protein coding sequence, the NS4B protein coding sequence, the NS5A protein coding sequence and the NS5B protein coding sequence.

The full length HCV replicon RNA containing the RNA encoding the foreign gene can express a gene product encoded by the foreign gene when it is translated within a cell into which the RNA is introduced. Thus, the full length HCV replicon RNA containing the RNA encoding the foreign gene can be also appropriately used for producing a gene product from the foreign gene within a cell.

The full length HCV replicon RNA according to the present invention may further contain a ribozyme. A ribozyme is ligated downstream of a selectable marker gene and/or a reporter gene so that the selectable marker gene and/or the reporter gene may be cut off by the self cleavage activity of a ribozyme from the IRES sequence, the core protein coding sequence, the E1 protein coding sequence, the E2 protein coding sequence, the NS2 protein coding sequence, the NS3 protein coding sequence, the NS4A protein coding sequence, the NS4B protein coding sequence, the NS5A protein coding sequence and the NS5B protein coding sequence, and the 3' untranslated region.

In the full length HCV replicon RNA according to the present invention, the above described selectable marker gene and/or reporter gene, the sequences encoding viral proteins, and the foreign gene, ribozyme or the like are ligated so that they are translated from the full length HCV replicon RNA in the correct reading frame. Among these sequences, the proteins encoded by the full length replicon RNA are preferably connected to each other via protease cleavage sites and the like, so that the proteins are translated or expressed as a polyprotein, followed by cleaving by protease into each protein.

The present invention also relates to a DNA vector, preferably an expression vector, which encodes the replicon RNA of the present invention.

In the present invention "autonomous replication ability" of RNA means that the RNA is capable of growing autonomously when introduced into the cell. The autonomous replication ability of RNA may be confirmed by the following procedure although it is not limited. Huh7 cells are transfected with the RNA of interest and cultured. RNAs are extracted from the resulting cultured cells and subjected to Northern blot hybridization using a probe capable of specifically detecting the introduced RNA. Detection of the RNA of interest confirms the autonomous replication. Examples of the particular procedure for confirming the autonomous replication ability are illustrated in the descriptions about assay of colony forming ability, confirmation of HCV protein expression, detection of replicon RNA and the like in the Examples of the present specification.

Further, in the present invention, "virus particle production ability" of RNA means that virus particles are generated in a cell when the RNA is introduced into the cell (e.g. cultured cell such as Huh7 cells). The virus particle production ability may be confirmed, for example, by applying for detection the RT-PCR method using primers specific to the RNA to the culture supernatant of the RNA-introduced cell. It may also be confirmed by subjecting the culture supernatant to the sucrose density gradient method to separate virus particles and by detecting HCV protein. Examples of the particular procedure are illustrated in the descriptions about assay of colony forming ability, confirmation of HCV protein expression, detection of replicon RNA and the like in the Examples of the present specification.

2. Preparation of Full Length HCV Replicon RNA

The full length HCV replicon RNA according to the present invention can be prepared using genetic engineering techniques known to persons skilled in the art. The full length HCV replicon RNA may be prepared, but not limited to, for example, using JFH-1 strain as hepatitis C virus of genotype 2a by the following method.

First, DNA corresponding to the entire region of the genomic RNA of JFH-1 strain (SEQ ID NO: 12; this sequence is registered at international DNA data bank under accession No. AB047639) is routinely reconstructed and inserted downstream of an RNA promoter so as to prepare a DNA clone. As used herein, "DNA corresponding to RNA" means a DNA having a nucleotide sequence derived from the nucleotide sequence of the RNA by substituting U (uracil) with T (thymine). The above RNA promoter is preferably contained in a plasmid clone. An example of the preferred RNA promoter is not limited to, but includes T7 RNA promoter, SP6 RNA promoter and SP3 RNA promoter, and T7 RNA promoter is particularly preferred.

Next, the selectable marker gene and/or reporter gene, and DNA encoding the IRES sequence are inserted into the DNA clone described above. It is preferred to insert the selectable marker gene and/or reporter gene downstream of 5' untranslated region and the IRES sequence further downstream.

Subsequently, using the DNA clone prepared as above as a template, RNA is synthesized using RNA polymerase. RNA synthesis can be initiated by a standard procedure from the 5' untranslated region. When the DNA clone is a plasmid clone, RNA can be synthesized using the DNA fragment excised from the plasmid clone with a restriction enzyme, as a template. In addition, it is preferable that the 3' terminus of RNA to be synthesized has the same sequence as the terminus of the 3' untranslated region of the viral genomic RNA, and no other sequences are added or deleted. The thus synthesized RNA is the full length HCV replicon RNA according to the present invention.

3. Preparation of HCV Particles

A recombinant cell that can replicate the full length HCV replicon RNA, preferably continuously replicate (i.e., which has a replicon RNA-replication ability), can be obtained by introducing the full length HCV replicon RNA prepared as described above into a cell. In this specification, a recombinant cell that replicates the full length HCV replicon RNA is referred to as a "full length HCV replicon RNA-replicating cell."

The full length HCV replicon RNA-replicating cell can produce virus particles. The produced virus particles contain the full length HCV replicon RNA in a shell composed of HCV virus proteins. Thus, the virus particles produced by the full length HCV replicon RNA-replicating cell of the present invention are HCV particles. That is, in the present invention, HCV particles can be prepared in a cell culture system by culturing the full length HCV replicon RNA-replicating cells. Preferably, HCV particles can be obtained by culturing the full length HCV replicon RNA-replicating cells and collecting the virus particles generated in the culture (preferably the culture supernatant).

Alternatively, HCV particles can be produced by a recombinant cell which is obtained by introducing the full length HCV genomic RNA into a cell. The full length HCV genomic RNA is replicated with high efficiency in the cell, into which the full length HCV genomic RNA of the present invention (preferably the full length HCV genomic RNA derived from JFH-1 clone, and more preferably RNA having the nucleotide sequence shown in SEQ ID NO: 12) is introduced. In this specification, a cell that replicates the full length HCV genomic RNA is referred to as a "full length HCV genomic RNA-replicating cell". The full length HCV genomic RNA-replicating cells can produce virus particles. The virus particles produced by the full length HCV genomic RNA-replicating cells contain the full length HCV genomic RNA in a shell composed of HCV virus proteins. Thus, the virus particles produced by the cell into which the full length HCV genomic RNA of the present invention is introduced are HCV particles. It is not limited but preferred that HCV particles may be prepared in a cell culture system by culturing the cell into which the full length HCV genomic RNA derived from JFH-1 clone (e.g. RNA having the nucleotide sequence shown in SEQ ID NO: 12) is introduced. For example, HCV particles can be obtained by culturing the cells into which the full length HCV genomic RNA (e.g. RNA having the nucleotide sequence shown in SEQ ID NO: 12) is introduced and collecting virus particles generated in the culture (preferably the culture supernatant).

For a cell into which the full length HCV replicon RNA or the full length HCV genomic RNA described above is to be introduced, any cell can be used, as long as it can be subcultured. Such a cell is preferably a eukaryotic cell, more preferably a human cell, and still more preferably a human liver-derived cell, a human uterine cervix-derived cell or a human fetal kidney-derived cell. Proliferative cells including cancer cell lines, stem cell lines and the like cells can be used preferably, and Huh7 cells, HepG2 cells, IMY-N9 cells, HeLa cells and 293 cells and the like are used more preferably. For these cells, commercially available cells may be utilized, these cells may be obtained from cell depositories, or cell lines established from any cells (e.g., cancer cells or stem cells) may also be used.

Introduction of the full length HCV replicon RNA or the full length HCV genomic RNA into cells can be achieved using any technique known to persons skilled in the art. Examples of such an introduction method include electroporation, particle gun method, lipofection method, calcium phosphate method, microinjection method, DEAE sepharose method and the like. The method using electroporation is particularly preferred.

The full length HCV replicon RNA or the full length HCV genomic RNA may be introduced alone, or may be introduced after being mixed with other nucleic acids. To vary the amount of the full length HCV replicon RNA or the full length HCV genomic RNA while keeping RNA amount to be introduced at a certain level, the desired amount of the full length HCV replicon RNA or the full length HCV genomic RNA to be introduced is mixed with total cellular RNA extracted from the cells, to which the RNA is introduced, to bring the total RNA amount up to a certain level, and then the mixture is used for introduction into cells. The amount of replicon RNA to be used for introducing into cells may be determined according to the introduction method employed, and is preferably between 1 picogram and 100 micrograms, and more preferably between 10 picograms and 10 micrograms.

The full length HCV replicon RNA-replicating cells can be selected utilizing the expression of the selectable marker gene or the reporter gene within the full length HCV replicon RNA. Specifically, for example, such cells subjected to the treatment for cellular introduction of the full length HCV replicon RNA may be cultured in a medium, in which the cells can be selected due to the expression of the selectable marker gene. Alternatively, after culturing the cells subjected to the treatment for cellular introduction of the full length HCV replicon RNA, the expression of the reporter gene (for example fluorescent protein) may be detected.

As an example, when the full length HCV replicon RNA contains a neomycin resistance gene as a selectable marker gene, cells subjected to electroporation method with the full length HCV replicon RNA, are seeded into a culture dish. After culturing 12 to 72 hours, preferably 16 to 48 hours, G418 (neomycin) is added to the culture dish at a concentration of 0.05 milligrams/milliliter to 3.0 milligrams/milliliter. The cells are continuously cultured for preferably 10 days to 40 days and more preferably 14 days to 28 days after seeding, while changing the culture medium twice a week, and the cells that is replicating the introduced full length HCV replicon RNA, can be selected as a colony by staining viable cells with crystal violet.

Cells can be cloned from the formed colonies by standard procedure. The thus obtained cell clone that replicates the full length HCV replicon RNA is referred to as "a full length HCV replicon RNA-replicating cell clone" in this specification. The full length HCV replicon RNA-replicating cell of the present invention includes the full length HCV replicon RNA-replicating cell clone.

For the full length HCV replicon RNA-replicating cell, actual replication of the full length HCV replicon RNA in the cell or cell clone can be confirmed by detecting the replicated full length HCV replicon RNA, confirming that the selectable marker or reporter gene of the full length HCV replicon RNA is not integrated in the host genomic DNA and further detecting HCV proteins.

The full length HCV replicon RNA that has been replicated may be detected according to any RNA detection method known to persons skilled in the art. For example, the full length HCV replicon RNA can be detected in total RNA extracted from the cell by the Northern hybridization method using a DNA fragment specific to the full length HCV replicon RNA as a probe.

Furthermore, the absence of the integrated selectable marker gene or reporter gene in the full length HCV replicon RNA in the host genomic DNA can be confirmed by, but not limited to, for example, performing PCR for the genomic DNA extracted from the cell to amplify at least a part of the selectable marker gene or reporter gene, and then confirming the absence of the amplified product. Since it is considered that in the cell, for which the amplified product is confirmed, the selectable marker gene or reporter gene may have been integrated in the host genome, it is possible that the full length HCV replicon RNA itself is not replicated. In this case, the replication of the full length HCV replicon RNA can be further confirmed by detecting HCV proteins as described below.

An HCV protein can be detected by, for example, reacting an antibody against the HCV protein to be expressed from the introduced full length HCV replicon RNA with the extracted cellular proteins. This method can be carried out by any protein detection method known to persons skilled in the art. Specifically, HCV protein can be detected by, for example, blotting a protein sample extracted from the cell onto a nitrocellulose membrane, reacting an anti-HCV protein antibody (e.g., anti-NS3 specific antibody or antiserum collected from a hepatitis C patient) with the nitrocellulose membrane and detecting the anti-HCV protein antibody. If the HCV protein is detected among the extracted cellular proteins, it can be concluded that this cell replicates the full length HCV replicon RNA and expresses the HCV protein.

The virus particle production ability of the full length HCV replicon RNA-replicating cells or the full length HCV genomic RNA-replicating cells may be confirmed by any virus detection method known to the persons skilled in the art. For example, the culture supernatant of cells which are suspected of producing virus particles is fractionated through the sucrose density gradient, and the density of fraction, HCV core protein concentration, and amount of the full length HCV replicon RNA or the full length HCV genomic RNA are determined for each fraction. As a result, if the peak of the core protein coincides with that of the full length HCV replicon RNA or the full length HCV genomic RNA, and the density of the fraction showing the detected peaks (e.g. 1.18-1.20 mg) is smaller than the density of the equivalent fraction as obtained by fractionating the culture supernatant treated with 25% NP40 (Polyoxyethylene(9)Octylphenyl Ether), the cells can be considered to have a virus particle production ability.

HCV virus particles released in the culture supernatant can be detected, for example, using antibodies to the core protein, the E1 protein or the E2 protein. Also, the presence of HCV virus particles can be detected indirectly by amplifying and detecting the full length HCV replicon RNA in the culture supernatant by the RT-PCR method using specific primers.

4. Infection of Another Cell with HCV Particles of the Present Invention

HCV virus particles of the present invention have an ability to infect a cell (preferably an HCV permissive cell). The present invention relates also to a method for producing a hepatitis C virus-infected cell comprising culturing the full length HCV replicon RNA-replicating cell or the full length HCV genomic RNA-replicating cell, and infecting another cell (preferably an HCV permissive cell) with virus particles in the thus obtained culture (preferably culture supernatant). In the present invention, the HCV permissive cell means a cell which is susceptible to HCV, and is preferably, but not limited to, a hepatic cell or a lymphoid lineage cell. In particular, the hepatic cell includes a primary hepatocyte, Huh7 cell, HepG2 cell, IMY-N9 cell, HeLa cell, 203 cell and the like. The lymphoid lineage cell includes, but not limited to, Molt4 cell, HPB-Ma cell, Daudi cell and the like.

When a cell (e.g., an HCV permissive cell) is infected with HCV particles produced by the full length HCV replicon RNA-replicating cell of the present invention, the full length HCV replicon RNA is replicated and virus particles are also formed in the infected cell. Since the cell infected with virus particles generated in the full length HCV replicon RNA-replicating cell expresses the selectable marker gene and/or reporter gene, the infected cell can be selected and/or detected by utilizing the expression. By infecting a cell with virus particles generated in the full length HCV replicon RNA-replicating cell of the present invention, the full length HCV replicon RNA is replicated in the cell and furthermore the virus particles can be produced.

Still further, by infecting a cell (e.g. an HCV permissive cell) with HCV particles generated in the full length HCV genomic RNA-replicating cell of the present invention, the full length HCV genomic RNA is replicated and virus particles are also formed in the infected cell. By infecting a cell with virus particles generated in the full length HCV genomic RNA-replicating cell of the present invention, the full length HCV genomic RNA is replicated in the cell and furthermore the virus particles can be produced.

HCV virus particles generated in the full length HCV replicon RNA-replicating cell or the full length HCV genomic RNA-replicating cell can infect HCV permissive animals such as chimpanzee and the like and induce hepatitis caused by HCV therein.

5. Other Embodiments of the Present Invention

The full length HCV replicon RNA is replicated with a high efficiency in the full length HCV replicon RNA-replicating cell of the present invention. Also the full length HCV genomic RNA is replicated with a high efficiency in the full length HCV genomic RNA-replicating cell of the present invention. Thus, the full length HCV replicon RNA or the full length HCV genomic RNA can be produced with a high efficiency using the full length HCV replicon RNA-replicating cell or the full length HCV genomic RNA-replicating cell of the present invention.

In the present invention the full length HCV replicon RNA can be produced by culturing the full length HCV replicon RNA-replicating cell, extracting RNA from the culture (cultured cells and/or culture medium), subjecting the RNA to the electrophoresis method, and isolating and purifying the full length HCV replicon RNA. The full length HCV genomic RNA can also be produced by using the full length HCV genomic RNA-replicating cell by the similar method. The RNA produced by such a way comprises the full length genomic sequence of hepatitis C virus. In this case the full length genomic sequence of hepatitis C virus may be interrupted by the selectable marker gene and/or reporter gene and the IRES sequence. By the method for producing the RNA comprising the full length genomic sequence of hepatitis C virus being provided, more detailed analysis of hepatitis C virus genome becomes possible.

Further, the full length HCV replicon RNA-replicating cell or the full length HCV genomic RNA-replicating cell of the present invention can be suitably used for producing HCV protein. HCV protein may be produced by any method known to persons skilled in the art. For example, HCV protein may be produced by introducing the full length HCV replicon RNA or the full length HCV genomic RNA into a cell, culturing the recombinant cell and collecting proteins from the culture thus obtained (cultured cells and/or culture medium) by the known procedure.

Further, the HCV virus particles of the present invention may possess hepatotropism. Thus a hepatotropic virus vector can be produced using the full length HCV replicon RNA of the present invention. This virus vector is suitably used for gene therapy. In the present invention, a foreign gene can be introduced into a cell, replicated in the cell and expressed, by integrating an RNA encoding the foreign gene into the full length HCV replicon RNA or full length HCV genomic RNA and introducing the integrated RNA into the cell. Further, by preparing an RNA in which the E1 protein coding sequence and/or the E2 protein coding sequence of the full length HCV replicon RNA or full length HCV genomic RNA are replaced with an outer shell protein coding sequence of virus derived from other biological species, it becomes possible to infect the RNA to various biological species. In this case also, a foreign gene is integrated into the full length HCV replicon RNA or full length HCV genomic RNA and this can be used as a hepatotropic virus vector for expressing the foreign gene in hepatocytes.

The present invention relates also to a method for producing a virus vector carrying a foreign gene, comprising inserting an RNA encoding the foreign gene into RNA comprising the nucleotide sequence shown in SEQ ID NO: 12, introducing it into a cell and culturing the cell to produce virus particles.

The present invention provides a hepatitis C vaccine comprising HCV particles of the present invention or a part thereof and a method for producing the hepatitis C vaccine comprising HCV particles of the present invention or a part thereof.

In particular, HCV particles as prepared above may be used directly as a vaccine or may be used after attenuating or inactivating by the known method in the art. For example, a HCV vaccine stock solution can be obtained by purifying the HCV particles using column chromatography, filtration, centrifugation and the like. An attenuated live HCV vaccine or an inactivated HCV vaccine may be prepared from this HCV vaccine stock solution. Inactivation of virus can be carried out by reacting an inactivation agent such as formalin, β-propiolactone, glutardialdehyde and the like with the virus, by adding and mixing to, for example, virus suspension (Appaiahgari et al., Vaccine, (2004) 22(27-28), p. 3669-3675).

For the production of the vaccine of the present invention, it is possible to use HCV replicon RNA in which the pathogenicity is attenuated or lost by an introduced mutation using the publicly known art.

The vaccine of the present invention is prepared for administration as a solution or suspension. It is also possible to be prepared in the form of solid material suitable for dissolving or suspending in liquid. The preparation may be emulsified or capsulized in liposome. The active immunogenic component such as HCV particles is often mixed with an excipient which is pharmaceutically acceptable and appropriate for the active ingredient. A suitable excipient includes, for example, water, physiological saline, dextrose, glycerol, ethanol and mixtures thereof. Further, if desired, the vaccine may contain a small amount of auxiliary agent (e.g. humidifier or emulsifier), pH buffer and/or adjuvant for enhancing the efficacy of the vaccine. Examples of effective adjuvant include but not limited to following substances: aluminum hydroxide, N-acetyl-muramyl-L-threonyl-D-isoglutamine (thr-MDP), N-acetyl-nor-muramyl-L-alanyl-D-isoglutamine (CGP11637, nor-MDP), N-acetyl muramyl-L-alanyl-D-isoglutaminyl-L-alanine-2-(1'-2'-dipalmitoyl-sn-glycero-3-hydroxyphosphryloxy)-ethylamine (CGP19835A, referred to as MTP-PE) and RIBI. RIBI contains three components extracted from bacteria, that is monophosphoryl lipid A, trehalose dimycolate and cell wall skelton (HPL+TDM+CWS), in 2% squalene/Tween® 80 emulsion. Efficacy of an adjuvant can be determined by measuring the amount of antibody against the immunogenic HCV particles which is produced by administrating the vaccine composed of HCV particles.

The present vaccine is normally administered parenterally, for example by injection such as subcutaneous or intramuscular injection. Other dosage forms suitable for the other administration route include suppository and, in some case, oral formulation.

If desired, one or more of the above compounds having adjuvant activity may be added to the HCV vaccine. The adjuvants are a non-specific stimulating factor for this immune system and enhance the immune response to HCV vaccine in the host. Particular examples of adjuvant known in this technical art include complete Freund's adjuvant, incomplete Freund's adjuvant, vitamin E, nonionic block polymer, muramyldipeptide, saponin, mineral oil, vegetable oil and Carbopol. Adjuvants especially suitable for application for the mucosal membrane include, for example, *E. coli* heat labile toxin (LT) and cholera toxin (CT). Other suitable adjuvants include, for example, aluminum hydroxide, aluminum phosphate or aluminum oxide, oil emulsion (e.g. Bayol (Registered Trade Mark) or Marcol 52 (Registered Trade Mark)), saponin or vitamin E solubilisate. In the preferred embodiment, the vaccine of the present invention contains an adjuvant.

For examples, for the injections to be administered subcutaneously, intradermally, intramuscularly and intravenously, particular examples of pharmaceutically acceptable carriers and diluents, which can be included in the HCV vaccine of the present invention, include stabilizers, carbohydrates (e.g. sorbitol, mannitol, starch, sucrose, glucose, dextran), proteins such as albumin or casein, protein-containing materials such as bovine serum albumin or skim milk, and buffers (e.g. phosphate buffer).

Conventional binders and carriers used for a suppository include, for example, polyalkyleneglycol or triglycerides. The suppository can be formulated from a mixture containing the active ingredient in the range of 0.5% to 50%, preferably 1% to 20%. An oral formulation may contain normally used excipients. Such excipients include, for example, mannitol, lactose, starch, magnesium stearate, sodium saccharine, cellulose, magnesium carbonate and the like of pharmaceutical grade.

The vaccine of the present invention can be produced in the dosage forms of solutions, suspensions, tablets, pills, capsules, extended release formulations or powders and contain the active ingredient (virus particles or a part thereof) at 10-95%, preferably 25-70%.

The vaccine of the present invention is administered by the method suitable for the dosage forms and at the effective amount for prevention and/or treatment. The dosage amount is in the range from 0.01 μg to 100,000 μg and this is dependent on the patient to be treated, the antibody forming capability in the immune system of the patient, and desired level of protection. It is also dependent of the administration route such as oral, subcutaneous, intradermal, intramuscular, intravenous and the like.

This vaccine may be administered by the single administration schedule or preferably by the complex administration schedule. In the complex administration schedule, 1-10 individual administrations are carried out at the start of administration, followed by administrations at intervals required to sustain and/or to enhance the immune response. For example, another type of administration may be given as the second administration 1-4 months later. If necessary, the administration may be continued several months later. The administration regimen is, at least partially, determined according to the need for the individual patient and is dependent on the judgment of the attending physician.

Further, the vaccine containing immunogenic HCV particles may be co-administered with other immune controlling agent (e.g. immunoglobulin).

The HCV particle vaccine can be used preventively against the possible new HCV infection by administering to healthy individuals to induce the immune response to HCV. The HCV particle vaccine can also be used as a therapeutic vaccine to eliminate HCV by administering to patients infected with HCV and inducing a strong immune response to HCV in the body.

The full length HCV replicon RNA-replicating cell or full length HCV genomic RNA-replicating cell or the hepatitis C virus-infected cell, which is infected with virus particles generated in these cells, can be used as a test system for screening a substance (anti-hepatitis C virus substance) which promotes or inhibits, for example, the replication of hepatitis C virus, re-construction of virus particles and release of virus particles. In particular, for example, the substance which promotes or inhibits the growth of hepatitis C virus can be screened by determining whether the test substance promotes or inhibits the replication of the full length HCV replicon RNA or the full length HCV genomic RNA, or formation or release of the virus particles, culturing these cells in the presence of the test substance and detecting the full length HCV replicon RNA or the full length HCV genomic RNA, or the virus particles in the obtained culture. In this case, the detection of the full length HCV replicon RNA or the full length HCV genomic RNA in the culture may be carried out by determining the amount, the ratio or the presence of the full length HCV replicon RNA or the full length HCV genomic RNA in the RNA preparation extracted from cells described above. The detection of the virus particles in the culture (mainly culture supernatant) may be carried out by measuring the amount, the ratio or the presence of HCV protein in the culture supernatant.

Furthermore, it can be investigated whether immunoglobulin purified from the serum of a HCV infected patient can prevent the infection with HCV particles of the present invention, by detecting virus particles in this culture. In this test, sera from mice, rats, rabbits and the like, which has been immunized with the HCV virus particles of the present invention, can be used. Immunization by a part of HCV protein, the HCV gene and the like may be utilized. This test may be performed on the other infection preventive substances in a similar manner.

The antibodies of the present invention which are generated against HCV virus particle of the present invention include polyclonal antibodies and monoclonal antibodies. When the polyclonal antibody is preferred, selected mammals (e.g. mouse, rabbit, goat, sheep, horse and the like) are immunized with the HCV particles of the present invention as the first step. Sera are collected from immunized animals and processed by the known procedure. If the sera containing polyclonal antibodies to HCV epitopes contain antibodies to other antigens, these sera may be purified by immunoaffinity chromatography. The methods for generating polyclonal antisera and the methods for treatment of it are known in the art. Polyclonal antibodies may be isolated from mammals already infected with HCV.

Monoclonal antibodies to HCV epitopes can be produced easily by persons skilled in the art. The common method for producing hybridoma which generates monoclonal antibodies is known. For example, the methods described in Current Protocols in Immunology (John Wiley & Sons, Inc.) can be used.

The monoclonal antibody-generating cell lines may be produced by cell fusion, or by other method such as direct transformation of B lymphocyte with tumor gene DNA or transduction with Epstein-Barr virus.

Monoclonal antibodies and polyclonal antibodies obtained by these methods are useful for diagnosis, treatment and prevention of HCV.

The antibodies produced by using the HCV particles of the present invention are administered with pharmaceutically acceptable solubilizer, additive, stabilizer, buffer and the like. Any administration route can be chosen but subcutaneous, intradermal and intramuscular administrations are preferred and intravenous administration is more preferred.

The HCV particles, generated in the full length HCV replicon RNA-replicating cell or the full length HCV genomic RNA-replicating cell of the present invention, and HCV permissive cell can be used as a test system for screening a substance which may stimulate or inhibit the binding of HCV to cells. In particular, for example, substances, which may promote or inhibit the growth of hepatitis C virus, can be screened by culturing the HCV particles generated in the full length HCV replicon RNA-replicating cell of the present invention together with HCV permissive cell in the presence of a test substance, detecting the full length HCV replicon RNA or virus particles in the culture obtained and determining whether the test substance promotes or inhibits the replication of the replicon RNA or formation of virus particles Such detections of full length HCV replicon RNA or full length HCV genomic RNA, or virus particles can be carried out according to the technique described above or following Examples. The test system described above can be used for the production and evaluation of the preventive, therapeutic or diagnostic agents of hepatitis C virus infection.

In particular, examples of the usage of the test system of the present invention described above include following:

(1) Screening for a substance which inhibits growth and infection of HCV

The substances which inhibit growth and infection of HCV include, for example, organic compounds which affect the growth and infection of HCV directly or indirectly, anti-sense oligonucleotide or the like which affect the growth of HCV or translation of HCV protein directly or indirectly by hybridizing with the target sequence in the HCV genome or its complementary strand.

(2) Evaluation of various substances which have antivirus activity in cell culture.

The aforementioned various substances include substances obtained by rational drug design or high-throughput screening (for example, purified and isolated enzyme).

(3) Identification of a new target for the treatment of patients infected with HCV For example, the full length HCV replicon RNA-replicating cell or the full length HCV genomic RNA-replicating cells of the present invention can be used for identifying host cellular protein which may play an important role for the growth of HCV (4) Evaluation of the ability of HCV for acquiring resistance to drugs and the like, and identification of the mutation related to the resistance (5) Production of virus protein as an antigen usable for development, production and evaluation of diagnostic and therapeutic agents for hepatitis C virus infection (6) Production of virus protein as an antigen usable for development, production and evaluation of the vaccine for hepatitis C virus infection and production of attenuated HCV (7) Production of monoclonal or polyclonal antibodies for diagnosis and treatment of hepatitis C virus infection.

The present invention will be described more specifically based on the following examples and drawings. However, the technical scope of the present invention is not limited to these examples.

Example 1

Preparation of the Full Length HCV Replicon RNA Derived from the Full Length HCV Genomic RNA

(A) Construction of Expression Vector

Plasmid DNAs were constructed in which DNAs (JFH-1 clone) containing the full length genomic cDNA of hepatitis C virus JFH-1 strain (genotype 2a) that had been isolated from a patient with fulminant hepatic failure were inserted downstream of T7 RNA promoter sequence in pUC19 plasmids.

In particular, the RT-PCR fragments obtained by amplifying viral RNA of JFH-1 strain were cloned into pGEM-T EASY vectors (Promega) to obtain plasmids, pGEM1-258, pGEM44486, pGEM317-849, pGEM617-1323, pGEM1141-2367, pGEM2285-3509, pGEM3471-4665, pGEM4547-5970, pGEM5883-7003, pGEM6950-8035, pGEM7984-8892, pGEM8680-9283, pGEM9231-9634 and pGEM9594-9678 (see Non-patent document 6). The viral genomic RNA-derived cDNAs contained in such plasmids were ligated together by using PCR method and restriction enzymes to clone the full length viral genomic cDNA. The T7R RNA promoter sequence was inserted upstream of the full length viral genomic cDNA. Hereinafter, the plasmid DNA constructed in this way is referred to as pJFH1 (upper part of FIG. 1). The preparation of JFH-1 clone described above has been described in Patent Document 1 and Non-Patent Document 3. Further, the nucleotide sequence of the full length cDNA of JFH-1 clone is registered in international DNA data bank (DDBJ/EMBL/GenBank) with Accession No. AB047639.

Next, plasmid DNA pFGREP-JFH1 was constructed by inserting the EMCV-IRES (internal ribosome entry site of encephalomyocarditis virus) and the neomycin resistant gene (neo; also referred to as neomycin phosphotransferase gene) between the 5' untranslated region and the core region of pJFH1 plasmid DNA (lower part of FIG. 1). This construction procedure was according to the previous publication (Non-Patent Document 4). Further, mutant plasmid clones pJFH1/GND and pFGREP-JFH1/GND were prepared by introducing a mutation which changed the amino acid motif GDD, which corresponded to the active center of RNA polymerase encoded by the NS5B region in pJFH1 and pFGREP-JFH1, to GND. Since the amino acid sequence of the active site of the NS5B protein coded by the mutant clones pJFH1/GND and pFGREP-JFH1/GND is changed, active NS5B protein which is needed for replicating the replicon RNA can not be expressed from the mutant clones.

Further, pFGREP-JFH1/Luc was prepared as a reporter gene-introduced expression vector by inserting the luciferase gene between the MluI site of 415$^{th}$ to 420$^{th}$ and the PmeI site of 2075$^{th}$ to 2082$^{nd}$ of pFGREP-JFH1 to replace the neomycin resistant gene of pFGREP-JFH1 with the luciferase gene. Also, a mutant pFGREP-JFH1/Luc/GND, in which the GDD motif of the active center of NS5b RNA polymerase was changed to GND, was prepared by mutating G at 10933$^{rd}$ of pFGREP-JFH1/Luc to A.

pFGREP-JFH1/EGFP, in which the neomycin resistant gene of pFGREP-JFH1 was replaced with the green fluorescent protein gene, was prepared by inserting the green fluorescent protein gene between the MluI site of 415$^{th}$ to 420$^{th}$ and the PmeI site of 1142$^{nd}$ to 1149$^{th}$ of pFGREP-JFH1. Also, a mutant pFGREP-JFH1/EGFP/GND, in which the GDD motif of the active center of NS5b RNA polymerase was changed to GND, was prepared by mutating G at 10000$^{th}$ of pFGREP-JFH1/EGFP to A.

pFGREP-JFH1/SEAP was prepared by inserting the secretary placental alkaline phosphatase gene between the MluI site of 415$^{th}$ to 420$^{th}$ and the PmeI site of 1982$^{nd}$ to 1989$^{th}$ of pFGREP-JFH1 to replace the neomycin resistant gene of pFGREP-JFH1 with the secretary placental alkaline phosphatase gene. Also, a mutant pFGREP-JFH1/SEAP/GND, in which the GDD motif of the active center of NS5b RNA polymerase was changed to GND, was prepared by mutating G at 10840$^{th}$ of pFGREP-JFH1/SEAP to A.

(B) Preparation of Full Length HCV Genomic RNA and Full Length HCV Replicon RNA The expression vectors constructed as above, pJFH1, pJFH1/GND, pFGREP-JFH1 and pFGREP-JFH1/GND were digested with restriction enzyme XbaI to prepare template DNAs for the synthesis of the full length HCV genomic RNA and full length HCV replicon RNA. Subsequently 10-20 μg each of XbaI fragment was treated with 20 U of Mung Bean Nuclease in 50 μl reaction solution by incubating at 30° C. for 30 min. Mung Bean Nuclease is an enzyme which catalyzes a reaction that involves selectively digesting single strand parts of double stranded DNA. Normally, if RNA is synthesized using the above XbaI fragments as it is as templates, replicon RNAs having 4 extra-bases of CUGA, which is a part of the XbaI recognition site, at 3' terminus are synthesized. Therefore, in this example, 4 bases of CUGA were removed from the XbaI fragments by treating the XbaI fragments with Mung Bean Nuclease. Subsequently, the post-Mung Bean Nuclease treatment solution containing the XbaI fragments was subjected to standard protein removal treatment to obtain purified XbaI fragments without the 4 bases, CUGA, as the template DNA to be used below.

Next, RNA was synthesized in vitro from this template DNA using T7 RNA polymerase. A MEGAscript (Ambion Co.) was used for the RNA synthesis. 20 μl reaction mixture containing 0.5-1.0 microgram of the template DNA was reacted according to the instruction of the manufacturer.

After the RNA synthesis, DNase (2 U) was added to the reaction mixture and reacted at 37° C. for 15 minutes, and then RNA was extracted with acid-phenol treatment to remove the template DNA. RNAs synthesized in this way from the above template DNAs derived from pJFH1, pJFH1/GND, pFGREP-JFH1 and pFGREP-JFH1/GND were referred to as rJFH1, rJFH1/GND, rFGREP-JFH1 and rFGREP-JFH1/GND, respectively. The nucleotide sequences of these RNAs are shown in SEQ ID NO: 12, 13, 14 and 15 for rJFH-1, rFGREP-JFH1, rJFH1/GND and rFGREP-JFH1/GND, respectively. rJFH1 is an example of the full length HCV genomic RNAs of the present invention which has the same sequence structure as the full length HCV genome of JFH-1 strain. rFGREP-JFH1 is an example of the full length HCV replicon RNA of the present invention.

Subsequently, rFGR-JFH1/Luc (SEQ ID NO:21), rFGR-JFH1/Luc/GND ((SEQ ID NO:22), rFGR-JFH1/EGFP (SEQ ID NO:23), rFGR-JFH1/EGFP/GND (SEQ ID NO:24), rFGR-JFH1/SEAP (SEQ ID NO:25) and rFGR-JFH1/SEAP/GND (SEQ ID NO:26), which were HCV replicon RNAs, were produced by using as templates the expression vectors prepared as above, pFGREP-JFH1/Luc, pFGREP-JFH1/Luc/GND, pFGREP-JFH1/EGFP, pFGREP-JFH 1/EGFP/GND, pFGREP-JFH 1/SEAP and pFGREP-JFH 1/SEAP/GND, respectively.

Example 2

Replication of the Full Length HCV Genomic RNA in Cell and Generation of Virus Particles

(C) Replication of the Full Length HCV Genomic RNA in Cell and Generation of Virus Particles Various amount of the full length HCV genomic RNA (rJFH1 or rJFH1/GND) synthesized as above was mixed with total RNA extracted from Huh7 cells to bring the amount of RNA up to 10 μg. Subsequently the mixed RNA was introduced into Huh7 cells by electroporation method. Huh7 cells subjected to the electroporation treatment were seeded in culture dishes. After incubating for 12, 24, 48 and 72 hours, cells were collected, RNA was extracted and analyzed by the Northern blot method. The Northern blot analysis was carried out according to Molecular Cloning, A laboratory Manual, 2nd edition, J. Sambrook, E. F. Fritsch, T. Maniatis, Cold Spring Harbor Laboratory Press (1989). In particular, RNA extracted from cells after the incubation was subjected to denaturing agarose gel electrophoresis and RNA was transferred to a positively charged nylon membrane after the electrophoresis. $^{32}P$ labeled DNA or RNA probe prepared from pJFH1 was hybridized to the aforementioned RNA transferred on the membrane. The membrane was washed and exposed to a film to detect RNA bands specific to the full length HCV genomic RNA of JFH-1 clone.

Figure 2:
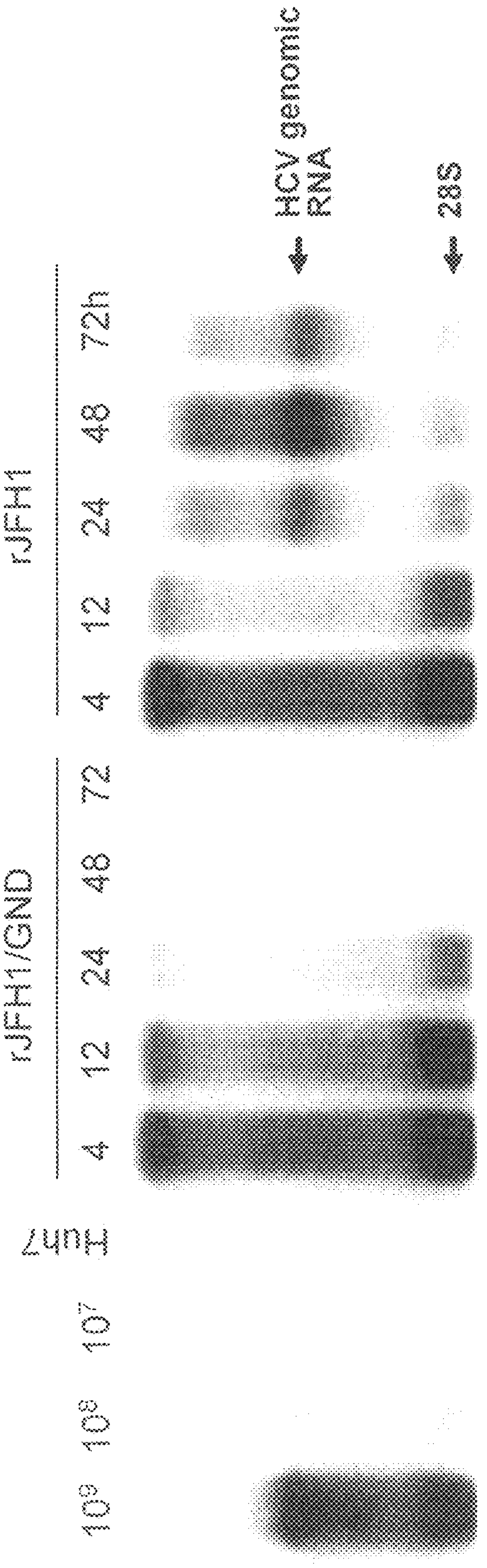
FIG. 2 is a photograph showing the result of a Northern blot analysis demonstrating the replication of rJFH-1 in Huh7 cells to which the full length HCV genomic RNA, rJFH-1, has been introduced.

As shown in FIG. 2, when rJFH1/GND was transfected into the cells, band of the introduced RNA was confirmed as a weak signal at 4 hours after the transfection, but the signal was getting weaker with the passage of time and the signal from the band was almost undetectable at 24 hours after the transfection. In contrast, when rJFH1 was transfected, the signal intensity of band of the introduced. RNA was weakened at first as was the case of rJFH1/GND between 4-12 hours after the transfection but clear signal of the RNA band was confirmed after 24 hours of the transfection. The confirmed signal was specific to the HCV genomic RNA. That is, it was considered that some introduced full length HCV genomic RNAs were replicated and grown. No replication was observed for rJFH1/GND, in which the active motif of NS5B that is RNA replicative enzyme was mutated, indicating that the activity of NS5B is important for the replication of the full length HCV genomic RNA. Further, same experiments were carried out for the full length genomic RNA derived from hepatitis C virus such as H77 strain (Non Patent Document 7), J6 strain (Non Patent Document 8) and JCH1 strain which was isolated from chronic hepatitis by the present inventors (Non Patent Document 6), all of which had been isolated earlier, but no replication of the full length HCV genomic RNA was confirmed for these strains.

Figure 3:
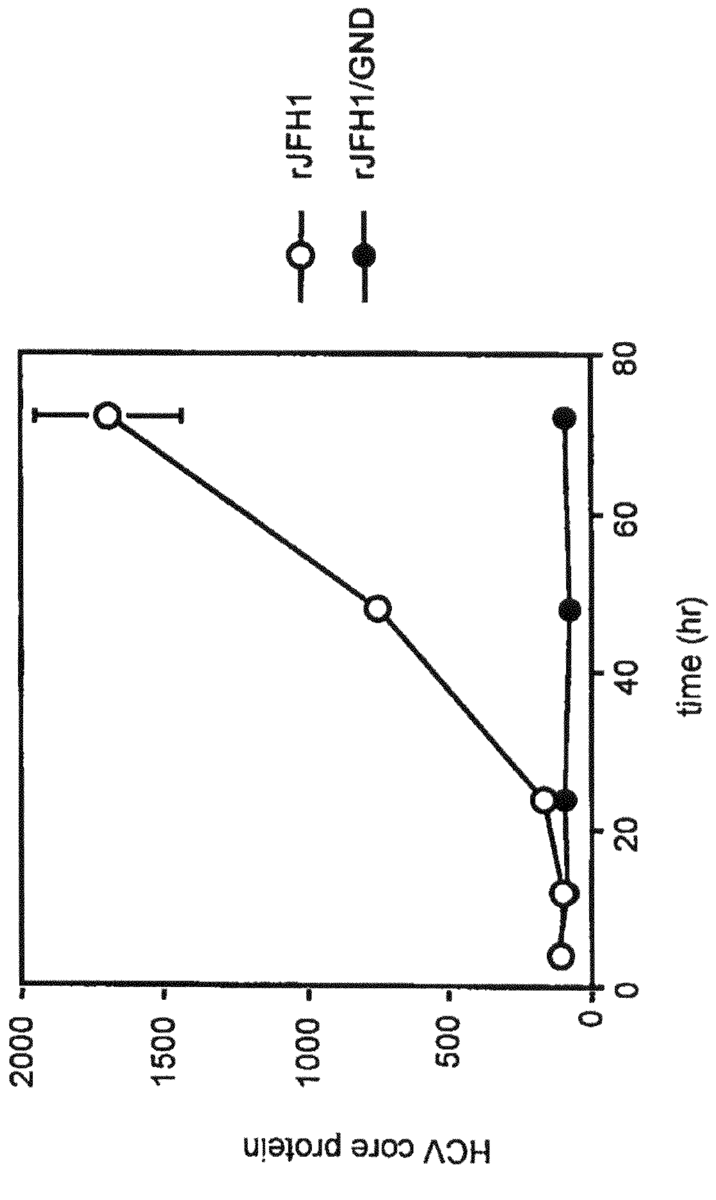
FIG. 3 shows the result of HCV core protein quantitation in the culture medium. The open circle represents cells into which rJFH1 has been introduced, and the closed circle represents cells to which rJFH1/GND has been introduced.

(D) Detection of HCV Virus Particles in Culture Medium of Transfected Cell Culture The electroporation-treated Huh7 cells as described above were seeded in culture dishes and cultured for 12, 24, 48 and 72 hours and then HCV core protein was assayed in the culture supernatant. The assay was carried out according to the Ortho HCV antigen IRMA test (Non Patent Document 9). As shown in FIG. 3, the core protein was detected in the culture supernatant 48 and 72 hours after the transfection with rJFH1. To examine whether this core protein is secreted as virus particles, the culture medium 72 hours after the transfection with rJFH1 was fractionated through the sucrose density gradient. In a centrifuge tube 2 ml of 60% (wt/wt) sucrose solution (dissolved in 50 mM Tris pH7.5/0.1 M NaCl/1 mM EDTA), 1 ml of 50% sucrose solution, 1 ml of 40% sucrose solution, 1 ml of 30% solution, 1 ml of 20% sucrose solution and 1 ml of 10% sucrose solution were layered and 4 ml of the sample culture supernatant was overlaid thereon. This was centrifuged in a Beckman rotor SW41 Ti at 400,000 RPM, at 4° C. for 16 hours. After the centrifugation, this was collected in fractions of 0.5 ml each from the bottom of the tube. The density, the concentration of HCV core protein and the amount of full length HCV genomic RNA in each fraction were determined. Detection of the full length HCV genomic RNA with a quantitative RT-PCR method was carried out by detecting RNA of the 5' untranslated region of the full length HCV genomic RNA, according to Takeuchi T, Katsume A, Tanaka T, Abe A, Inoue K, Tsukiyama-Kohara K, Kawaguchi R, Tanaka S, Kohara M, "Real-Time detection system for quantification of Hepatitis C virus genome", Gastroenterology 116: 636-642 (1999). In particular, the full length HCV genomic RNA contained in RNA extracted from the cell was PCR amplified using synthetic primers, R6-130-S17: 5'-CGGGAGAGCCATAGTGG-3' (SEQ ID NO:16), R6-290-R19: 5'-AGTACCACAAGGCCTTTCG-3' (SEQ ID NO:17) and TaqMan Probe: R6-148-S21FT, 5'-CTGCGGAACCGGTGAGTACAC-3' (SEQ ID NO:18), and EZ rTth RNA PCR kit, and then detected by ABI Prism 7700 sequence detector system.

Figure 4:
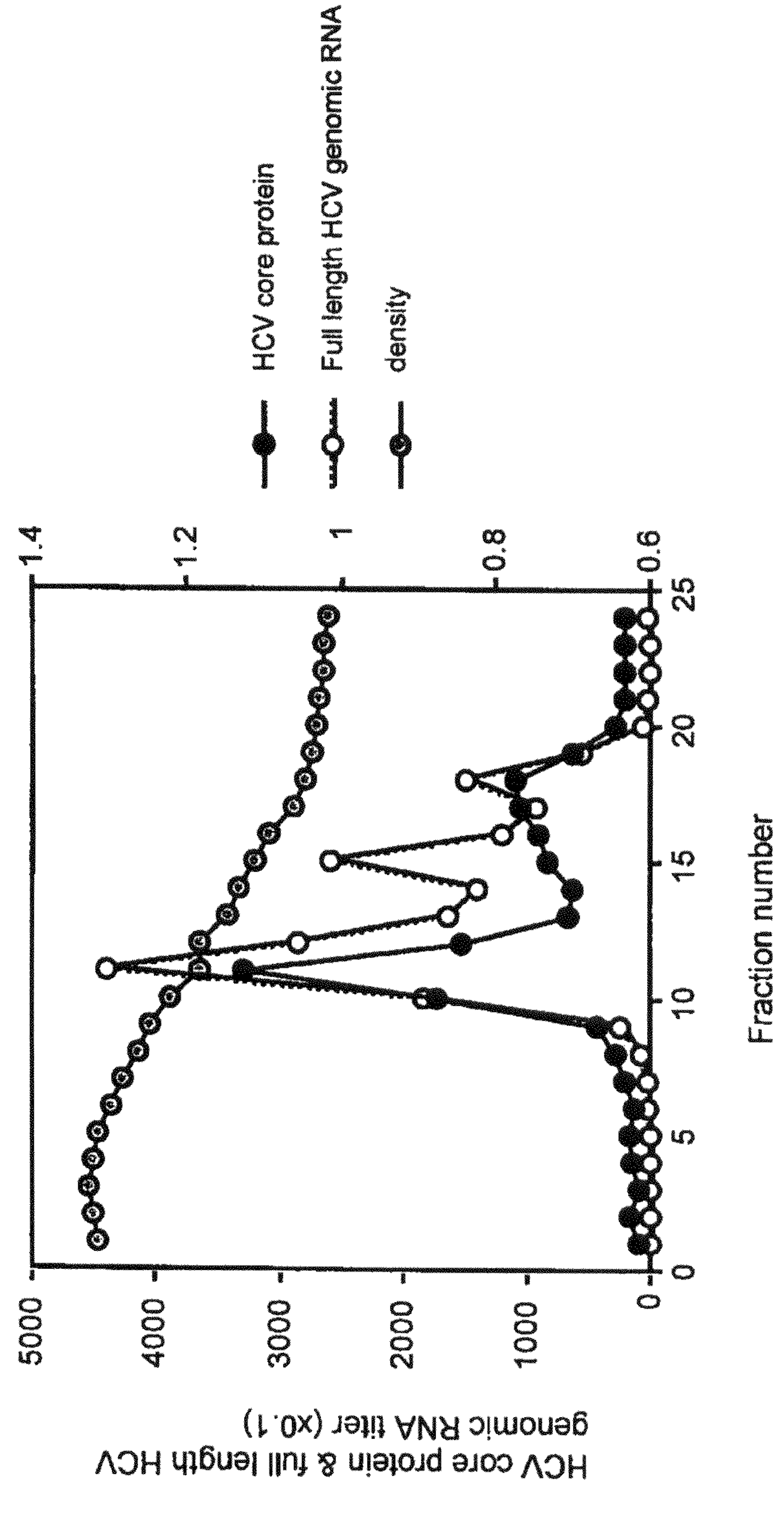
FIG. 4 is a graph showing the amounts of HCV core protein and the full length HCV genomic RNA, and the specific gravities for each of fractions that were collected by fractionating of the culture supernatant of rJFH-1-introduced Huh7 cells through sucrose density gradient. The closed circle, open circle and shaded circle represent HCV core protein, the full length HCV genomic RNA and specific gravity, respectively.

As shown in FIG. 4, the peak of core protein coincided with that of the full length HCV genomic RNA in the fraction 11. The density of this fraction was about 1.18 mg/ml and it indicated a lower specific gravity than that of the conjugate of core protein and nucleic acid reported so far. Further, when similar fractionation was carried out after treating the culture supernatant with 0.25% NP40, the peaks of core protein and the full length HCV genomic RNA were shifted to a specific gravity of about 1.28 mg/ml. That is, it was considered that the NP40 treatment stripped off the surface membrane, which contained lipid and then had a lower specific gravity, from virus particles yielding core particles comprised of only nucleic acid and core protein, and therefore the specific gravity was increased. Above results showed that the full length HCV genomic RNA was replicated in the cell by transfecting rJFH1 into Huh7 cells and, as a result, the virus particles were formed and secreted into the culture supernatant.

Example 3

(E) Preparation of the Full Length HCV Replicon RNA-Replicating Cell and Establishment of the Cell Clones The full length HCV replicon RNA-replicating cells were prepared by transfecting rFGREP-JFH1 and rFGREP-JFH1/GND, which were prepared in Example 1, into Huh7 cells as described in Example 2, and then an attempt was made to establish full length HCV replicon RNA-replicating cell clones.

First, after transfecting rFGREP-JFH1 and rFGREP-JFH1/GND respectively into Huh7 cells, the cells were seeded in culture dishes. After culturing 16-24 hours, G418 was added at various concentrations. Culturing was continued while changing the medium twice a week. After culturing for 21 days, surviving cells were stained with crystal violet. The stained colonies were counted, and the number of resulting colonies per weight of RNA used for transfection was calculated. The culturing was also continued for some of the culture dishes to clone colonies of the surviving cells. RNA, genomic DNA and proteins respectively were extracted from the cloned cells, and then detection of the full length HCV replicon RNA, integration of the neomycin resistant gene into the genomic DNA and the expression of HCV protein were investigated. These results are shown below in detail.

(F) Colony Formation Ability

Figure 5:
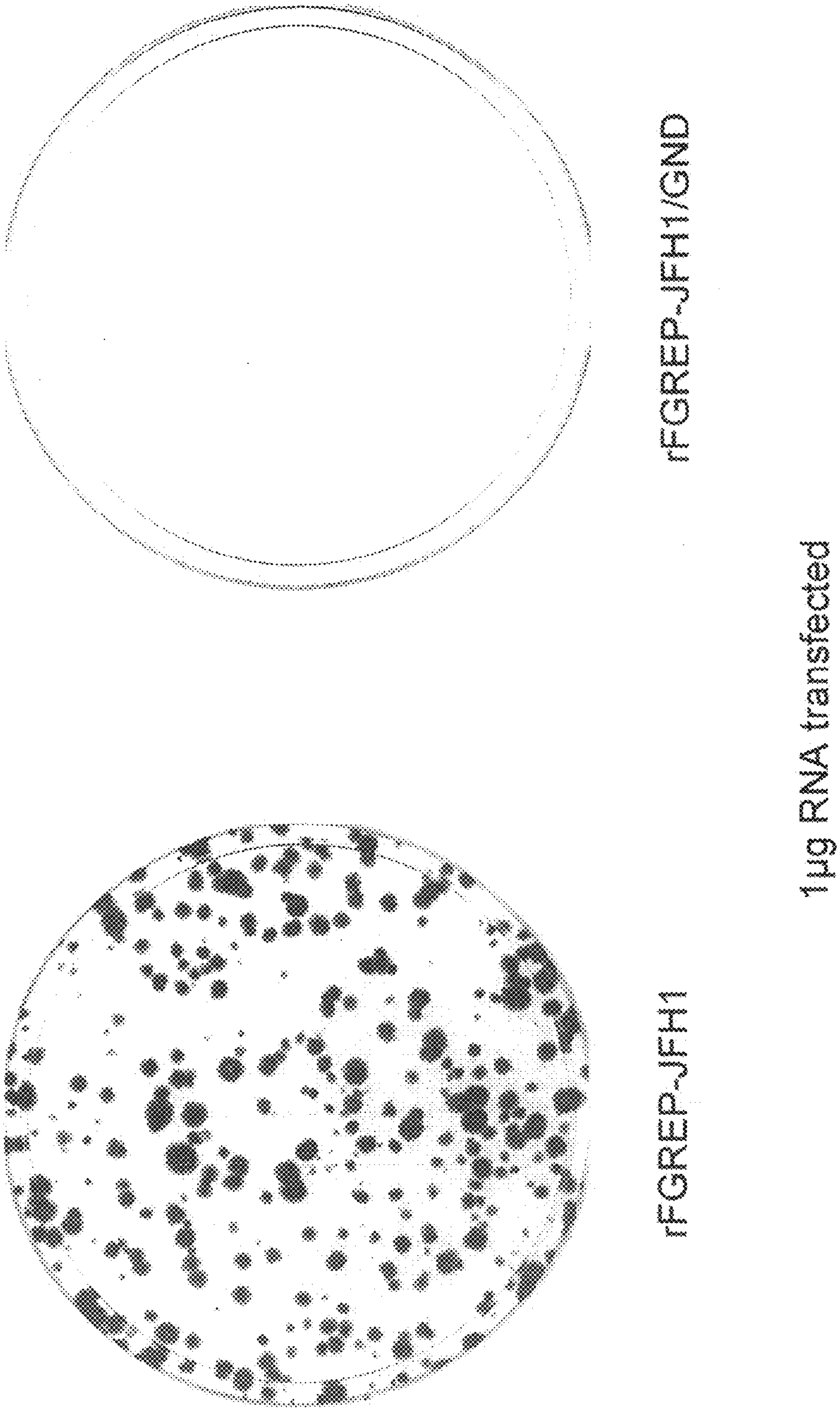
FIG. 5 is a photograph showing the colony formation of Huh7 cells into which rFGREP-JFH1, the full length HCV replicon RNA, was transfected.

The results of above transfection indicated that the colony formation ability per 1 μg of replicon RNA used for transfection was 368 CFU (Colony Forming Unit)/μg RNA, for Huh7 cells transfected with rFGREP-JFH1, at a G418 concentration of 1.0 mg/ml (the left part of FIG. 5). In contrast, no colony formation was observed for Huh7 cells transfected with rFGREP-JFH1/GND (the right part of FIG. 5). This indicates that the colony formation ability of Huh7 cells transfected with rFGREP-JFH1 replicon RNA relies on the activity of NS5B (RNA polymerase) that is expressed from rFGREP-JFH1. That is, it was considered that in the colony forming cells, the growth of cell became possible as the result of maintenance of G418 resistance due to the continuous expression of the neomycin resistant gene caused by the autonomous replication of rFGREP-JFH1 replicon RNA by means of the action of NS5B expressed from rFGREP-JFH1.

(G) Detection of the Full Length HCV Replicon RNA in Established Cell Clones

Figure 6:
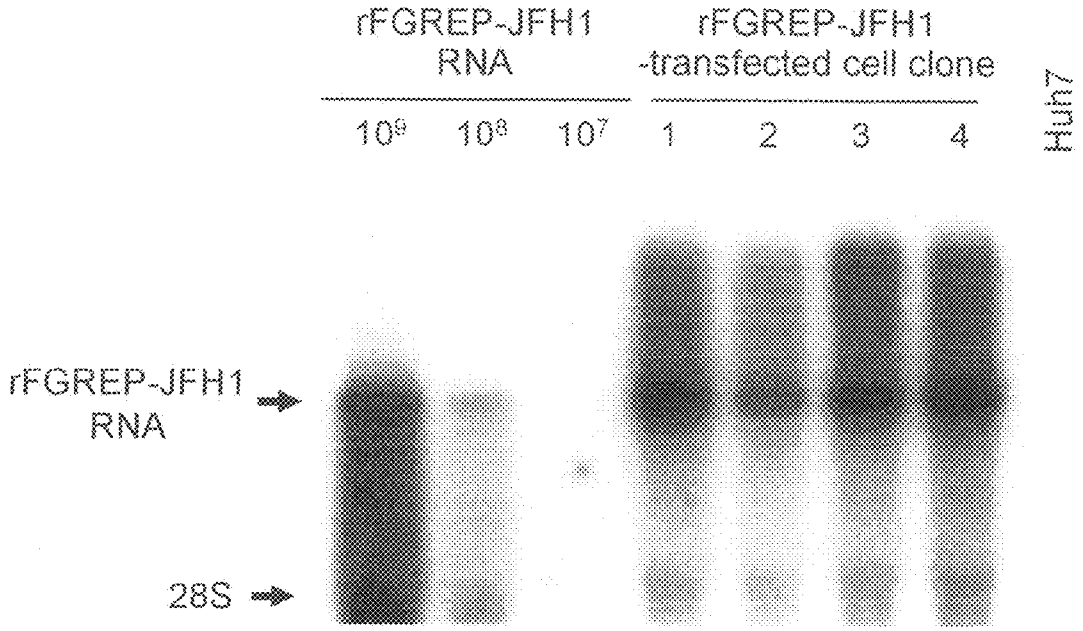
FIG. 6 is a photograph showing the replication of full length HCV replicon RNA in the full length HCV replicon RNA-replicating cell clone, which has been established by transfecting rFGREP-JFH1 into Huh7 cells.

Total RNA was extracted by the acid-phenol extraction method from full length HCV replicon RNA-replicating cell clones, which has been established by transfecting rFGREP-JFH1 into Huh7 cells according to the above section (E). Subsequently this total RNA was assayed by the Northern blot method. In the method, pFGREP-JFH1 specific probe was used. As controls, total RNA extracted from untransfected Huh7 cells in a similar manner (in FIG. 6, shown as "Huh7"), a sample containing $10^7$ copies of replicon RNA synthesized in vitro in addition to the total RNA extracted from Huh7 cells (in FIG. 6, shown as "$10^7$"), and a sample containing $10^8$ copies of replicon RNA synthesized in vitro in addition to the total RNA extracted from Huh7 cells (in FIG. 6, shown as "$10^8$") were used. In FIG. 6, 1-4 indicate cell clone numbers.

As a result, RNA having the similar size to rFGREP-JFH1 was detected with an rFGREP-JFH1 specific probe (FIG. 6). From this result, it was confirmed that the transfected rFGREP-JFH1 replicon RNA was replicated and grown in the cell clone. It was also demonstrated that there was a difference in the amount of replicon RNA among the cell clones. As shown in FIG. 6, for example, the amount of replicon RNA in clone 2 was lower than in other clones.

Figure 7:
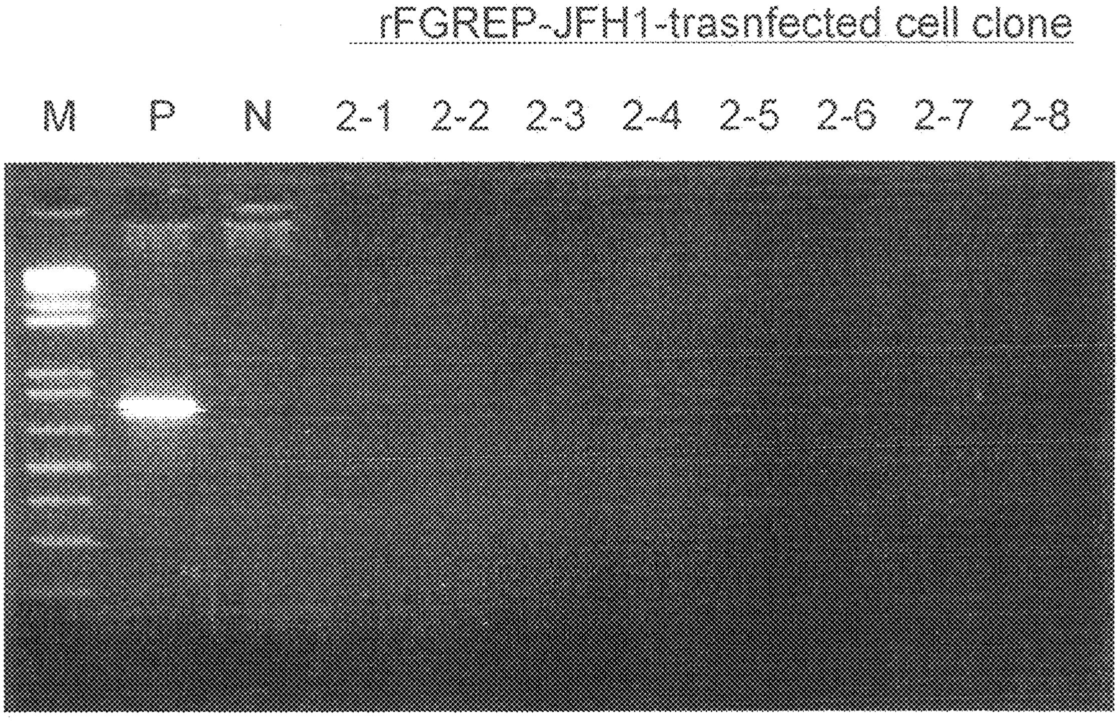
FIG. 7 is a photograph showing the result of PCR amplification using the genomic DNA of the host cell as a template and the primers specific for the neomycin resistant gene, for confirming the integration of the neomycin resistance gene into the genomic DNA. M: DNA size marker, P: Positive control, N: Huh7 cells.

(H) Confirmation of the Presence or Absence of the Integration of the Neomycin Resistance Gene into Genomic DNA For the cell clones 1-8 obtained according to the (E) (shown as FGR-JFH1/2-1 to FGR-JFH1/2-8 in FIG. 7), PCR amplification was performed using neomycin resistance gene-specific primers (sense primer, NEO-S3: 5'-AACAAGATGGATTGCACGCA-3' (SEQ ID NO: 19), antisense primer, NEO-R: 5'-CGTCAAGAAGGCGATAGAAG-3' (SEQ ID NO: 20)) and the host cellular genomic DNA extracted from each of the cell clones as a template, in order to confirm that the resistance of each of the cell clones against G418 was not due to the integration of the neomycin resistance gene into the host cellular genome. As a result, as shown in FIG. 7, no positive clone showing the amplification of the neomycin resistance gene was observed.

The result of (H) confirmed that the full length HCV replicon RNA was replicated in the cell clones established by transfection of the full length HCV replicon RNA of the present invention.

(I) Detection of HCV Protein

Figure 8:
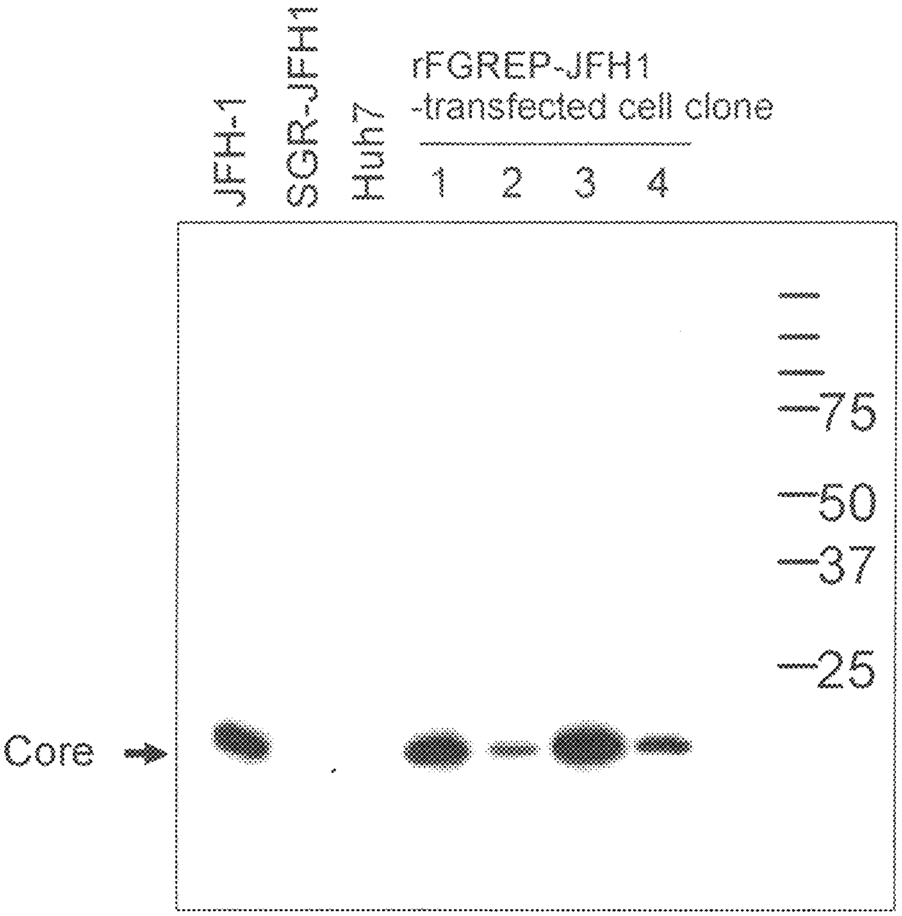
FIG. 8 is a photograph showing the result of a Western blotting analysis demonstrating the expression of core protein in Huh7 cells into which rFGREP-JFH1, the full length HCV replicon RNA, has been introduced.
Figure 9:
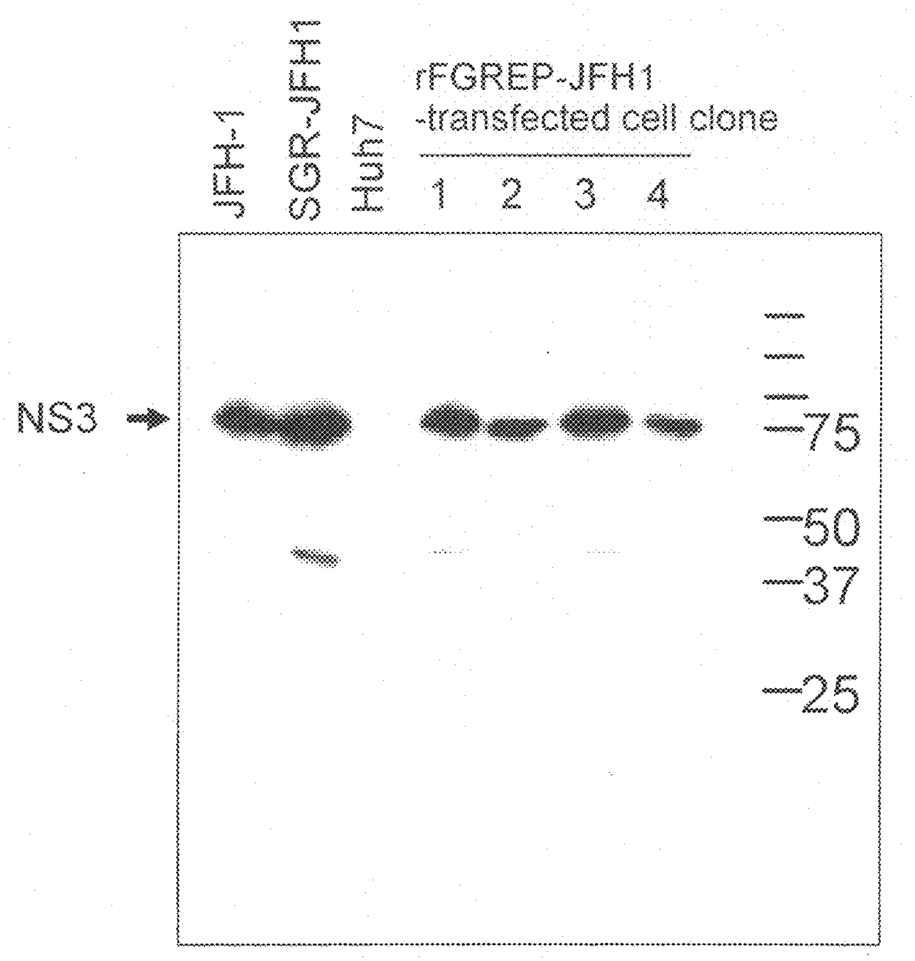
FIG. 9 is a photograph showing the result of a Western blotting analysis demonstrating the expression of NS3 protein in Huh7 cells into which rFGREP-JFH1, the full length HCV replicon RNA, has been introduced.

Proteins were extracted by a standard procedure from the cell clones established by transfection of rFGREP-JFH1, and then analyzed by SDS-PAGE and the Western blot method. The cell clones examined in this case were the same as those used in the above section (G). The cell extract obtained through the transient transfection of the prepared full length HCV genomic RNA into Huh7 cells was used as a positive control (shown as JFH-1 in FIGS. 8, 9 and 10). The cell extract from the clone obtained by transfecting the HCV subgenomic RNA replicon (SGR-JFH1) was used as a negative control for core protein and a positive control for NS3 and NS5a proteins (shown as SGR-JFH1 in FIGS. 8, 9 and 10). The cell extract from untransfected Huh7 cells was used as a negative control for all proteins (shown as Huh7 in FIGS. 8, 9 and 10). Protein samples extracted from each cell clone were blotted onto PVDF membranes (Immobilon-P, Millipore), and then core protein and NS3 protein encoded by the full length HCV replicon RNA therein were detected using an anti-core specific antibody and an anti-NS3 specific antibody (gifted by Dr. Moradpour; Wolk B, et al, J. Virology, 2000, 74: 2293-2304). As shown in FIGS. 8 and 9, for the cell clones 1-4, which were established by transfecting rFGREP-JFH1, protein of the same size as that of the positive control was detected for each protein. Since neither core protein nor NS3 protein was detected for the untransfected Huh7 cells, it was confirmed in the cell clones 1-4 that the full length HCV replicon RNA, which has been transfected, replicated autonomously and that core protein and NS3 protein were expressed.

Figure 10:
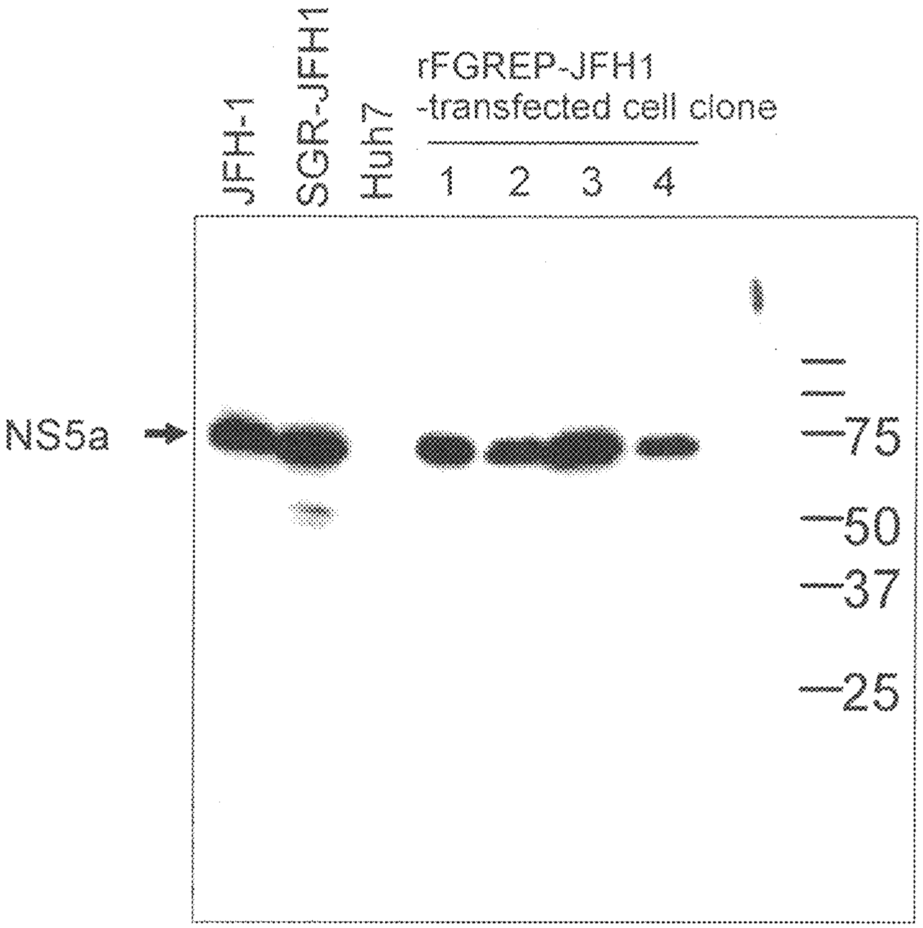
FIG. 10 is a photograph showing the result of a Western blotting analysis demonstrating the expression of NS5A protein in Huh7 cells into which rFGREP-JFH1, the full length HCV replicon RNA, has been introduced.

Further, for each cell clone, for which the expression of NS3 protein has been confirmed as described above, the expression of NS5A protein from the full length HCV replicon RNA was also confirmed using a serum from a hepatitis C patient as an antibody (FIG. 10).

From the results of (H) and (I) described above it was confirmed that in the cell clones, which have been established by transfecting the full length HCV replicon RNA, the full length HCV replicon RNA was replicated and that the viral proteins were also expressed.

Figure 11:
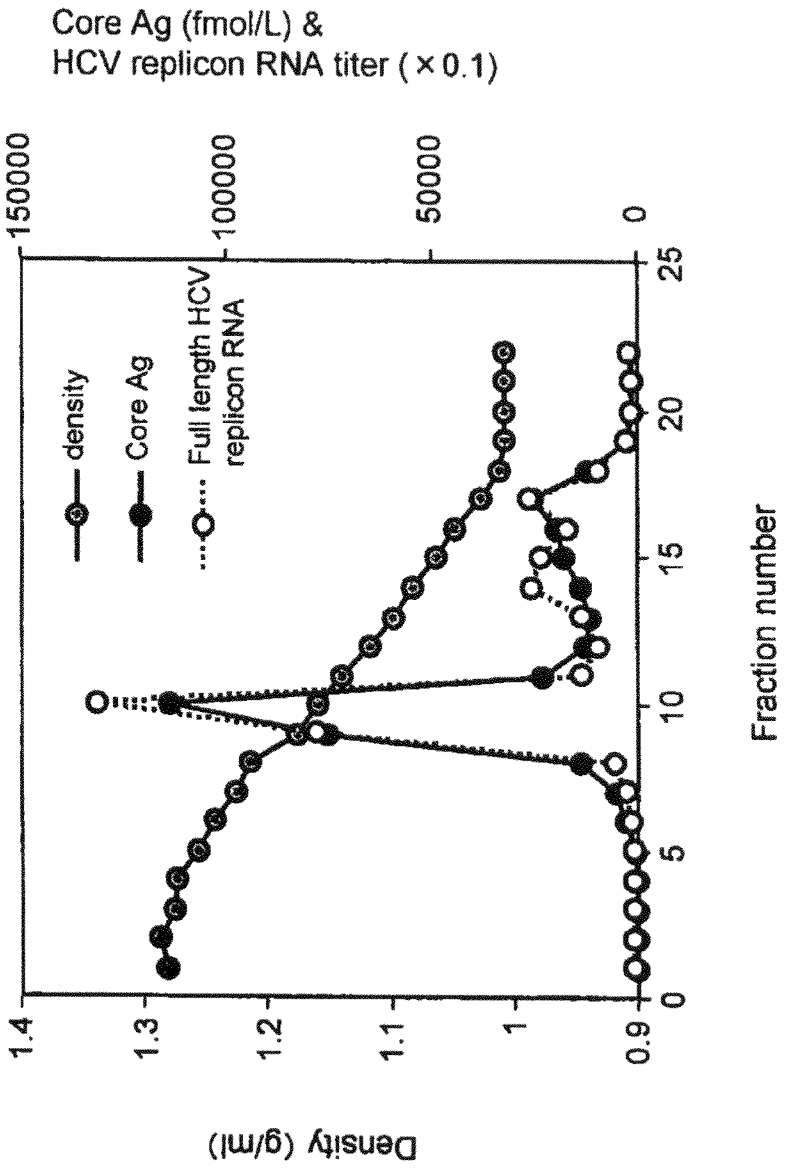
FIG. 11 is a graph showing the amounts of HCV core protein and full length HCV replicon RNA, and the specific gravities for each of fractions that were collected by fractionating of the culture supernatant of rFGREP-JFH1-introduced Huh7 cells through sucrose density gradient. The closed circle, open circle and shaded circle represent HCV core protein, the full length HCV replicon RNA and specific gravity, respectively.

(J) Virus Particle Production in the Full Length HCV Replicon RNA-Replicating Cells rFGREP-JFH1 was transfected into Huh7 cells according to the above section (E), the full length HCV replicon RNA-replicating cell clones 2 and 3 (FGR-JFH1/2-3) were established, and then their culture supernatants were recovered. HCV virus particles were assayed in the culture supernatants according to a similar method to (D) described above. The result is shown in FIG. 11. In FIG. 11, a shaded circle represents specific gravity (g/ml) of each fraction. A closed circle represents an amount of core protein (fmol/L). A open circle represents a titer of the full length HCV replicon RNA (×0.1 copy/mL).

As shown in FIG. 11, the peak of core protein coincided with that of the full length HCV replicon RNA in the fractions having specific gravities of about 1.18-1.20 mg/ml. A small peak was also found in the lighter fraction. From the above results it is shown that the full length HCV replicon RNA was replicated in Huh7 cells transfected with rFGREP-JFH11, and virus particles were formed and secreted into the culture supernatant thereof.

Example 4

(K) Infection Experiment with Virus Particles in Culture Supernatant

Huh7 cells were infected with virus particles in culture supernatant by adding each culture supernatant of cell clones 1-8 used in (H) (i.e., FGR-JFH1/2-1, FGR-JFH1/2-2, FGR-JFH1/2-3, FGR-JFH1/2-4, FGR-JFH1/2-5, FGR-JFH1/2-6, FGR-JFH1/2-7, FGR-JFH1/2-8) to Huh7 cells. On the next day G418 was added at 0.3 mg/ml to the culture media of the infected Huh7 cells, and the Huh7 cells were further cultured for 21 days. After the end of culturing, cells were fixed and stained with crystal violet. Colony formation was observed for cells infected with the culture supernatants of FGR-JFH1/

Figure 12:
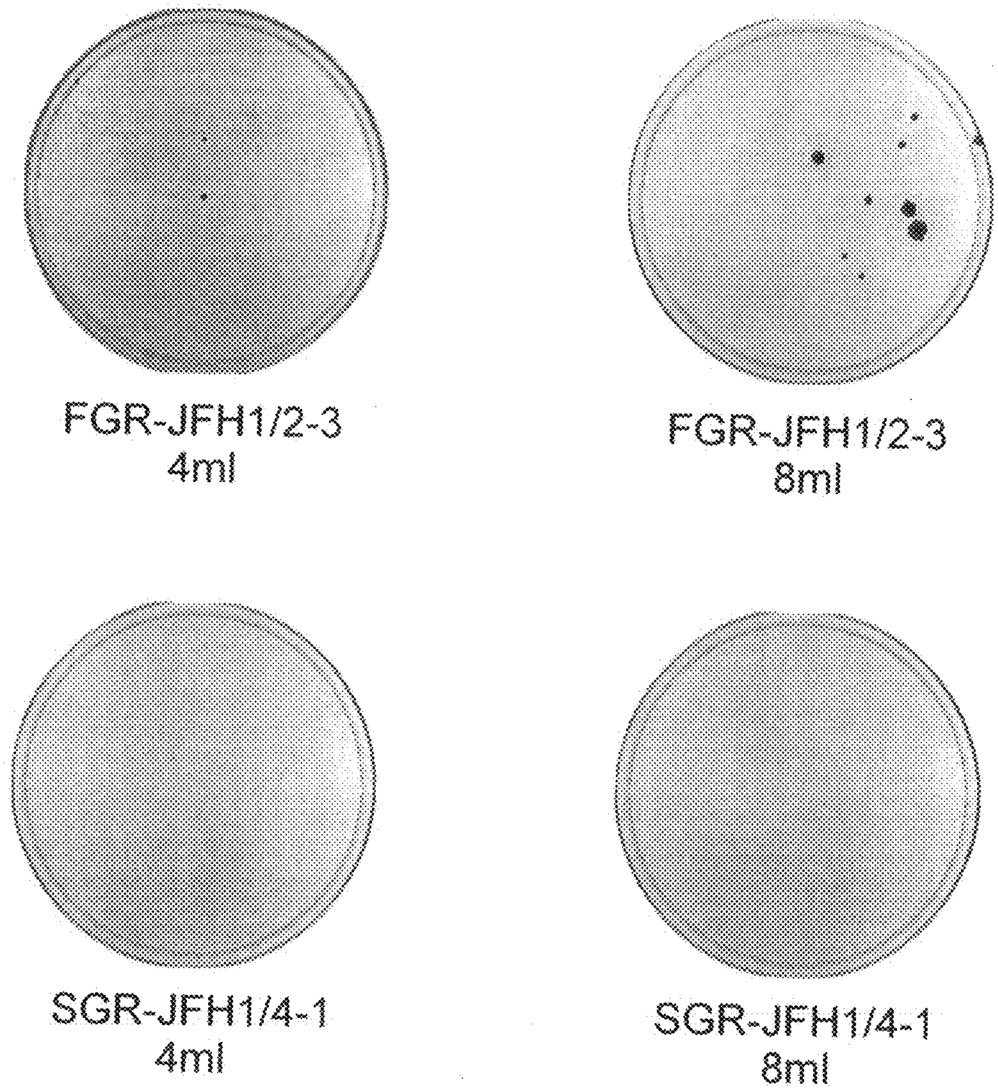
FIG. 12 is a photograph showing the colony formation of Huh7 cells to which virus particles in the culture supernatant of the full length HCV replicon RNA-replicating cell have been added.

2-3, FGR-JFH1/2-5 and FGR-JFH1/2-6, respectively. On the other hand, no colony formation was observed for cells infected with the culture supernatant of SGR-JFH1/4-1, subgenomic replicon cells (described in Non Patent Document 6), used as a control. FIG. 12 shows a photograph of a stained culture dish after culturing for 21 days with the added 4 ml or 8 ml of the culture supernatant of FGR-JFH1/2-3 or SGR-JFH1/4-1. Three and nine colonies were found in the dish in which the cells mixed with 4 ml and 8 ml of the culture supernatant of FGR-JFH1/2-3 had been seeded, respectively. However, no colony was observed in the dish, in which the cells mixed with the culture supernatant of SGR-JFH1/4-1 had been seeded.

Subsequently, colonies formed by infecting with hepatitis C virus using the culture supernatant of FGR-JFH1/2-3 and FGR-JFH1/2-5, respectively, were cloned. Three clones of FGR-JFH1/C2-3-11, FGR-JFH1/C2-3-12 and FGR-JFH1/C2-3-13 were established from the culture dish infected with the culture supernatant of FGR-JFH1/2-3, and 2 clones of FGR-JFH1/C2-5-11 and FGR-JFH1/C2-5-12, were established from the culture dish infected with the culture supernatant of FGR-JFH1/C2-5.

When Huh7 cells were infected with the culture supernatant of each cell clone of FGR-JFH1/C2-3-11, FGR-JFH1/C2-3-12, FGR-JFH1/C2-3-13, FGR-JFH1/C2-5-11 and FGR-JFH1/C2-5-12, colony formation was observed in culture dishes infected with the culture supernatant of FGR-JFH1/C2-3-12 and FGR-JFH1/C2-5-12, respectively. From the cells infected with the culture supernatant of FGR-JFH1/C2-3-12, additional 2 clones of FGR-JFH1/C2-3-12-1 and FGR-JFH1/C2-3-12-2 were established. From the cells infected with the culture supernatant of FGR-JFH1/C2-5-12, additional 2 clones of FGR-JFH1/C2-5-12-1 and FGR-JFH1/C2-5-12-2 were established.

RNA, protein and genomic DNA were extracted from these cell clones which had been established from cells infected with the culture supernatant of the full length HCV replicon RNA-replicating cells. Examination for the integration of the neomycin resistant gene into the genomic DNA of these cell clones by PCR using the genomic DNA as a template resulted in all negative. Furthermore, the full length HCV replicon RNA that is replicating in the cells could be detected by the quantitative PCR using RNA as a template. Still further, core protein could be detected in the culture supernatant. These results indicate that the virus particles containing the full length HCV replicon RNA which are produced by the full length HCV replicon RNA-replicating cell of the present invention can infect another cell.

INDUSTRIAL APPLICABILITY

According to the method of the present invention, HCV virus particles can be prepared in a cell culture system. By using the replicon RNA of the present invention, RNA containing the full length HCV genomic RNA can be produced efficiently in a cell culture system. Furthermore, by using the cells, in which the full length HCV replicon RNA or the full length HCV genomic RNA according to the present invention is introduced, the full length HCV replicon RNA or the full length HCV genomic RNA can be replicated, and the HCV virus particles of the present invention can be produced continuously in the cell culture system. The cells, in which the full length HCV replicon RNA or the full length HCV genomic RNA according to the present invention is introduced, can also be used as a test system for screening various substances which influence the process of HCV replication, virus particle formation and extracellular release of virus particles. The full length HCV replicon RNA and full length HCV genomic RNA, and virus particles of the present invention are also useful as a viral vector for a foreign gene. The virus particles of the present invention or a part thereof can be included into a vaccine as the vaccine antigen against hepatitis C virus. Further, the system, in which the virus particles of the present invention and other cells are cultured together, can be utilized as a test system for screening various substances which have an influence on the infection of cells with virus particles. The full length HCV replicon RNA or the full length HCV genomic RNA of the present invention is useful as a template which enables simple reproduction of the HCV full length genome sequence.

All publications, patents and patent applications cited herein are incorporated herein by reference in their entirety.

SEQUENCE LISTING FREE TEXT

SEQ ID NO: 1 represents the sequence of the 5' untranslated region of HCV genomic RNA derived from JFH-1 clone.

SEQ ID NO: 2 represents the core protein-coding sequence of HCV genomic RNA derived from JFH-1 clone.

SEQ ID NO: 3 represents the E1 protein-coding sequence of HCV genomic RNA derived from JFH-1 clone.

SEQ ID NO: 4 represents the E2 protein-coding sequence of HCV genomic RNA derived from JFH-1 clone.

SEQ ID NO: 5 represents the NS2 protein-coding sequence of HCV genomic RNA derived from JFH-1 clone.

SEQ ID NO: 6 represents the NS3 protein-coding sequence of HCV genomic RNA derived from JFH-1 clone.

SEQ ID NO: 7 represents the NS4A protein-coding sequence of HCV genomic RNA derived from JFH-1 clone.

SEQ ID NO: 8 represents the NS4B protein-coding sequence of HCV genomic RNA derived from JFH-1 clone.

SEQ ID NO: 9 represents the NS5A protein-coding sequence of HCV genomic RNA derived from JFH-1 clone.

SEQ ID NO: 10 represents the NS5B protein-coding sequence of HCV genomic RNA derived from JFH-1 clone.

SEQ ID NO: 11 represents the sequence of the 3' untranslated region of HCV genomic RNA derived from JFH-1 clone.

SEQ ID NO: 12 represents the sequence of the full length HCV genomic RNA derived from JFH-1 clone.

SEQ ID NO: 13 represents the sequence of the replicon RNA comprising the full length HCV genomic RNA derived from JFH-1 clone.

SEQ ID NO: 14 represents the sequence of the full length HCV genomic RNA derived from JFH-1 clone in which the amino acids motif GDD has been mutated into GND.

SEQ ID NO: 15 represents the sequence of the replicon RNA comprising the full length HCV genomic RNA derived from JFH-1 clone in which the amino acids motif GDD has been mutated into GND.

SEQ ID NOs: 16-20 represent the sequences of primers.

SEQ ID NO: 21 represents the sequence of the replicon RNA derived from an expression vector pFGREP-JFH1/Luc.

SEQ ID NO: 22 represents the sequence of the replicon RNA derived from an expression vector pFGREP-JFH1/Luc/GND.

SEQ ID NO: 23 represents the sequence of the replicon RNA derived from an expression vector pFGREP-JFH1/EGFP.

SEQ ID NO: 24 represents the sequence of the replicon RNA derived from an expression vector pFGREP-JFH1/EGFP/GND.

SEQ ID NO: 25 represents the sequence of the replicon RNA derived from an expression vector pFGREP-JFH1/SEAP.

SEQ ID NO: 26 represents the sequence of the replicon RNA derived from an expression vector pFGREP-JFH1/SEAP/GND.

The invention claimed is:

1. A method for producing a cell which replicates an RNA and produces a virus particle, comprising introducing an isolated RNA sequence comprising the nucleotide sequence shown in SEQ ID NO: 12 into a cell selected from the group consisting of a Huh7 cell, a HepG2 cell, a IMY-N9 cell, a HeLa cell and a 293 cell.

2. A method for producing a hepatitis C virus particle, comprising introducing into an isolated RNA sequence comprising the nucleotide sequence shown in SEQ ID NO: 12 into a cell selected from the group consisting of a Huh7 cell, a HepG2 cell, a IMY-N9 cell, a HeLa cell and a 293 cell and culturing the cell to allow the cell to produce a virus particle.

3. A method for producing a virus vector comprising a foreign gene, comprising inserting an isolated RNA sequence encoding a foreign gene into an RNA comprising the nucleotide sequence shown in SEQ ID NO: 12, introducing it into a cell selected from the group consisting of a Huh7 cell, a HepG2 cell, a IMY-N9 cell, a HeLa cell and a 293 cell, and culturing the cell to allow the cell to produce a virus particle.

4. The method of claim 2, which further comprises obtaining the virus particle from a supernatant of the culture.

5. The method of claim 3, which further comprises obtaining the virus particle from a supernatant of the culture.

* * * * *